(12) United States Patent
Davis et al.

(10) Patent No.: US 7,897,572 B1
(45) Date of Patent: Mar. 1, 2011

(54) THERAPUTIC METHODS FOR TYPE I DIABETES

(75) Inventors: Roger J. Davis, Princeton, MA (US); Anja Jaeschke, Worcester, MA (US)

(73) Assignee: University Of Massachusetts Medical School, Boston, MA (US)

( * ) Notice: Subject to any disclaimer, the term of this patent is extended or adjusted under 35 U.S.C. 154(b) by 48 days.

(21) Appl. No.: 11/643,480

(22) Filed: Dec. 21, 2006

Related U.S. Application Data

(63) Continuation of application No. 11/092,099, filed on Mar. 29, 2005, now abandoned.

(51) Int. Cl.
*A61K 38/00* (2006.01)
(52) U.S. Cl. .............................. 514/13; 514/15; 514/866
(58) Field of Classification Search .................. 514/44, 514/866, 13, 15; 435/183, 194
See application file for complete search history.

(56) References Cited

U.S. PATENT DOCUMENTS

| | | | | |
|---|---|---|---|---|
| 5,880,261 A | * | 3/1999 | Waeber et al. | 530/350 |
| 6,133,246 A | * | 10/2000 | McKay et al. | 514/44 |
| 6,610,820 B1 | * | 8/2003 | Bonny | 530/300 |

* cited by examiner

*Primary Examiner* — Kevin Weddington
(74) *Attorney, Agent, or Firm* — Medlen & Carroll, LLP

(57) ABSTRACT

The invention relates to the treatment and prevention of type I diabetes. More specifically, the invention relates to compounds that treat or prevent the body's immune system from destroying β-cells (i.e., insulin-producing cells in the pancreatic islets of Langerhans) by inhibition of JNK2, selective inhibition of JNK2, or inhibition of the expression of the MAPK9 gene or gene product. In one embodiment, the present invention contemplates the diagnosis, identification, production, and use of compounds which modulate MAPK9 gene expression or the activity of the MAPK9 gene product including but not limited to, JNK2, the nucleic acid encoding MAPK9 and homologues, analogues, and deletions thereof, as well as antisense, ribozyme, triple helix, antibody, and polypeptide molecules as well as small inorganic molecules. The present invention contemplates a variety of pharmaceutical formulations and routes of administration for such compounds.

4 Claims, 6 Drawing Sheets

SEQUENCE LISTING

```
<160> NUMBER OF SEQ ID NOS: 6

<210> SEQ ID NO 1
<211> LENGTH: 384
<212> TYPE: PRT
<213> ORGANISM: Homo sapiens

<400> SEQUENCE: 1

Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
```

-continued

```
                65                  70                  75                  80
Asn His Lys Asn Ile Ile Gly Leu Leu Asn Val Phe Thr Pro Gln Lys
                    85                  90                  95
Ser Leu Glu Glu Phe Gln Asp Val Tyr Ile Val Met Glu Leu Met Asp
                    100                 105                 110
Ala Asn Leu Cys Gln Val Ile Gln Met Glu Leu Asp His Glu Arg Met
                    115                 120                 125
Ser Tyr Leu Leu Tyr Gln Met Leu Cys Gly Ile Lys His Leu His Ser
                    130                 135                 140
Ala Gly Ile Ile His Arg Asp Leu Lys Pro Ser Asn Ile Val Val Lys
145                 150                 155                 160
Ser Asp Cys Thr Leu Lys Ile Leu Asp Phe Gly Leu Ala Arg Thr Ala
                    165                 170                 175
Gly Thr Ser Phe Met Met Thr Pro Tyr Val Val Thr Arg Tyr Tyr Arg
                    180                 185                 190
Ala Pro Glu Val Ile Leu Gly Met Gly Tyr Lys Glu Asn Val Asp Leu
                    195                 200                 205
Trp Ser Val Gly Cys Ile Met Gly Glu Met Val Cys His Lys Ile Leu
                    210                 215                 220
Phe Pro Gly Arg Asp Tyr Ile Asp Gln Trp Asn Lys Val Ile Glu Gln
225                 230                 235                 240
Leu Gly Thr Pro Cys Pro Glu Phe Met Lys Lys Leu Gln Pro Thr Val
                    245                 250                 255
Arg Thr Tyr Val Glu Asn Arg Pro Lys Tyr Ala Gly Tyr Ser Phe Glu
                    260                 265                 270
Lys Leu Phe Pro Asp Val Leu Phe Pro Ala Asp Ser Glu His Asn Lys
                    275                 280                 285
Leu Lys Ala Ser Gln Ala Arg Asp Leu Leu Ser Lys Met Leu Val Ile
                    290                 295                 300
Asp Ala Ser Lys Arg Ile Ser Val Asp Glu Ala Leu Gln His Pro Tyr
305                 310                 315                 320
Ile Asn Val Trp Tyr Asp Pro Ser Glu Ala Glu Ala Pro Pro Pro Lys
                    325                 330                 335
Ile Pro Asp Lys Gln Leu Asp Glu Arg Glu His Thr Ile Glu Glu Trp
                    340                 345                 350
Lys Glu Leu Ile Tyr Lys Glu Val Met Asp Leu Glu Glu Arg Thr Lys
                    355                 360                 365
Asn Gly Val Ile Arg Gly Gln Pro Ser Pro Leu Ala Gln Val Gln Gln
                    370                 375                 380

<210> SEQ ID NO 2
<211> LENGTH: 424
<212> TYPE: PRT
<213> ORGANISM: Homo sapiens

<400> SEQUENCE: 2

Met Ser Asp Ser Lys Cys Asp Ser Gln Phe Tyr Ser Val Gln Val Ala
1               5                   10                  15
Asp Ser Thr Phe Thr Val Leu Lys Arg Tyr Gln Gln Leu Lys Pro Ile
                    20                  25                  30
Gly Ser Gly Ala Gln Gly Ile Val Cys Ala Ala Phe Asp Thr Val Leu
                    35                  40                  45
Gly Ile Ser Val Ala Val Lys Lys Leu Ser Arg Pro Phe Gln Asn Gln
                    50                  55                  60
Thr His Ala Lys Arg Ala Tyr Arg Glu Leu Val Leu Leu Lys Cys Val
```

```
                65                  70                  75                  80
Asn His Lys Asn Ile Ile Ser Leu Leu Asn Val Phe Thr Pro Gln Lys
                    85                  90                  95

Thr Leu Glu Glu Phe Gln Asp Val Tyr Leu Val Met Glu Leu Met Asp
                100                 105                 110

Ala Asn Leu Cys Gln Val Ile His Met Glu Leu Asp His Glu Arg Met
                115                 120                 125

Ser Tyr Leu Leu Tyr Gln Met Leu Cys Gly Ile Lys His Leu His Ser
            130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
                180                 185                 190

Ala Pro Glu Val Ile Leu Gly Met Gly Tyr Lys Glu Asn Val Asp Ile
                195                 200                 205

Trp Ser Val Gly Cys Ile Met Gly Glu Leu Val Lys Gly Cys Val Ile
            210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
                260                 265                 270

Glu Leu Phe Pro Asp Trp Ile Phe Pro Ser Glu Ser Glu Arg Asp Lys
            275                 280                 285

Ile Lys Thr Ser Gln Ala Arg Asp Leu Leu Ser Lys Met Leu Val Ile
290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
                340                 345                 350

Lys Glu Leu Ile Tyr Lys Glu Val Met Asp Trp Glu Glu Arg Ser Lys
            355                 360                 365

Asn Gly Val Val Lys Asp Gln Pro Ser Asp Ala Ala Val Ser Ser Asn
370                 375                 380

Ala Thr Pro Ser Gln Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420

<210> SEQ ID NO 3
<211> LENGTH: 23
<212> TYPE: PRT
<213> ORGANISM: Homo sapiens

<400> SEQUENCE: 3

Asp Thr Tyr Arg Pro Lys Arg Pro Thr Thr Leu Asn Leu Phe Pro Gln
1               5                   10                  15

Val Pro Arg Ser Gln Asp Thr
```

```
<210> SEQ ID NO 4
<211> LENGTH: 21
<212> TYPE: PRT
<213> ORGANISM: Homo sapiens

<400> SEQUENCE: 4

Glu Glu Pro His Lys His Arg Pro Thr Thr Leu Arg Leu Thr Thr Leu
1               5                   10                  15

Gly Ala Gln Asp Ser
            20

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Phe Leu Asn Leu Thr Thr Pro Arg Lys Pro Arg
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Synthetic

<400> SEQUENCE: 6

Phe Leu Asn Leu Thr Thr Pro Arg Lys Pro Arg Tyr Thr Asp Gly Ser
1               5                   10                  15

Gly Thr Gly Pro Gly
            20
```

THERAPUTIC METHODS FOR TYPE I DIABETES

This application is a continuation of Ser. No. 11/092,099 filed Mar. 29, 2005, now abandoned.

This invention was made with government support under Grant No. DK063368 awarded by the National Institutes of Health. The Government has certain rights in the invention.

BACKGROUND

Insulin made in the pancreas is necessary for the body to be able to use sugar as fuel. Insulin signals the intake of sugar (i.e., glucose) from the blood into cells of the body (e.g., muscles). In type I diabetes, the pancreas no longer produces insulin; so, patients with type I diabetes need to take insulin shots in order to compensate for the pancreas' inability to produce insulin. Conditions associated with type I diabetes include hypoglycemia, ketoacidosis and celiac disease. Having type I diabetes increases your risk for many serious complications including: heart disease (cardiovascular disease), blindness (retinopathy), nerve damage (neuropathy), and kidney damage (nephropathy). The insulin shortage in type I diabetes is believed to be caused by an autoimmune process in which the body's immune system destroys the β-cells in the pancreas. Thus, there is a need to identify methods of treating and preventing type I diabetes by preventing the body's immune system from destroying β-cells in the pancreas.

SUMMARY OF THE INVENTION

The invention relates to the treatment and prevention of type I diabetes. More specifically, the invention relates to compounds that treat or prevent the body's immune system from destroying β-cells (i.e., insulin-producing cells in the pancreatic islets of Langerhans) by inhibition of JNK2, selective inhibition of JNK2, or inhibition of the expression of the MAPK9 gene or gene product. In one embodiment, the present invention contemplates the diagnosis, identification, production, and use of compounds which modulate MAPK9 gene expression or the activity of the MAPK9 gene product including but not limited to, JNK2, the nucleic acid encoding MAPK9 and homologues, analogues, and deletions thereof, as well as antisense, ribozyme, triple helix, antibody, and polypeptide molecules as well as small inorganic molecules. The present invention contemplates a variety of pharmaceutical formulations and routes of administration for such compounds.

In one embodiment, the invention is a method for treating type I diabetes in a subject, comprising administering a compound that inhibits activity of JNK2 in the subject. In further embodiments, the compound inhibits the enzymatic activity of JNK2, and has minimal effect on enzymatic activity of JNK1. In further embodiments, the activity of JNK1 is not inhibited.

It is not intended that the present invention be limited to complete inhibition of JNK2. For example, it is sufficient that the inhibitor has an $IC_{50}$ of less than 10 mM in a c-jun phosphorylation assay described below. Inhibition can be measured in vitro or in vivo. In vitro inhibition is readily measured in a variety of assays (an example of which is provided below). Inhibition in vivo is established by the observation of reduced insulitis (e.g. a reduction in non-diabetic obese mice islets showing invasive, destructive, or peri-insulitis of 10% or more as measured by a histological analysis of the pancreas).

In another embodiment, the invention is a method for treating type I diabetes in a subject, comprising administering a compound that selectively inhibits activity of JNK2 compared to JNK1 in a subject, wherein the activity of the compound does not result in adverse drug reactions to the subject. It is not intended that the present invention be limited to complete absence of adverse drug reactions in the subject.

In another embodiment, the invention is a method of treating type I diabetes in a subject, comprising administering an antisense oligonucleotides of MAPK9 that inhibits the expression of JNK2. In further embodiments, the antisense oligonucleotide of JNK2 inhibits the expression of JNK2, and has minimal effect on the expression of JNK1.

In another embodiment, the invention is a method of treating type I diabetes in a subject, comprising administering an amino acid sequence within JIP-1 or JIP-2 that inhibits the activity of JNK2 in the subject (i.e. a portion preferably comprising at least 10 amino acids and more preferably at least 18). In further embodiments, the amino acid sequence has a minimal effect on the enzymatic activity of JNK1.

In another embodiment, the invention is a method of treating type I diabetes in a subject, comprising administering a compound of the following formula:

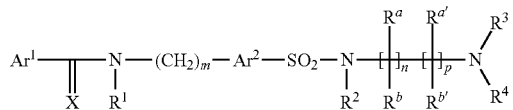

wherein: $Ar^1$ is a substituted or unsubstituted aryl or heteroaryl group; X is O or S; $Ar^2$ a substituted or unsubstituted aryl or heteroaryl group; $R^1$ and $R^2$ are independently selected from the group consisting of hydrogen and a $C_1$-$C_6$-alkyl group; $R^a$, $R^{a'}$, $R^b$, $R^{b'}$ are independently selected from the group consisting of hydrogen and $C_1$-$C_6$-alkyl; or $R^{a'}$ and $R^a$ or $R^{b'}$ together with the carbon atoms they are linked, form a substituted or unsubstituted 5-8-membered saturated, partially unsaturated or aromatic ring containing optionally one or more heteroatoms selected from O, N, S; $R^3$ is selected from the group consisting of H, $C_1$-$C_{10}$-alkyl, $C_2$-$C_{10}$-alkenyl, $C_2$-$C_{10}$-alkynyl, aryl, heteroaryl, 3-8 membered cycloalkyl optionally containing 1-3 heteroatoms selected from the group consisting of N, O, and S; aryl $C_1$-$C_{10}$-alkyl and heteroaryl $C_1$-$C_{10}$-alkyl; or $R^3$ and $R^a$ or $R^{a'}$ form, together with the N atom linked to $R^3$, a 5-8-membered saturated ring, containing optionally at least one further heteroatom selected from O, N, S; $R^4$ is selected from the group consisting of H and —C(H)$R^5R^6$; $R^5$ and $R^6$ are independently selected from the group consisting of H, $C_1$-$C_{10}$-alkyl, $C_2$-$C_{10}$-alkenyl, $C_2$-$C_{10}$-alkynyl, aryl, heteroaryl, 3-8 membered cycloalkyl optionally containing 1-3 heteroatoms selected from the group consisting of N, O, and S; aryl $C_1$-$C_{10}$-alkyl and heteroaryl m is an integer from 1 to 5; n is an integer from 0 to 2; and p is an integer from 1 to 10; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

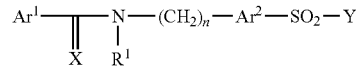

wherein $Ar^1$ and $Ar^2$ are independently from each other substituted or unsubstituted aryl or heteroaryl groups; X is O or S; $R^1$ is hydrogen or a $C_1$-$C_6$ alkyl group, or $R^1$ forms a substituted or unsubstituted 5-6 membered saturated or unsaturated ring with $Ar^1$; n is an integer from 0 to 5, preferably between 1-3 and most preferred 1; Y is an unsubstituted or a substituted 4-12 membered saturated cyclic or bicyclic alkyl containing at least one nitrogen atom, whereby one nitrogen atom within said ring is forming a bond with the sulfonyl group thus providing a sulfamide: that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

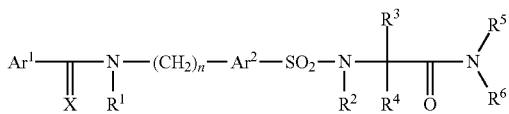

wherein $Ar^1$ and $Ar^2$ are independently from each other substituted or unsubstituted aryl or heteroaryl; X is O or S; $R^1$ is hydrogen or an unsubstituted or substituted $C_1$-$C_6$-alkyl group, or $R^1$ could form a substituted or unsubstituted 5-6-membered saturated or unsaturated fused ring with $Ar^1$, or $R^2$ and $R^4$ form a substituted or unsubstituted 5-6-membered saturated or non-saturated ring; $R^2$ is hydrogen or a substituted or unsubstituted $C_1$-$C_6$-alkyl group; n is an integer from 0 to 5; $R^3$ and $R^4$ are independently from each other selected from the group comprising or consisting of natural amino acid residues or synthetic amino acid residues, hydrogen, substituted or unsubstituted $C_1$-$C_6$-alkyl, like trihalomethyl, substituted or unsubstituted $C_1$-$C_6$-alkoxy, $NH_2$, SH, thioalkyl, aminoacyl, aminocarbonyl, substituted or unsubstituted $C_1$-$C_6$-alkoxycarbonyl, aryl, heteroaryl, substituted or unsubstituted 4-8-membered cyclic alkyl, optionally containing 1-3 heteroatoms, carboxyl, cyano, halogen, hydroxy, nitro, acetoxy, aminoacyl, sulfoxy, sulfonyl, $C_1$-$C_6$-thioalkoxy, whereby at least one of $R^3$ and/or $R^4$ must be an amino acid residue; $R^5$ is H or substituted or unsubstituted $C_1$-$C_6$-alkyl; $R^6$ is selected from the group comprising or consisting of H, substituted or unsubstituted $C_1$-$C_6$-aliphatic alkyl, substituted or unsubstituted saturated cyclic $C_4$-$C_8$-alkyl optionally containing 1-3 heteroatoms and optionally fused with an aryl or an heteroaryl; or $R^6$ is a substituted or unsubstituted aryl, substituted or unsubstituted heteroaryl, whereby said aryl or heteroaryl groups are optionally substituted with substituted or unsubstituted $C_1$-$C_6$-alkyl, like trihalomethyl, substituted or unsubstituted $C_1$-$C_6$-alkoxy, substituted or unsubstituted $C_2$-$C_6$-alkenyl, substituted or unsubstituted $C_2$-$C_6$-alkynyl, amino, aminoacyl, aminocarbonyl, substituted or unsubstituted $C_1$-$C_6$-alkoxycarbonyl, aryl, carboxyl, cyano, halogen, hydroxy, nitro, acetoxy, aminoacyl, sulfoxy, sulfonyl, $C_1$-$C_6$-thioalkoxy; or $R^5$ and $R^6$ taken together could form a substituted or unsubstituted 4-8-membered saturated cyclic alkyl or heteroalkyl group; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

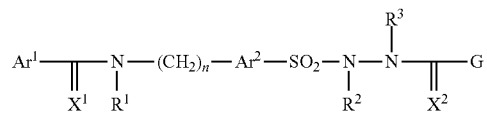

wherein $Ar^1$ and $Ar^2$ are independently from each other substituted or unsubstituted aryl or heteroaryl groups; $X^1$ and $X^2$ are independently from each other O or S; $R^1$, $R^2$, and $R^3$ are independently from each other hydrogen or a $C_1$-$C_6$ alkyl substituent or $R^1$ forms a substituted or unsubstituted 5-6-membered saturated or unsaturated ring with $Ar^1$; or $R^2$ and $R^3$ form a substituted or unsubstituted 5-6-membered saturated or unsaturated ring; n is an integer from 0 to 5; G is selected from a group comprising or consisting of an unsubstituted or substituted 4-8-membered heterocycle containing at least one heteroatom, or G is a substituted or unsubstituted $C_1$-$C_6$ alkyl group; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

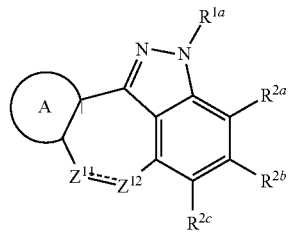

wherein $Z^{11}$ and $Z^{12}$ each independently represent a carbonyl group, an oxygen atom, a sulfur atom, a methine group which may be substituted, a methylene group which may be substituted or a nitrogen atom which may be substituted; ==== represents a double bond or a single bond; $R^{1a}$ represents a hydrogen atom, a $C_1$-$C_6$ alkyl group, a phenyl group or a benzyl group; $R^{2a}$, $R^{2b}$ and $R^{2c}$ each independently represent a group selected from the following Substituent Group (a); the ring A represents a benzene ring which may have one to three groups selected from the following Substituent Group (a), a naphthalene ring which may have one to three groups selected from the following Substituent Group (a) or a 5- to 10-membered aromatic heterocyclic ring which may have one to three groups selected from the following Substituent Group (a); Substituent Group (a) (1) a hydrogen atom, (2) halogen atoms, (3) a nitro group, (4) a hydroxyl group, (5) a cyano group, (6) a carboxyl group, (7) an amino group, (8) a formyl group or (9) a group represented by the formula:

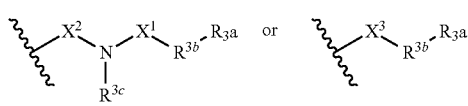

wherein $X^1$ and $X^2$ each independently represent a single bond, —CO—, —$SO_2$— or $C_1$-$C_6$-methylene group; $X^3$ represents a single bond, —CO—, —$SO_2$, —O—, —CO—O— or —O—CO—; $R^{3b}$ represents a $C_1$-$C_6$ alkylene group or a single bond; $R^{3a}$ and $R^{3c}$ represent a hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_8$ cycloalkyl group which may be substituted, a $C_6$-$C_{14}$ aromatic cyclic hydrocarbon group which may be substituted, a 5- to 14-membered aromatic heterocyclic group which may be substituted or a hydrogen atom; that inhibits the activity of JNK2 in the subject. In further embodiments, the compound has a minimal effect on the enzymatic activity of JNK1

In another embodiment, the invention is a method of treating type I diabetes in a subject, comprising administering a compound of the following formula:

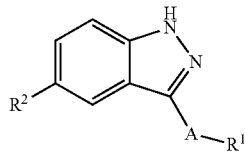

wherein A is a direct bond, $-(CH_2)_a-(CH_2)_bCH=CH(CH_2)_c-$, or $-(CH_2)_bC\equiv C(CH_2)_c-$; $R^1$ is aryl, heteroaryl or heterocycle fused to phenyl, each being optionally substituted with one to four substituents independently selected from $R^3$; $R^2$ is $-R^3$, $-R^4$, $-(CH_2)_bC(=O)R^5$, $-(CH_2)_bC(=O)OR^5$, $-(CH_2)_bC(=O)NR^5R^6$, $-(CH_2)_bC(=O)NR_5(CH_2)CC(=O)R^6$, $-(CH_2)_bNR^5C(=O)R^6$, $-(CH_2)_b NR^5C(=O)NR^6R^7$, $-(CH_2)_bNR^5R^6$, $-(CH_2)_bOR^5$, $-(CH^2)_bSO_dR^5$ or $-(CH_2)_bSO_2NR^5R^6$; a is 1, 2, 3, 4, 5 or 6; b and c are the same or different and at each occurrence independently selected from 0, 1, 2, 3 or 4; d is at each occurrence 0, 1 or 2; $R^3$ is at each occurrence independently halogen, hydroxy, carboxyl, alkyl, alkoxy, haloalkyl, acyloxy, thioalkyl, sulfinylalkyl, sulfonylalkyl, hydroxyalkyl, aryl, arylalkyl, heterocycle, heterocycloalkyl, $-C(=O)R^8$, $-OC(=O)R^8$, $-C(=O)NR^8R^9$, $-C(=O)NR^8OR^9$, $-SO_2NR^8R^9$, $-NR^8SO_2R^9$, CN, $-NO_2$, $-NR^8R^9$, $-NR^8C(=O)R^9$, $NR^8C(=O)(CH_2)_bOR^9$, $-NR^8C(=O)(CH_2)_bR^9$, $-O(CH_2)_bNR^8R^9$, or heterocycle fused to phenyl; $R^4$ is alkyl, aryl, arylalkyl, heterocycle or heterocycloalkyl, each being optionally substituted with one to four substituents independently selected from $R^3$, or $R^4$ is halogen or hydroxy; $R^5$, $R^6$ and $R^7$ are the same or different and at each occurrence independently hydrogen, alkyl, aryl, arylalkyl, heterocycle or heterocycloalkyl, wherein each of $R^5$, $R^6$ and $R^7$ are optionally substituted with one to four substituents independently selected from $R^3$; and $R^8$ and $R^9$ are the same or different and at each occurrence independently hydrogen, alkyl, aryl, arylalkyl, heterocycle, or heterocycloalkyl, or $R^8$ and $R^9$ taken together with the atom or atoms to which they are bonded form a heterocycle, wherein each of $R^8$, $R^9$, and $R^8$ and $R^9$ taken together to form a heterocycle are optionally substituted with one to four substituents independently selected from $R^3$; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

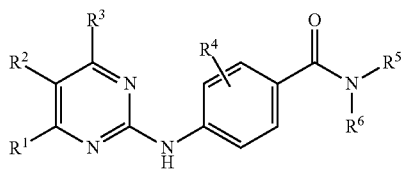

wherein $R^1$ is aryl or heteroaryl optionally substituted with one to four substituents independently selected from $R^7$; $R^2$ is hydrogen; $R^3$ is hydrogen or lower alkyl; $R^4$ represents one to four optional substituents, wherein each substituent is the same or different and independently selected from halogen, hydroxy, lower alkyl and lower alkoxy; $R^5$ and $R^6$ are the same or different and independently $-R^8$, $-(CH_2)_aC(=O)R^9$, $-(CH2)_aC(=O)OR^9$, $-(CH2)_aC(=O)NR^9R^{10}$, $-(CH2)_aC(=O)NR^9(CH2)_bC(=O)R^{10}$, $-(CH2)_aNR^9C(=O)R^{10}$, $(CH2)_aNR^{11}C(=O)NR^9R^{10}$, $(CH2)_aNR^9R^{10}$, $-(CH2)_aOR^9$, $-(CH2)_aSO_cR^9$ or $-(CH2)_nSO2NR^9R^{10}$; or $R^5$ and $R^6$ taken together with the nitrogen atom to which they are attached to form a heterocycle or substituted heterocycle; $R^7$ is at each occurrence independently halogen, hydroxy, cyano, nitro, carboxyl, alkyl, alkoxy, haloalkyl, acyloxy, thioalkyl, sulfinylalkyl, sulfonylalkyl, hydroxyalkyl, aryl, arylalkyl, heterocycle, substituted heterocycle, heterocycloalkyl, $-C(=O)OR^8$, $-OC(=O)R^8$, $-C(=O)NR^8R^9$, $-C(=O)NR^8OR^9$, $-SO_cR^8$, $-SO_cNR^8R^9$, $-NR^8SOR^9$, $-NR^8R^9$, $-NR^8C(=O)R^9$, $-NR^8C(=O)(CH_2)_bOR^9$, $-NR^8C(=O)(CH2)_bR^9$, $-O(CH2)_bNR^8R^9$, or heterocycle fused to phenyl; $R^8$, $R^9$, $R^{10}$ and $R^{11}$ are the same or different and at each occurrence independently hydrogen, alkyl, aryl, arylalkyl, heterocycle, heterocycloalkyl; or $R^8$ and $R^9$ taken together with the atom or atoms to which they are attached to form a heterocycle; a and b are the same or different and at each occurrence independently selected from 0, 1, 2, 3 or 4; and c is at each occurrence 0, 1 or 2; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

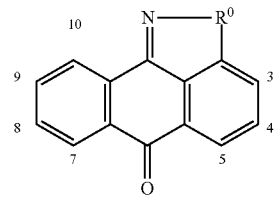

wherein $R^0$ is $-O-$, $-S(O)-$, $-S(O)_2-$, NH or $-CH_2-$; being: (i) unsubstituted, (ii) monosubstituted and having a first substituent, or (iii) disubstituted and having a first substituent and a second substituent; the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, $NHR^3R^4$, $-NH(CH_2)_nNR^3R^4$, $-NH(=O)R^5$, $-NHSO_2R^5$, $-C(=O)NR^3R^4$, or $-SO_2NR^3R^4$; wherein n is 0-6, $R^3$ and $R^4$ are taken together and represent alkylidene or a heteroatom-containing cyclic alkylidene or $R^3$ and $R^4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and $R^5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

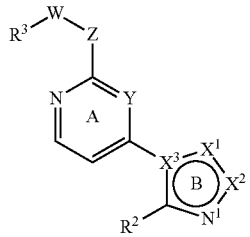

wherein N¹ is a nitrogen atom optionally having a substituent or a hydrogen atom, X¹ is (i) a carbon atom optionally having substituent(s) or hydrogen atom(s), (ii) an oxygen atom, (iii) a sulfur atom or (iv) a nitrogen atom optionally having a substituent or a hydrogen atom, X² is (i) a carbon atom optionally having substituent(s) or hydrogen atom(s), (ii) an oxygen atom, (iii) a sulfur atom or (iv) a nitrogen atom optionally having a substituent or a hydrogen atom, X³ is (i) a carbon atom or (ii) a nitrogen atom, wherein (1) when X¹ is an oxygen atom or a sulfur atom, X² is a carbon atom optionally having substituent(s) or hydrogen atom(s), X³ is a carbon atom and N¹ is a nitrogen atom, (2) when X¹ is a nitrogen atom having a substituent or a hydrogen atom and X³ is a carbon atom, X2 is a carbon atom optionally having substituent(s) or hydrogen atom(s) and N¹ is a nitrogen atom, (3) when X¹ and X³ are each a nitrogen atom, X² is a carbon atom optionally having substituent(s) or hydrogen atom(s), and N¹ is a nitrogen atom, (4) when X¹ is a carbon atom optionally having substituent(s) or hydrogen atom(s) and X² is an oxygen atom or a sulfur atom, X³ is a carbon atom and N¹ is a nitrogen atom, (5) when X¹ is a carbon atom optionally having substituent(s) or hydrogen atom(s) and X³ is a carbon atom, one of N¹ and X² is a nitrogen atom, and the other is a nitrogen atom having a substituent or a hydrogen atom, (6) when X¹ and X² are each a carbon atom optionally having substituent(s) or hydrogen atom(s) and X³ is a carbon atom, N¹ is a nitrogen atom having a substituent or a hydrogen atom, and (7) when X¹ and X² are each a carbon atom optionally having substituent(s) or hydrogen atom(s) and X³ is a nitrogen atom, N¹ is a nitrogen atom, ring A optionally further has substituent(s), ring B is an aromatic ring, Y is (i) a carbon atom optionally having substituent(s) or hydrogen atom(s) or (ii) a nitrogen atom, Z is a bond, —NR⁴— (R⁴ is a hydrogen atom or a hydrocarbon group optionally having substituent(s)), an oxygen atom or an optionally oxidized sulfur atom, W is a bond or a divalent hydrocarbon group optionally having substituent(s), R² is an aromatic group optionally having substituent(s), and R³ is a hydrocarbon group optionally having substituent(s) or a heterocyclic group optionally having substituent(s); that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

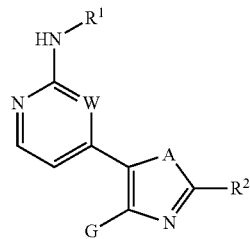

wherein: W is nitrogen or CH; G is hydrogen or $C_{1-3}$ aliphatic wherein one methylene unit of G is optionally replaced by —C(O)—, —C(O)O—, —C(O)NH—, —SO₂—, or —SO₂NH—; A is —N-T$_{(n)}$-R, oxygen, or sulfur; R¹ is selected from -T$_{(n)}$-R or -T$_{(n)}$-Ar¹; each n is independently 0 or 1; T is a $C_{1-4}$ alkylidene chain wherein one methylene unit of T is optionally replaced by —C(O)—, —C(O)O—, —C(O)NH—, —SO₂—, or —SO₂NH—; Ar¹ is a 3-7 membered monocyclic saturated, partially saturated or aromatic ring having 0-3 heteroatoms independently selected from nitrogen, oxygen, or sulfur, or a 8-10 membered bicyclic saturated, partially saturated or aromatic ring having 0-5 heteroatoms independently selected from nitrogen, oxygen, or sulfur, wherein each member of Ar¹ is optionally substituted with one —Z—R³ and one to three additional groups independently selected from —R, halogen, oxo, —NO₂, —CN, —OR, —SR, —N(R)₂, —NRC(O)R, —NRC(O)N(R)₂, —NRCO₂R, —C(O)R, —CO₂R, —OC(O)R, —C(O)N(R)₂, —OC(O)N(R)₂, —S(O)R, —SO₂R, —SO₂N(R)₂, —NRSO₂R, —NRSO₂N(R)₂, —C(O)C(O)R, or —C(O)CH₂C(O)R; each R is independently selected from hydrogen or a $C_{1-6}$ aliphatic, wherein said aliphatic is optionally substituted with one to three groups independently selected from oxo, —CO₂R', —OR', —N(R')₂, —SR', —NO₂, —NR'C(O)R', —NR'C(O)N(R')₂, —NR'CO₂R', —C(O)R', —OC(O)R', —C(O)N(R')₂, —OC(O)N(R')₂, S(O)R', —SO₂R', —SO₂N(R')₂, —NR'SO₂R', —NR'SO₂N(R')₂, —C(O)C(O)R', —C(O)CH₂C(O)R', halogen, or —CN, or two R bound to the same nitrogen atom are taken together with that nitrogen atom to form a five or six membered heterocyclic or heteroaryl ring having one to two additional heteroatoms independently selected from oxygen, nitrogen, or sulfur; each R' is independently selected from hydrogen or $C_{1-6}$ aliphatic, wherein said aliphatic is optionally substituted with one to three groups independently selected from oxo, —CO₂H, —OH, —NH₂, —SH, —NO₂, —NHC(O)H, —NHC(O)NH₂, —NHCO₂H, —C(O)H, —OC(O)H, —C(O)NH₂, —OC(O)NH₂, —S(O)H, —SO₂H, —SO₂NH₂, —NHSO₂H, —NHSO₂NH₂, —C(O)C(O)H, —C(O)CH₂C(O)H, halogen, or —CN, or two R' bound to the same nitrogen atom are taken together with that nitrogen atom to form a five or six membered heterocyclic or heteroaryl ring optionally having one or two additional heteroatoms independently selected from nitrogen, oxygen, or sulfur; Z is a $C_1$-$C_6$ alkylidene chain wherein up to two nonadjacent methylene units of Z are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, —N(R)C(O)N(R)—, —S(O)—, —SO₂—, —N(R)SO₂—, —SO₂N(R)—, —N(R)SO₂N(R)—, —O—, —S—, or —N(R)—; R² is -Q$_{(n)}$-Ar²; Ar² is selected from a 3-7 membered monocyclic saturated, saturated or aromatic ring having 0-3 heteroatoms independently selected from nitrogen, oxygen, or sulfur, or a 8-10 membered bicyclic saturated, saturated or aromatic ring having 0-5 heteroatoms independently selected from nitrogen, oxygen, or sulfur, wherein each member of Ar² is optionally substituted with 1-5 groups independently selected from —Z—R³, —R, halogen, oxo, —NO2, —CN, —OR, —SR, —N(R)₂, NRC(O)R, —NRC(O)N(R)₂, —NRCO₂R, —C(O)R, —CO₂R, OC(O)R, —C(O)N(R)₂, —OC(O)N(R)₂, —S(O)R, —SO₂R, SO₂N(R)₂, —N(R)SO₂R, —N(R)SO₂N(R)₂, —C(O)C(O)R, or —C(O)CH₂C(O)R; Q is a C₁₋₃ alkylidene chain wherein up to two nonadjacent methylene units of Q are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, N(R)C(O)N(R)—, —S(O)—, —SO₂—, —N(R)SO₂—, —SO₂N(R)—, —N(R)SO₂N(R)—, —O—, —S—, or —N(R)—; R³ is selected from —Ar³, —R, halogen, —NO₂, —CN, —OR, —SR, —N(R)₂, —NRC(O)R, —NRC(O)N(R)₂, —NRCO₂R, —C(O)R, —CO₂R, —OC(O)R, —C(O)N(R)₂, —OC(O)N(R)₂, —SOR, —SO₂R, —SO₂N(R)₂, —NRSO₂R, —NRSO₂N(R)₂, —C(O)C(O)R, or —C(O)CH2C(O)R; and Ar³ is a 5-6 membered saturated, partially saturated, or aromatic ring having 0-3 heteroatoms independently selected from nitrogen, oxygen, or sulfur, wherein each member of Ar³ is optionally substituted with halogen, oxo, —CN, —NO₂, —R', —OR', —N(R')₂, —N(R')C(O)R', N(R')C(O)N(R')₂, —N(R')CO₂R', —C(O)R', —CO₂R', OC(O)R', —C(O)N(R')₂, —OC(O)N(R')₂, or —SO₂R'; provided that when W is nitrogen and: (i) A is —N-T₍ₙ₎-R and R2 is a saturated ring or (ii) A is sulfur, then R¹ is other than an optionally substituted phenyl; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

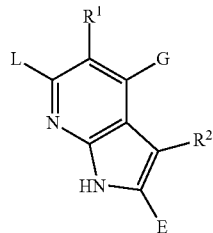

wherein R¹ is optionally substituted carbocyclyl or heterocyclyl group, R² is an optionally substituted five or six membered heterocyclyl group or an optionally substituted six membered carbocyclyl group, E is hydrogen, halogen cyano, C₁₋₆ alkoxy or C₁₋₆ alkyl, G is hydrogen, halogen, cyano, C₁₋₆ alkoxy or C₁₋₆ alkyl, and L is hydrogen, halogen, cyano, C₁₋₆ alkoxy or C₁₋₆ alkyl; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

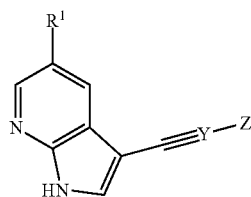

wherein R¹ is an optionally substituted C₃₋₁₆ carbocyclyl or C₃₋₁₂ heterocyclyl group, Y is N or C and Z is lone electron pair, hydrogen, C₁₋₁₂ alkyl, C₂₋₁₂ alkenyl, C₂₋₁₂ alkynyl, C₁₋₁₂ haloalkyl, C₃₋₁₂ carbocyclyl, C₃₋₁₂ heterocyclyl, —(CH₂)ₙOR², —(CH₂)ₙNR²₂, —CO₂R², —COR², —CONR²₂, wherein the C₁₋₁₂ alkyl group optionally contains one or more insertions selected from —O—, —N(R²)—, —SO—, —SO₂—; and each substitutable nitrogen atom in Z is optionally substituted by —R³, —COR³, —SO₂R³ or —CO₂R³; wherein n is 1 to 6, preferably n is 1, 2, or 3; wherein R² is hydrogen, C₁₋₁₂ alkyl, C₃₋₁₆ carbocyclyl or C₃₋₁₂ heterocyclyl, C₁₋₁₂ alkylC₃₋₁₆ carbocyclyl, or C₁₋₁₂ alkylC₃₋₁₂ heterocyclyl optionally substituted by one or more of C₁₋₆ alkyl, halogen, C₁₋₆ haloalkyl, —OR⁴, —SR⁴, —NO₂, CN, —NR⁴R⁴, —NR⁴COR⁴, —NR⁴CONR⁴R⁴, —NR⁴CO₂R⁴, —CO₂R⁴, —COR⁴, —CONR⁴₂, —SO₂R⁴, —SONR⁴₂, —SO₂NR⁴R⁴, —NR⁴SO₂R⁴, wherein the C₁₋₁₂ alkyl group optionally incorporates on or two insertions selected for the group consisting of —O—, —N(R⁴)—, —S—, —SO—, —SO₂—, wherein each R⁴ may be the same or different and is defined below; wherein two R² and NR²₂ may form a partially saturated, unsaturated or fully saturated five to seven membered ring containing one to three heteroatoms, optionally and independently substituted with one or more halogen, C₁₋₁₂ alkyl, C₂₋₁₂ alkenyl, C₂₋₁₂ alkynyl, C₁₋₁₂ haloalkyl, C₃₋₁₂ carbocyclyl, C₃₋₁₂ heterocyclyl, —OR⁵, —SR⁵, —NO₂, CN, —NR⁵R⁵, —NR⁵COR⁵, —NR⁵CONR⁵R⁵, —NR⁵CO₂R⁵, —CO₂R⁵, —COR⁵, —CONR⁵₂, —SO₂R⁵, —SONR⁵₂, —SOR⁵, —SO₂NR⁵R⁵, —NR⁵SO₂R⁵; and each saturated carbon in the optional ring is further optionally and independently substituted by =O, =S, NNR⁶₂, =N—OR⁶, =NNR⁶COR⁶, =NNR⁶CO₂R⁶, =NNSO₂R⁶, or =NR⁶; wherein R³ is hydrogen, C₁₋₆ alkyl, C₁₋₆ haloalkyl, or C₆₋₁₂ aryl; wherein R⁴ is hydrogen, C₁₋₆ alkyl, C₁₋₆ haloalkyl, or C₆₋₁₂ aryl; wherein R⁵ is hydrogen, C₁₋₁₂ alkyl, C₃₋₁₆ carbocyclyl or C₃₋₁₂ heterocyclyl, optionally substituted by one or more of C₁₋₆ alkyl, halogen, C₁₋₆ haloalkyl, —OR⁷, —SR⁷, —NO₂, CN, —NR⁷R⁷, —NR⁷COR⁷, —NR⁷CONR⁷R⁷, —NR⁷CO₂R⁷, —CO₂R⁷, —COR', —CONR⁷₂, —SO₂R⁷, —SONR⁷₂, —SOR⁷, —SO₂NR⁷R⁷, —NR⁷SO₂R⁷; wherein the C₁₋₁₂ alkyl group optionally incorporates one or two insertions selected from the group consisting of —O—, —N(R⁷)—, —SO—, —SO₂—, wherein each R⁷ may be the same or different and is defined below; wherein R⁶ is hydrogen, C₁₋₁₂ alkyl, C₃₋₁₆ carbocyclyl or C₃₋₁₂ heterocyclyl, optionally substituted by one or more of C₁₋₆ alkyl, halogen, C₁₋₆ haloalkyl, —OR⁷, —SR⁷, —NO₂, CN, —NR⁷R⁷, —NR⁷COR⁷, —NR⁷CONR⁷R⁷, —NR⁷CO₂R⁷, —CO₂R⁷, —COR⁷, —CONR⁷₂, —SO₂R⁷, —SONR⁷₂, —SOR⁷, —SO₂NR⁷R⁷, —NR⁷SO₂R⁷; wherein the C₁₋₁₂ alkyl group optionally incorporates one or two insertions selected from the group consisting of —O—, —N(R⁷)—, —S—, —SO—, —SO₂—, wherein each R⁷ may be the same or different and is defined below; wherein R⁷ is hydrogen, C₁₋₆ alkyl, or C₁₋₆ haloalkyl; wherein the optionally substituted carbocyclyl or heterocyclyl group in R¹ and Z is optionally and independently fused to a partially saturated, unsaturated or fully saturated five to seven membered ring containing zero to three heteroatoms, and each substitutable carbon atom in R¹ or Z, including the optional fused ring, is optionally and independently substituted by one or more of halogen, C₁₋₁₂ alkyl, C₂₋₁₂ alkenyl, C₂₋₁₂ alkynyl, C₁₋₁₂ haloalkyl, C₃₋₁₂ carbocyclyl, C₃₋₁₂ heterocyclyl, —(CH₂)ₙOR¹², —(CH₂)ₙNR¹²₂, —OR¹², —SR¹², —NO₂, CN, —NR¹²R¹², —NR¹²COR¹², —NR¹²CONR¹²R¹², —NR¹²CO₂R¹², —CO₂R¹², —COR¹², —CONR¹²₂, —SO₂R¹², —SONR¹²₂, —SOR¹², —SO₂NR¹²R¹², —NR¹²SO₂R¹²; wherein the C₁₋₁₂ alkyl group optionally contains one or more insertions selected from —O—, —N(R¹²)—, —SO—, —SO₂—, and each saturated carbon in the optionally fused ring is further optionally and independently substituted by =O, =S, $NNR^{13}{}_2$, =N—$OR^{13}$, =$NNR^{13}COR^{13}$, =$NNR^{13}CO_2R^{13}$, =$NNSO_2R^{13}$, or =$NR^{13}$; and each substitutable nitrogen atom in $R^1$ is optionally substituted by —$R^{14}$, —$COR^{14}$, —$SO_2R^{14}$, or —$CO_2R^{14}$; wherein n is 1 to 6, preferably n is 1, 2, or 3; wherein $R^{12}$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, —$OR^{15}$, —$SR^{15}$, —$NO_2$, CN, —$NR^{15}R^{15}$, —$NR^{15}COR^{15}$, —$NR^{15}CONR^{15}R^{15}$, —$NR^{15}CO_2R^{15}$, —$CO_2R^{15}$, —$COR^{15}$, —$CONR^{15}{}_2$, —$SO_2R^{15}$, —$SONR^{15}{}_2$, —$SOR^{15}$, —$SO_2NR^{15}R^{15}$, —$NR^{15}SO_2R^{15}$; wherein the $C_{1-12}$ alkyl group optionally incorporates one or two insertions selected from the group consisting of —O—, —N($R^{15}$)—, —S—, —SO—, —$SO_2$—, wherein each $R^7$ may be the same or different and is defined below; wherein two $R^{12}$ and $NR^{12}{}_2$ may form a partially saturated, unsaturated or fully saturated five to seven membered ring containing one to three heteroatoms, optionally and independently substituted with one or more halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, —$OR^{16}$, —$SR^{16}$, —$NO_2$, CN, —$NR^{16}R^{16}$, —$NR^{16}COR^{16}$, —$NR^{16}CONR^{16}R^{16}$, —$NR^{16}CO_2R^{16}$, —$CO_2R^{16}$, —$COR^{16}$, —$CONR^{16}{}_2$, —$SO_2R^{16}$, —$SONR^{16}{}_2$, —$SOR^{16}$, —$SO_2NR^{16}R^{16}$, —$NR^{16}SO_2R^{16}$; and each saturated carbon in the optional ring is further optionally and independently substituted by =O, =S, $NNR^{17}{}_2$, =N—$OR^{17}$, =$NNR^{17}COR^{17}$, =$NNR^{17}CO_2R^{17}$, =$NNSO_2R^{17}$, or =$NR^{17}$; wherein $R^{13}$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, —$OR^{15}$, —$SR^{15}$, —$NO_2$, CN, —$NR^{15}R^{15}$, —$NR^{15}COR^{15}$, —$NR^{15}CONR^{15}R^{15}$, —$NR^{15}$—$CO_2R^{15}$—, —$CO_2R^{15}$, —$COR^{15}$, —$CONR^{15}{}_2$, —$SO_2R^{15}$, —$SONR^{15}{}_2$, —$SOR^{15}$, —$SO_2NR^{15}R^{15}$, —$NR^{15}SO_2R^{15}$; wherein the $C_{1-12}$ alkyl group optionally incorporates one or two insertions selected from the group consisting of —O—, —N($R^{15}$)—, —S—, —SO—, —$SO_2$—, wherein each $R^{15}$ may be the same or different and is defined below; wherein $R^{14}$ is hydrogen, $C_{1-6}$ alkyl, $C_{1-6}$ haloalkyl, or $C_{6-12}$ aryl; wherein $R^{15}$ is hydrogen, $C_{1-6}$ alkyl, $C_{1-6}$ haloalkyl; wherein $R^{16}$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, —$OR^{18}$, —$SR^{18}$, —$NO_2$, CN, —$NR^{18}R^{18}$, —$NR^{18}COR^{18}$, —$NR^{18}CONR^{18}R^{18}$, —$NR^{18}CO_2R^{18}$, —$CO_2R^{18}$, —$COR^{18}$, —$CONR^{18}{}_2$, —$SO_2R^{18}$, —$SONR^{18}{}_2$, —$SOR^{18}$, —$SO_2NR^{18}R^{18}$, —$NR^{18}SO_2R^{18}$; wherein the $C_{1-12}$ alkyl group optionally incorporates one or two insertions selected from the group consisting of —O—, —N($R^{18}$)—, —S—, —SO—, —$SO_2$—, wherein each $R^{18}$ may be the same or different and is defined below; wherein $R^{17}$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, —$OR^{18}$, —$SR^{18}$, —$NO_2$, CN, —$NR^{18}CONR^{18}R^{18}$, —$NR^{18}CO_2R^{18}$, —$CO_2R^{18}$, —$COR^{18}$, —$CONR^{18}{}_2$, —$SO_2R^{18}$, —$SONR^{18}{}_2$, —$SOR^{18}$, —$SO_2NR^{18}R^{18}$, —$NR^{18}SO_2R^{18}$; wherein the $C_{1-12}$ alkyl group optionally incorporates one or two insertions selected from the group consisting of —O—, —N($R^{18}$)—, —S—, —SO—, —$SO_2$—, wherein each $R^{18}$ may be the same or different and is defined below; wherein $R^{18}$ is hydrogen, $C_{1-6}$ alkyl, $C_{1-6}$ haloalkyl; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

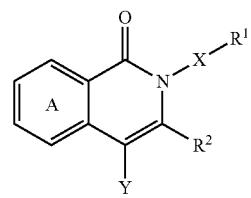

wherein ring A is an optionally substituted benzene ring, X is —O—, —N=, —$NR^3$— or —$CHR^3$—, $R^2$ is an acyl group, an optionally esterified or thioesterified carboxyl group, and optionally substituted carbamoyl group or an optionally substituted amino group and the line, a broken line shows a single bond or a double bond, and $R^1$ is a hydrogen atom, optionally substituted hydrocarbon group, and optionally substituted heterocyclic group and the like; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

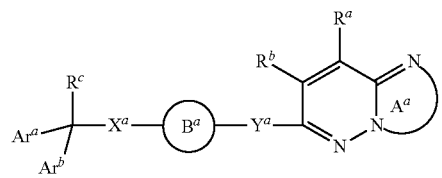

wherein each of $Ar^a$ and $Ar^b$ is an aromatic group optionally having substituents, $Ar^a$ and $Ar^b$ optionally form a condensed cyclic group together with the adjacent carbon atom; ring $B^a$ is a nitrogen-containing heterocycle optionally having substituents; $X^a$ and $Y^a$ are the same or different and each is (1) a bond, (2) an oxygen atom, (3) $S(O)_p$ (wherein p is an integer of 0 to 2), (4) $NR^d$ (wherein $R^d$ is a hydrogen atom or a lower alkyl group) or (5) a divalent linear lower hydrocarbon group optionally having substituents and containing 1 to 3 hetero atom(s); ring $A^a$ is a 5-membered ring optionally having substituents; $R^a$ and $R^b$ are the same or different and each is (1) a hydrogen atom, (2) a halogen atom, (3) a hydrocarbon group optionally having substituents, (4) an acyl group or (5) a hydroxy group optionally having a substituent; $R^c$ is (1) a hydrogen atom, (2) a hydroxy group optionally substituted by a lower alkyl group or (3) a carboxyl group; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

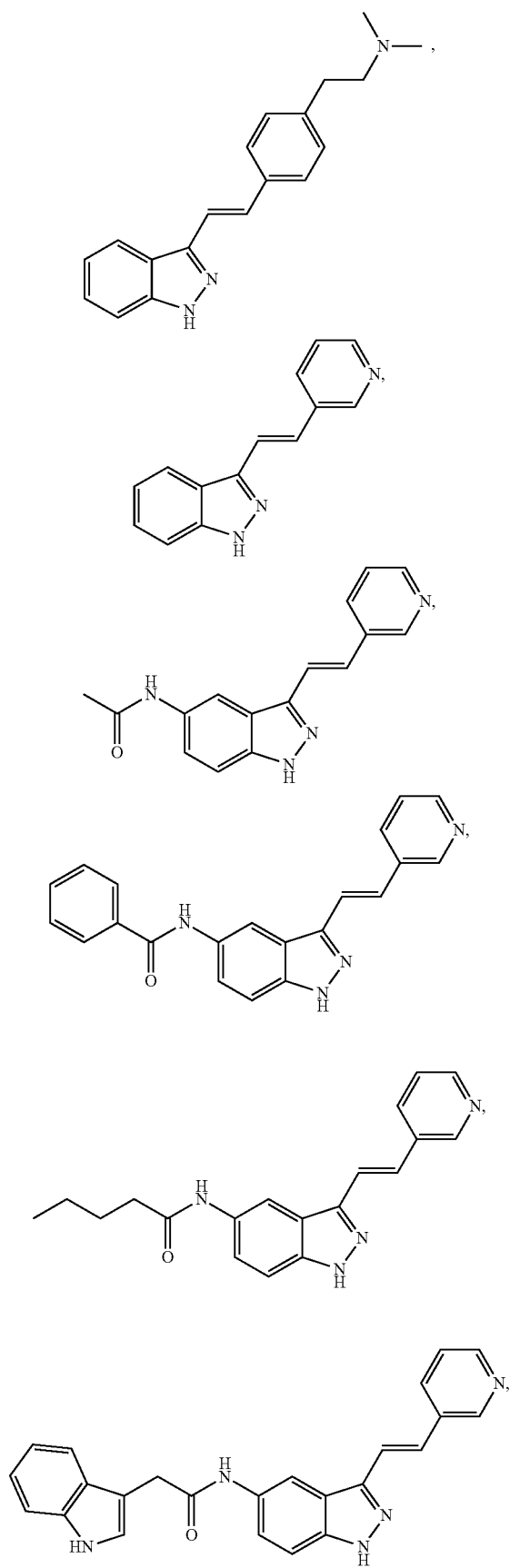
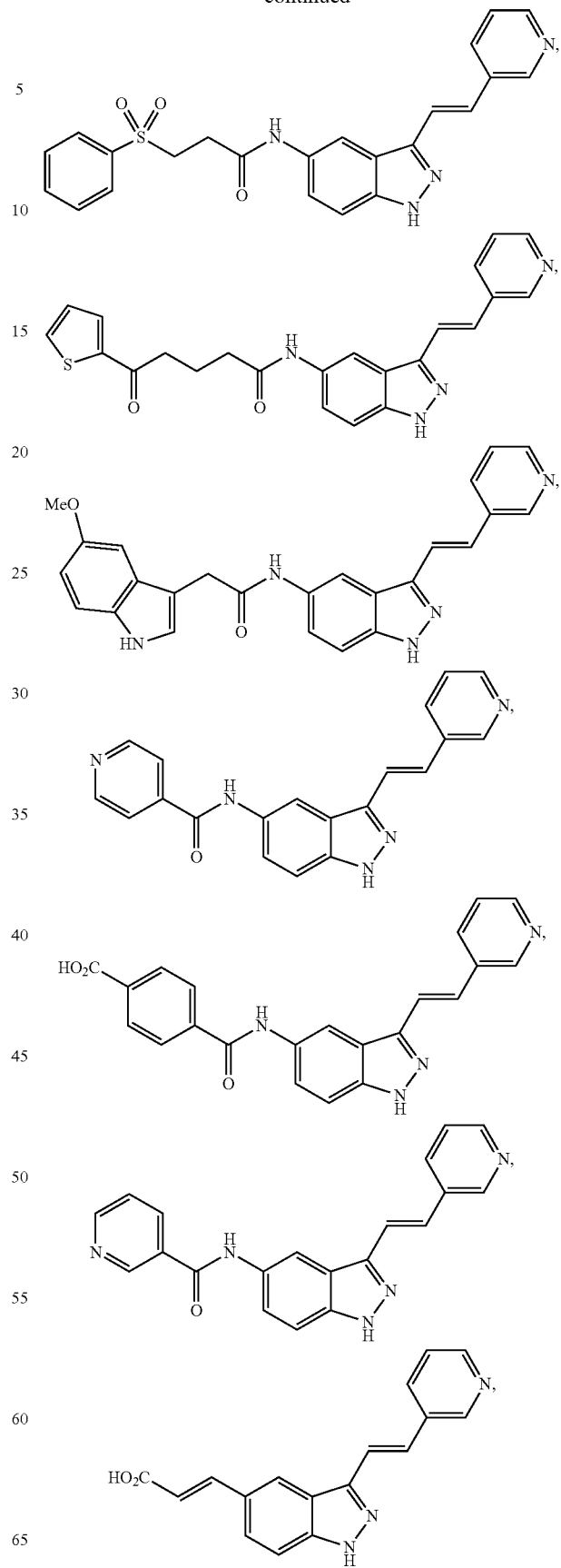

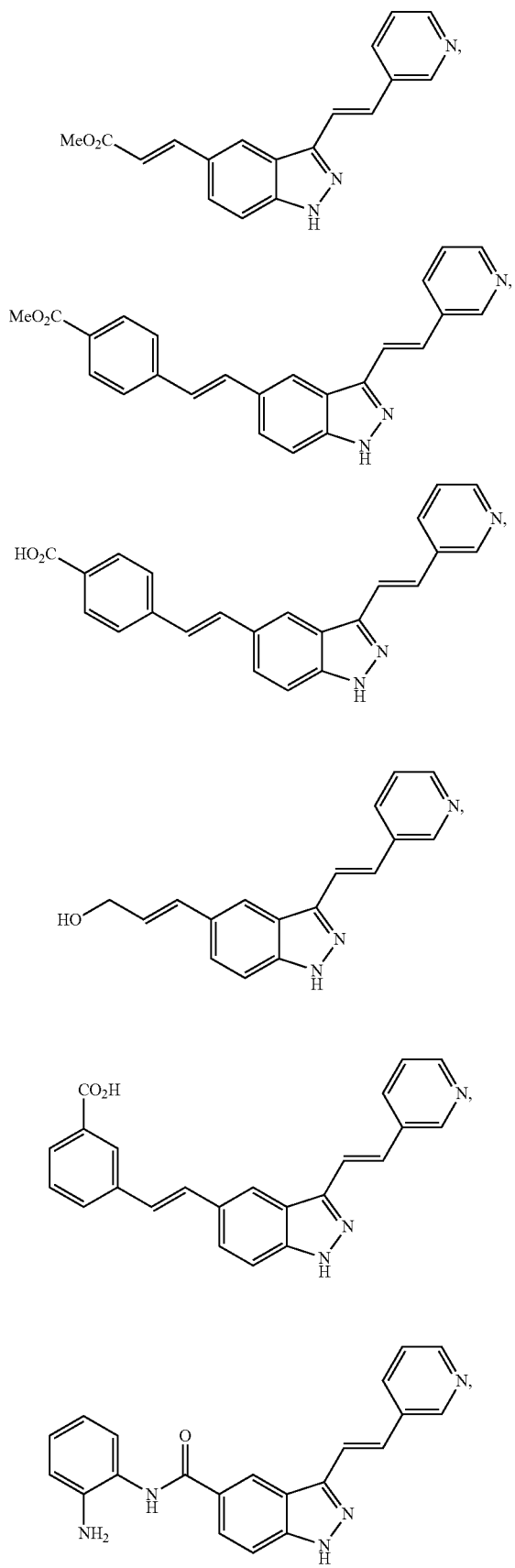

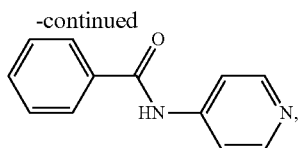

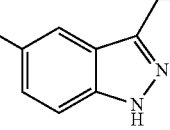

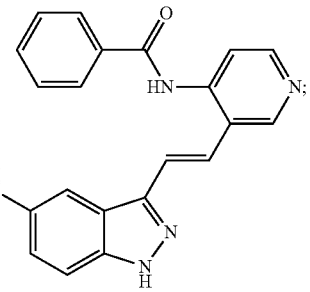

that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

wherein Y is selected from O, NH, N(R), S, S(O) or $S(O)_2$; X is selected from O, NH or N(R); $R^1$ and $R^2$ are each independently selected from H, a $C_1$-$C_6$ straight chain or branched alkyl or alkenyl group, optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)2NH_2$, $S(O)_2NHR$ or R; a 5-7 membered aromatic or non-aromatic carbocyclic or heterocyclic ring, optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NH_2$, $S(O)_2NHR$ or R; or a 9-10 membered bicyclic aromatic or non-aromatic carbocyclic or heterocyclic ring optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NH_2$, $S(O)_2NHR$ or R; wherein said heterocyclic ring contains 1 to 4 heteroatoms, each of which heteroatoms are independently selected from N, O, S, SO or $SO_2$; and R is selected from a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

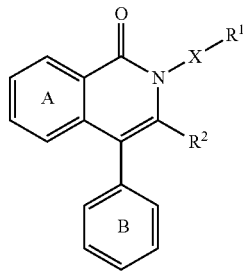

wherein ring A and ring B are each an optionally substituted benzene ring, X is —O—, —N=, —NR$^3$— or —CHR$^3$—, R$^2$ is an acyl group, an optionally esterified or thioesterified carboxyl group, and optionally substituted carbamoyl group or an optionally substituted amino group and the line, a broken line shows a single bond or a double bond, and R$^1$ is a hydrogen atom, optionally substituted hydrocarbon group, and optionally substituted heterocyclic group and the like; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

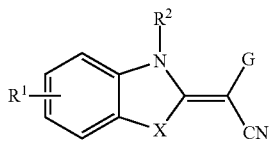

wherein X is O, S or NR$^0$, with R$^0$ being H or an unsubstituted or substituted C$_1$-C$_6$alkyl; G is an unsubstituted or substituted pyrimidinyl group; R$^1$ is selected from the group comprising or consisting of hydrogen, unsubstituted or substituted C$_1$-C$_6$-alkoxy, unsubstituted or substituted C$_1$-C$_6$-thioalkoxy, unsubstituted or substituted C$_1$-C$_6$-alkyl, unsubstituted or substituted C$_2$-C$_6$-alkenyl unsubstituted or substituted C$_2$-C$_6$-alkynyl, primary, secondary or tertiary amino groups, aminoacyl, aminocarbonyl, unsubstituted or substituted C$_1$-C$_6$ alkoxycarbonyl unsubstituted or substituted aryl, unsubstituted or substituted heteroaryl, carboxyl, cyano, halogen, hydroxy, nitro, sulfoxy, sulfonyl sulfonamide, unsubstituted or substituted hydrazides; R$^2$ is selected from the group comprising or consisting of hydrogen, unsubstituted or substituted C$_1$-C$_6$-alkyl, unsubstituted or substituted C$_2$-C$_6$-alkenyl, unsubstituted or substituted C$_2$-C$_6$-alkynyl, unsubstituted or substituted C$_1$-C$_6$-alkyl-aryl, unsubstituted or substituted aryl or heteroaryl unsubstituted or substituted C$_1$-C$_6$-alkyl-heteroaryl, —C(O)—OR$^3$, —C(O)—R$^3$, —C(O)—NR$^3$R$^{3'}$, —(SO$_2$)R$^3$, with R$^3$ and R$^{3'}$ being independently selected from the group comprising or consisting of hydrogen, unsubstituted or substituted C$_1$-C$_6$alkyl, unsubstituted or substituted C$_2$-C$_6$alkenyl, unsubstituted or substituted C$_2$-C$_6$alknyl, unsubstituted or substituted aryl, unsubstituted or substituted heteroaryl, unsubstituted or substituted C$_1$-C$_6$-alkyl aryl, unsubstituted or substituted C$_1$-C$_6$-alkyl heteroaryl; that inhibits the activity of JNK2 in the subject. In further embodiments; the compound has a minimal effect on the enzymatic activity of JNK1.

In another embodiment, the invention is a method of treating type I diabetes in a subject, comprising administering a compound of the following formula:

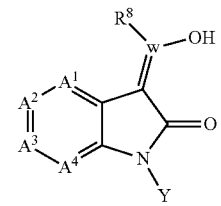

or

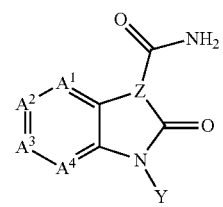

wherein Y is selected from —(CH$_2$)-Q$^1$; —(CO)-Q$^1$; —(CO)NH-Q$^1$; —(CO)—O-Q$^1$; —(SO$_2$)-Q$^1$ or —(SO$_2$)NH-Q$^1$; Q$^1$ is a C$_1$-C$_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring system, wherein said alkyl, alkenyl, ring or ring system is optionally substituted with one to four substituents, each of which is independently selected from NH$_2$, NH—R, N(R)$_2$, NO$_2$, OH, OR, CF$_3$, halo, CN, CO$_2$H, C(O)—NH$_2$, C(O)—NH—R, C(O)—N(R)$_2$, C(O)—R, SR, S(O)—R, S(O)$_2$—R, S(O)$_2$—NH—R or —R; W is N or C; wherein when W is N, R$^8$ is a lone pair of electrons; and wherein when W is C, R$^8$ is R$^7$. A$^1$ is N or CR$^1$; A$^2$ is N or CR$^2$; A$^3$ is N or CR$^3$; A$^4$ is N or CR$^4$; provided that at least one of A$^1$, A$^2$, A$^3$ and A$^4$ must not be N; R$^1$ is —NHR$^5$, —OR$^5$, —SR$^5$, or —R$^5$; R$^2$, R$^3$, and R$^4$ are independently selected from —(CO)NH$_2$, —(CO)NHR, —(CO)N(R)$_2$, —NHR$^5$, —NHCH$_2$R$^5$, —OR$^5$, —SR$^5$, —R$^5$, —NH(CO)—R$^6$, —NH(CO)—NHR$^6$, —NH(CO)—NH(CO)R$^6$, —NH(CO)—OR$^6$, —NH(SO$_2$)—R$^6$, —NH(SO$_2$)—NHR$^6$, —C(O)OH, —C(O)OR, —(CO)-Q$^1$, —(CO)NH-Q$^1$, —(CO)NR-Q$^1$, —(CO)—O-Q$^1$, —(SO$_2$)-Q$^1$ or —(SO$_2$)NH-Q$^1$; R$^5$ and R$^6$ are each independently selected from H; N(R)$_2$, NHOH, NO$_2$, C(O)OR or halo; a C$_1$-C$_6$ straight chain or branched alkyl, alkenyl or alkynyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from NH$_2$, NHR, NHC(O)OR, N(R)$_2$, NO$_2$, OH, OR, CF$_3$, halo, CN, Si(R)$_3$, CO2H, COOR, CONH$_2$, CONHR, CON(R)$_2$, COR, SR, S(O)R, S(O)$_2$R, S(O)$_2$NHR or R; R$^7$ is H; a C$_1$-C$_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, $NHR$, $N(R)_2$, $NO_2$, $OH$, $OR$, $CF_3$, halo, $CN$, $CO_2H$, $CONH_2$, $CONHR$, $CON(R)_2$, $COR$, $SR$, $S(O)R$, $S(O)_2R$, $S(O)_2NHR$ or R; R is a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system; and Z is CH or N; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

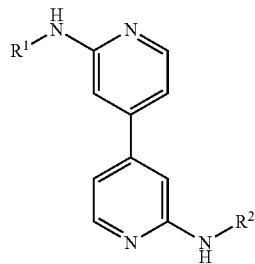

wherein: $R^1$ is aryl or heteroaryl, each of which is optionally substituted with one or more of $R^3$, $OR^3$, $OCOR^3$, $COOR^3$, $COR^3$, $CON^4R^3R^4$, $NHCOR^3$, $NR^3R^4$, $NHSO_2R^3$, $SO_2R^3$, $SO_2NR^3R^4$, $SR^3$, CN, halogen, and $NO_2$; $R^2$ is $R^5$, $R^6$, $COR^5$, $COR^5$, $CONHR^5$, $CONHR^6$, $CON(R^6)_2$, $COOR^5$, $COOR^6$, $SO^2R^5$ or $SO_2R^6$; R3 and R4 are each independently hydrogen, $C_{1-6}$ alkyl, $C_{2-6}$ alkenyl, $C_{2-6}$ alkynyl, $C_{3-8}$ cycloalkyl, ($C_{3-8}$ cycloalkyl) $C_{1-6}$ alkyl, heterocycle, heterocycle $C_{1-6}$ alkyl, $C_{1-6}$ fluoroalkyl, $C_{1-6}$ trifluoroalkoxy; $R^5$ is aryl or heteroaryl, each of which is optionally substituted with one or more of $R^7$, $OR^7$, $OCOR^7$, $COOR^7$, $COR^7$, $CONR^7R^8$, $CONHOR^7$, $NHCOR^7$, $NR^7R^8$, $NHSO_2R^7$, $SO_2R^7$, $SO_2NHR^7R^8$, $SR^7$, $R^7SR^8$, CN, halogen, oxygen and $NO_2$; $R^6$ is hydrogen, $C_{1-6}$ alkyl, $C_{3-8}$ cycloalkyl, ($C_{3-8}$ cycloalkyl) $C_{1-6}$ alkyl, heterocycle, heterocycle $C_{1-6}$ alkyl, heteroaryl $C_{1-6}$ alkyl, aryl $C_{1-6}$ alkyl, $C_{1-6}$ alkoxy, or $C_{2-6}$ alkenyl, wherein any of $C_{1-6}$ alkyl, $C_{3-8}$ cycloalkyl, ($C_{3-8}$ cycloalkyl) $C_{1-6}$ alkyl, heterocycle, heterocycle $C_{1-6}$ alkyl, heteroaryl $C_{1-6}$ alkyl, aryl $C_{1-6}$ alkyl, $C_{1-6}$ alkoxy and $C_{2-6}$ alkenyl is optionally substituted with one or more A; $R^7$ and $R^8$ are each independently hydrogen, $C_{1-6}$ alkyl, $C_{3-8}$ cycloalkyl, ($C_{3-8}$ cycloalkyl) $C_{1-6}$ alkyl, $C_{2-6}$ alkenyl, aryl, heteroaryl, heteroaryl $C_{1-6}$ alkyl, heterocycle, heterocycle $C_{1-6}$ alkyl, aryl, $C_{1-6}$ fluoroalkyl and $C_{1-6}$ chloroalkyl, wherein any of $C_{1-6}$ alkyl, $C_{3-8}$ cycloalkyl, ($C_{3-8}$ cycloalkyl) $C_{1-6}$ alkyl, $C_{2-6}$ alkenyl, heteroaryl, heteroaryl $C_{1-6}$ alkyl, heterocycle and heterocycle $C_{1-6}$ alkyl is optionally substituted with one or more B; $R^9$ and $R^{10}$ are each independently hydrogen, $C_{1-6}$ alkyl, $C_{3-8}$ cycloalkyl, ($C_{3-8}$ cycloalkyl) $C_{1-6}$ alkyl, $C_{2-6}$ alkenyl, heterocycle, heterocycle $C_{1-6}$ alkyl, heteroaryl, heteroaryl $C_{1-6}$ alkyl, aryl or aryl $C_{1-6}$ alkyl, wherein any of $C_{1-6}$ alkyl, $C_{3-8}$ cycloalkyl, ($C_{3-8}$ cycloalkyl) $C_{1-6}$ alkyl, $C_{2-6}$ alkenyl, heterocycle, heterocycle $C_{1-6}$ alkyl, heteroaryl, heteroaryl $C_{1-6}$ alkyl, aryl or aryl $C_{1-6}$ alkyl is optionally substituted with one or more B; A is $R^9$, $OR^9$, $OCOR^9$, $COOR^9$, $COR^9$, $CONR^9R^{10}$, $CONHOR^9$, $NHCOR^9$, $NR^9R^{10}$, $NR^9SO_2R^{10}$, $SO_2R^9$, $SO_2NR^9R^{10}$, $SR^9$, $R^9SR^{10}$, CN or halogen; B is $C_{1-6}$ alkyl, $C_{1-6}$ alkoxy, $C_{1-6}$ alkylamino, di ($C_{1-6}$ alkyl)amino or halogen; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

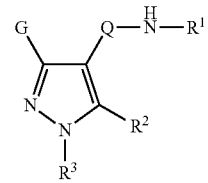

wherein: $R^1$ is selected from hydrogen, $CONH_2$, $T_{(n)}$-R, or $T_{(n)}$-$Ar^1$; R is an aliphatic or substituted aliphatic group; n is zero or one; T is C(=O), $CO_2$, CONH, $S(O)_2$, $S(O)_2NH$, $COCH_2$ or $CH_2$; $R_2$ is selected from hydrogen, —R, —$CH_2OR$, —$CH_2OH$, —CH=O, —$CH_2SR$, —$CH_2S(O)_2R$, —$CH_2(C=O)R$, —$CH_2CO_2R$, —$CH_2CO_2H$, —$CH_2CN$, —$CH_2NHR$, —$CH_2N(R)_2$, —CH=N—OR, —CH=NNHR, —CH=NN(R)_2, —CH=NNHCOR, —CH=NNHCO_2R, —CH=NNHSO_2R, -aryl, —$CH_2$(aryl), —$CH_2NH_2$, —$CH_2NHCOR$, —$CH_2NHCONHR$, —$CH_2NHCON(R)_2$, —$CH_2NRCOR$, —$CH_2NHCO_2R$, —$CH_2CONHR$, —$CH_2CON(R)_2$, —$CH_2SO_2NH_2$, —$CH_2$(heterocyclyl), or —(heterocyclyl); $R^3$ is selected from hydrogen, —R, hydroxyalkyl, alkoxyalkyl, alkylthioalkyl, aminoalkyl, alkylaminoalkyl, dialkylaminoalkyl, heterocyclyl, heterocyclylalkyl; aryl, arylalkyl, or aryloxyalkyl; G is hydrogen or $C_{1-3}$ alkyl; Q-NH is

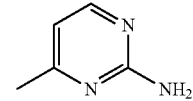

wherein the H of Q-NH is optionally replaced by R, COR, $S(O)_2R$, or $CO_2R$; A is N or CH; $Ar^1$ is aryl, substituted aryl, heterocyclyl or substituted heterocyclyl, wherein $Ar^1$ is optionally fused to a partially unsaturated or fully unsaturated five to seven membered ring containing zero to three heteroatoms; wherein each substitutable carbon atom in $Ar^1$, including the fused ring when present, is optionally and independently substituted by halo, R, OR, SR, OH, $NO_2$, CN, $NH_2$, NHR, $N(R)_2$, NHCOR, NHCONHR, NHCON(R)_2, NRCOR, $NHCO_2R$, $CO_2R$, $CO_2H$, COR, CONHR, CON(R)_2, $S(O)_2R$, $SONH_2$, $S(O)R$, $SO_2NHR$, or $NHS(O)_2R$, and wherein each saturated carbon in the fused ring is further optionally and independently substituted by =O, =S, =NNHR, =NNR_2, =N—OR, =NNHCOR, =NNHCO_2R, =NNHSO_2R, or =NR; and wherein each substitutable nitrogen atom in $Ar^1$ is optionally substituted by R, COR, $S(O)_2R$, or $CO_2R$; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

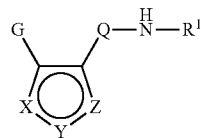

wherein: X—Y—Z is selected from one of the following:

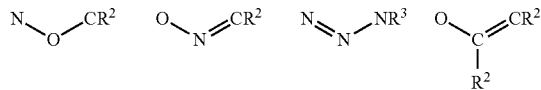

$R^1$ is H, $CONH_2$, $T_{(n)}$-R, or $T_{(n)}$-$Ar^2$; R is an aliphatic or substituted aliphatic group; n is zero or one; T is C(=O), $CO_2$, CONH, $S(O)_2$, $S(O)_2NH$, $COCH_2$ or $CH_2$; each $R^2$ is independently selected from hydrogen, —R, —$CH_2OR$, —$CH_2OH$, —CH=O, —$CH_2SR$, —$CH_2S(O)_2R$, —$CH_2$(C=O)R, —$CH_2CH_2CO_2R$, —$CH_2CO_2H$, —$CH_2CN$, —$CH_2NHR$, —$CH_2N(R)_2$, —H=N—OR, —CH=NNHR, —CH=$NN(R)_2$, —CH=$NNHCOR$, —CH=$NNHCO_2R$, —CH=$NNHSO_2R$, -aryl, -substituted aryl, —$CH_2$(aryl), —$CH_2$(substituted aryl), —$CH_2$ $NH_2$, —$CH_2NHCOR$, —$CH_2NHCONHR$, —$CH_2NHCON(R)_2$, —$CH_2NRCOR$, —$CH_2$ $NHCO_2R$, —$CH_2CONHR$, —$CH_2CON(R)_2$, —$CH_2SO_2NH_2$, —$CH_2$ (heterocyclyl), —$CH_2$ (substituted heterocyclyl), —(heterocyclyl), or —(substituted heterocyclyl); each $R^3$ is independently selected from hydrogen, R, COR, $CO^2R$ or $S(O)^2R$; C is R or $Ar^1$; $Ar^1$ is aryl, substituted aryl, arylalkyl, substituted arylalkyl, heterocyclyl, or substituted heterocyclyl, wherein $Ar^1$ is optionally fused to a partially unsaturated or fully unsaturated five to seven membered ring containing zero to three heteroatoms; Q-NH is

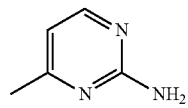

wherein the H of Q-NH is optionally replaced by $R^3$; $Ar^2$ is aryl, substituted aryl, heterocyclyl or substituted heterocyclyl, wherein $Ar^2$ is optionally fused to a partially unsaturated or fully unsaturated five to seven membered ring containing zero to three heteroatoms; wherein each substitutable carbon atom in $Ar^2$, including the fused ring when present, is optionally and independently substituted by halo, R, OR, SR, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, S(O)R, $SONH_2$, S(O)R, $SO_2NHR$, or $NHS(O)_2R$, and wherein each saturated carbon in the fused ring is further optionally and independently substituted by =O, =S, =NNHR, =$NNR_2$, =N—OR, =$NNHCOR$, =$NNHCO_2R$, =$NNHSO_2R$, or =NR; and wherein each substitutable nitrogen atom in $Ar^2$ is optionally substituted by R, COR, $S(O)_2R$, or $CO_2R$; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

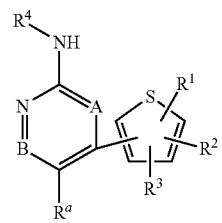

wherein: A and B are each independently selected from N or CH; $R^1$ and $R^2$ are each independently selected from halogen, CN, $NO_2$, $N(R)_2$, OR, SR, or $(T)_n$-$R^5$; $R^3$ is selected from a 3-6 membered carbocyclic or heterocyclic ring having one to two heteroatoms independently selected from nitrogen, oxygen, or sulfur, phenyl, or a 5-6 membered heteroaryl ring having one to three heteroatoms independently selected from nitrogen, oxygen, or sulfur, wherein said phenyl or heteroaryl ring is optionally substituted with one $(T)_n$-Ar and one to two $R^7$; each n is independently selected from zero or one; T is a $C_1$-$C_6$ alkylidene chain, wherein one methylene unit of T is optionally replaced by CO, $CO_2$, COCO, CONR, OCONR, NRNR, NRNRCO, NRCO, $NRCO_2$, NRCONR, $SO_2$, $NRSO_2$, $SO_2NR$, $NRSO_2NR$, O, S, or NR; each R is independently selected from hydrogen or an optionally substituted $C_1$-$C_6$ aliphatic group; or two R on the same nitrogen atom may be taken together with the nitrogen to form a four to eight membered, saturated or unsaturated heterocyclic ring containing one to three heteroatoms independently selected from nitrogen, oxygen, or sulfur; $R^4$ is $(T)_n$-R, $(T)_n$-Ar, or $(T)_n$-$Ar^1$; $R^a$ is selected from $R^b$, halogen, $NO_2$, $OR^b$, $SR^b$, or $N(R^b)_2$; $R^b$ is selected from hydrogen or a $C_1$-$C_4$ aliphatic group optionally substituted with oxo, OH, SH, $NH_2$, halogen, $NO_2$, or CN; $R^5$ is an optionally substituted $C_1$-$C_6$ aliphatic or Ar; Ar is a 5-6 membered saturated, partially unsaturated, or aryl monocyclic ring having zero to three heteroatoms independently selected from nitrogen, sulfur, or oxygen, or an 8-10-membered saturated, partially unsaturated, or aryl bicyclic ring having zero to four heteroatoms independently selected from nitrogen, sulfur, or oxygen, wherein Ar is optionally substituted with one to three $R^7$; $Ar^1$ is a 6-membered aryl ring having zero to two nitrogens, wherein said ring is substituted with one Z—$R^6$ group and optionally substituted with one to three $R^7$; Z is a $C_1$-$C_6$ alkylidene chain wherein up to two non-adjacent methylene units of Z are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; provided that said optionally replaced methylene unit of Z is a methylene unit non-adjacent to $R^6$; $R^6$ is selected from Ar, R, halogen, $NO_2$, CN, OR, SR, $N(R)_2$, NRC(O)R, NRC(O)$N(R)_2$, $NRCO_2R$, C(O)R, $CO_2R$, OC(O)R, C(O)$N(R)_2$, OC(O)$N(R)_2$, SOR, $SO_2R$, $SO_2N(R)_2$, $NRSO_2R$, $NRSO_2N$ $(R)_2$, C(O)C(O)R, or C(O)$CH_2$C(O)R; and each $R^7$ is independently selected from R, halogen, $NO_2$, CN, OR, SR, $N(R)_2$, NRC(O)R, NRC(O)$N(R)_2$, $NRCO_2R$, C(O)R, $CO_2R$, C(O)$N(R)_2$, OC(O)$N(R)_2$, SOR, $SO_2R$, $SO_2N(R)_2$, $NRSO_2R$, $NRSO_2N(R)_2$, C(O)C(O)R, or C(O)$CH_2$C(O)R; or two $R^7$ on adjacent positions of $Ar^1$ may be taken together to form a saturated, partially unsaturated, or fully unsaturated five to seven membered ring containing zero to three heteroatoms selected from O, S, or N; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

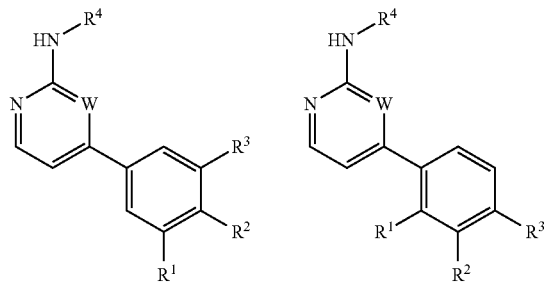

wherein: each W is independently selected from nitrogen or CH; each $R^1$, $R^2$, and $R^3$ is independently selected from halogen, QR, $Q_{(n)}$CN, $Q_{(n)}NO_2$, or $Q_{(n)}$Ar; wherein: $R^1$ and $R^2$ or $R^2$ and $R^3$ are optionally taken together to form a 4-8 membered saturated, partially unsaturated, or fully unsaturated ring having 0-3 heteroatoms independently selected from nitrogen, oxygen, or sulfur; n is zero or one; Q is a $C_{1-4}$ alkylidene chain wherein one methylene unit of Q is optionally replaced by O, S, NR, NRCO, NRCONR, $NRCO_2$, CO, $CO_2$, CONR, OC(O)NR, $SO_2$, $SO_2NR$, $NRSO_2$, $NRSO_2NR$, C(O)C(O), or $C(O)CH_2C(O)$; each R is independently selected from hydrogen or an optionally substituted $C_1$-$C_4$ aliphatic, wherein: two R bound to the same nitrogen atom are optionally taken together with the nitrogen atom to form a 3-7 membered saturated, partially unsaturated, or fully unsaturated ring having 1-2 additional heteroatoms independently selected from nitrogen, oxygen, or sulfur; $R^4$ is $Ar^1$, T-$Ar^2$, or $T_{(n)}$-$Ar^3$; T is a $C_{1-2}$ alkylidene chain wherein one methylene unit of T is optionally replaced by O, NR, NRCO, NRCONR, $NRCO_2$, CO, CO2, CONR, OC(O)NR, $SO_2$, $SO_2NR$, $NRSO_2$, $NRSO_2NR$, C(O)C(O), or $C(O)CH_2C(O)$; $Ar^1$ is a 5-6 membered monocyclic or 8-10 membered bicyclic saturated, partially unsaturated, or fully unsaturated ring system; wherein: Ar1 is optionally substituted with up to five substituents, wherein the first substituent is selected from $R^x$ or $R^5$ and wherein any additional substituents are independently selected from $R^5$; each $R^x$ is independently selected from a 5-6 membered aryl ring having 0-3 heteroatoms selected from nitrogen, oxygen, or sulfur, wherein: $R^x$ is optionally substituted with 1-3 $R^5$; each $R^5$ is independently selected from R, halogen, $NO_2$, CN, OR, SR, $N(R)_2$, NRC(O)R, NRC(O)N(R)$_2$, $NRCO_2R$, C(O)R, $CO_2R$, C(O)N(R)$_2$, OC(O)N(R)$_2$, SOR, $SO_2R$, $SO_2N(R)_2$, $NRSO_2R$, $NRSO_2N(R)_2$, C(O)C(O)R, or $C(O)CH_2C(O)R$; $Ar^2$ is a 5-6 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur; wherein: $Ar^2$ is optionally substituted with up to five substituents, wherein the first substituent is selected from $R^x$ or $R^5$ and wherein any additional substituents are independently selected from $R^5$; $Ar^3$ is a 6-membered aryl ring having 0-2 nitrogens, wherein: $Ar^3$ is substituted with one Z—R group and optionally substituted with 1-3 $R^5$; Z is a $C_1$-$C_6$ alkylidene chain wherein up to two non adjacent methylene units of Z are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and $R^6$ is selected from $Ar^2$, R, halogen, $NO_2$, CN, OR, SR, N(R)$_2$, NRC(O)R, NRC(O)N(R)$_2$, $NRCO_2R$, C(O)R, $CO_2R$, OC(O)R, C(O)N(R)$_2$, OC(O)N(R)$_2$, SOR, $SO_2R$, $SO_2N(R)_2$, $NRSO_2R$, $NRSO_2N(R)_2$, C(O)C(O)R, or $C(O)CH_2C(O)R$; that inhibits the activity of JNK2 in the subject. In further embodiments, the compound has a minimal effect on the enzymatic activity of JNK1.

In another embodiment, the invention is a method of treating type I diabetes in a subject, comprising administering a compound of the following formula:

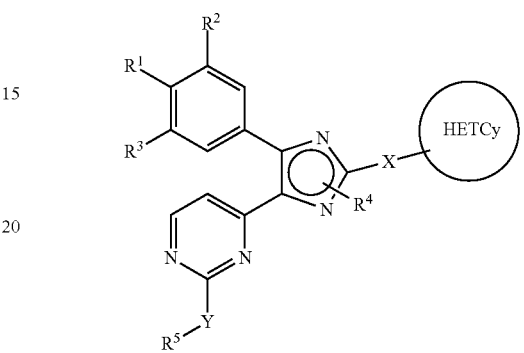

wherein $R^1$ is —F, —Cl, —Br, —OH, —SH, —NH$_2$, or —CH$_3$; $R^2$ is —F, —Cl, —Br—OH, —SH, —NH$_2$, or —CH$_3$; $R^3$ is —H, —F, —Cl, —Br, —OH, —SH, —NH$_2$, —CH$_3$, —OCH$_3$, or —CH$_2$CH$_3$; $R^4$ is —C$_{1-4}$ alkyl optionally substituted with a —C$_{3-7}$ cycloalkyl; $R^5$ is —C$_{1-4}$ alkyl or —C$_{3-7}$ cycloalkyl, wherein the —C$_{1-4}$ alkyl is optionally substituted with a phenyl; X is a bond or an alkyl bridge having 1-3 carbons; Y is —NH— or —NH$_2$+—; and HETCy is a 4 to 10 membered non-aromatic heterocycle containing at least one N atom, optionally containing 1-2 additional N atoms and 0-10 or S atom, and optionally substituted with —C$_{1-4}$ alkyl or —C(O)—O—CH$_2$phenyl; that inhibits the activity of JNK2 in the subject. In further embodiments, the compound has a minimal effect on the enzymatic activity of JNK1.

DEFINITIONS

Figure 1:
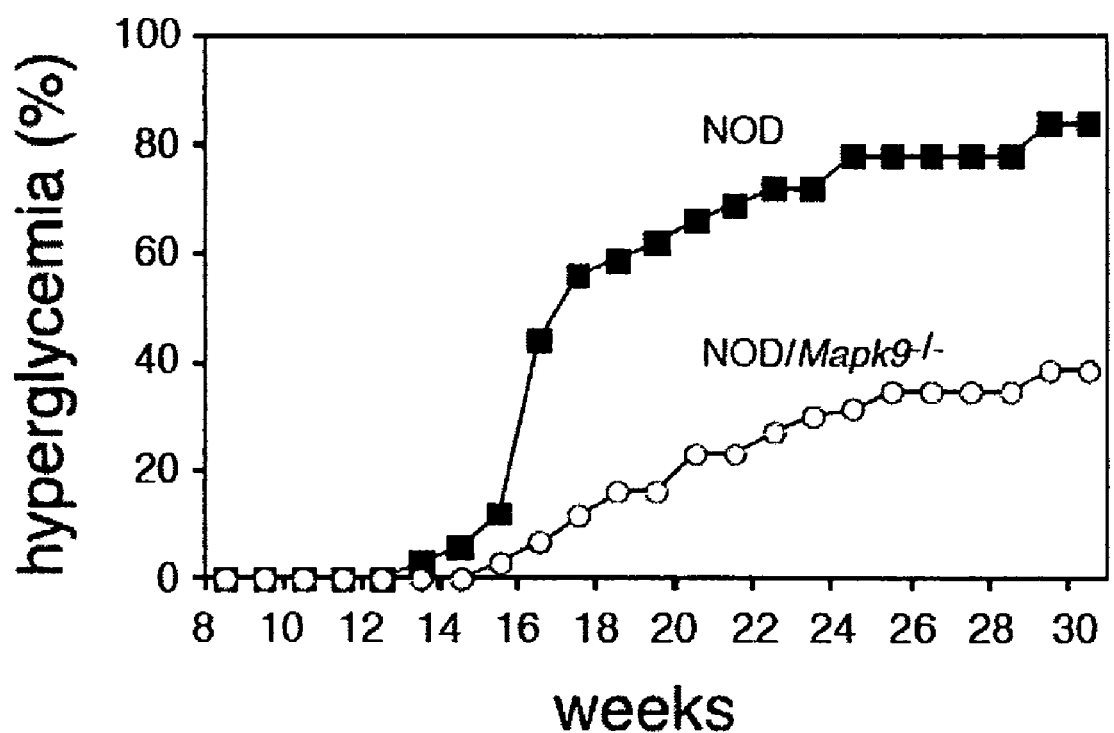
FIG. 1. Spontaneous diabetes is decreased in JNK2-deficient mice. The presence of hyperglycemia (blood glucose >200 mg/dl) was examined in a cohort of 32 NOD mice and 28 female NOD/Mapk9−/− mice. The data are presented as the % of mice with hyperglycemia.

"Acylamino" or "aminoacyl" refers to a group—NR(CO)R' where each R, R' is independently hydrogen or "$C_1$-$C_6$-alkyl" or "aryl" or "heteroaryl" or "aryl $C_1$-$C_6$-alkyl" or "heteroaryl $C_1$-$C_6$-alkyl".

"Acyloxy" means an —OC(O)alkyl group.

"Adverse drug reaction" means any response to a drug that is noxious and unintended and occurs in doses for prophylaxis, diagnosis, or therapy including side effects, toxicity, hypersensitivity, drug interactions, complications, or other idiosyncrasy. Side effects are often adverse symptom produced by a therapeutic serum level of drug produced by its pharmacological effect on unintended organ systems (e.g., blurred vision from anticholinergic antihistamine). A toxic side effect is an adverse symptom or other effect produced by an excessive or prolonged chemical exposure to a drug (e.g., digitalis toxicity, liver toxicity). Hypersensitivities are immune-mediated adverse reactions (e.g., anaphylaxis, allergy). Drug interactions are adverse effects arising from interactions with other drugs, foods or disease states (e.g., warfarin and erythromycin, cisapride and grapefruit, loperamide and *Clostridium difficile* colitis). Complications are diseases caused by a drug (e.g., NSAID-induced gastric ulcer, estrogen-induced thrombosis). The adverse drug reaction may be mediated by known or unknown mechanisms (e.g., Agranulocytosis associated with chloramphenicol or clozapine). Such adverse drug reaction can be determined by an subject observation, assay or animal model well-known in the art.

"Alkyl" means a straight chain or branched, saturated or unsaturated alkyl, cyclic or non-cyclic hydrocarbon having from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butynyl and the like; while representative straight chain and branched alkynyls include acetylenyl, propynyl, 1-butynyl, 2-butynyl, 1-pentynyl, 2-pentynyl, 3-methyl-1-butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

"Alkylamino" means —NH(alkyl).

An "alkenyl group" or "alkylene group" means a monovalent unbranched or branched hydrocarbon chain having one or more double bonds therein. The double bond of an alkenyl group can be unconjugated or conjugated to another unsaturated group. Suitable alkenyl groups include, but are not limited to, ($C_2$-$C_6$) alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted.

"Alkylidene" means the divalent radical—$C_nH_{2n}$—, wherein n is an integer from 1 to 8, such as —$CH_2$—, —$CH_2CH_2$—, —$CH_2$—$CH_2$—$CH_2$—, —$CH_2CH_2CH_2CH_2$—, and the like, unsubstituted or substituted with one or more alkyl groups.

"Alkoxy" refers to a group —O—R where R includes "$C_1$-$C_6$-alyl" or "aryl" or "hetero-aryl" or "aryl $C_1$-$C_6$-alkyl" or "heteroaryl $C_1$-$C_6$-alkyl". Preferred alkoxy groups include by way of example, methoxy, ethoxy, phenoxy and the like.

"Alkoxycarbonyl" refers to a group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl".

"Alkynyl" refers to alkynyl groups preferably having from 2 to 6 carbon atoms and having at least 1-2 sites of alkynyl unsaturation. Examples include ethynyl (—C≡CH), propargyl (—$CH_2$C≡CH), and the like.

"Aminoalkyl" means -(alkyl)-$NH_2$.

"Aminoalkoxy" means —O-(alkyl)-$NH_2$.

"Aminocarbonyl" and the like refers to a group—C(O)NRR' where each R, R' is independently hydrogen or "$C_1$-$C_6$-alkyl" or "aryl" or "heteroaryl" or "aryl $C_1$-$C_6$-alkyl" or "heteroaryl $C_1$-$C_6$-alkyl".

"Aryl" means a carbocyclic or heterocyclic aromatic group containing from 5 to 10 ring atoms. The ring atoms of a carbocyclic aromatic group are all carbon atoms, and include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. A carbocyclic aromatic group can be unsubstituted or substituted. Preferably, the carbocyclic aromatic group is a phenyl group. The ring atoms of a heterocyclic aromatic group contains at least one heteroatom, preferably 1 to 3 heteroatoms, independently selected from nitrogen, oxygen, and sulfur. Illustrative examples of heterocyclic aromatic groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phenyl, isoxazolyl, indolyl, oxetanyl, azepinyl, piperazinyl, morpholinyl, dioxanyl, thietanyl and oxazolyl. A heterocyclic aromatic group can be unsubstituted or substituted. Preferably, a heterocyclic aromatic is a monocyclic ring, wherein the ring comprises 2 to 5 carbon atoms and 1 to 3 heteroatoms.

"Arylamino" means —NH(aryl).

"Arylalkylamino" means —NH-(alkyl)-(aryl), wherein alkyl and aryl are defined above. Preferably, arylalkylamino is —NH-benzyl or —NH$CH_2$-pyridinyl.

"Aryloxy" means —O-aryl group, wherein aryl is as defined above. An aryloxy group can be unsubstituted or substituted. Preferably, the aryl ring of an aryloxy group is a phenyl group "Aryl $C_1$-$C_6$-alkyl" or "Arylalkyl" and the like, refers to $C_1$-$C_6$-alkyl groups, as defined above, having an aryl substituent, including benzyl, phenethyl and the like.

"$C_1$-$C_6$-alkyl" or "$C_{1-6}$-alkyl" and the like refer to monovalent branched or unbranched alkyl groups having 1 to 6 carbon atoms. This term is exemplified by groups such as methyl, ethyl, n-propyl, isopropyl, n-butyl, isobutyl, tert-butyl, n-hexyl and the like.

"$C_2$-$C_6$ Alkenyl" refers to alkenyl groups preferably having from 2 to 6 carbon atoms and having at least 1 or 2 sites of alkenyl unsaturation. Examples include ethenyl (—CH=$CH_2$), n-2-propenyl (allyl, —$CH_2$CH=$CH_2$) and the like.

"$C_3$-$C_6$-cycloalkyl" refers to saturated or partially unsaturated carbocyclic rings having 3 to 6 carbon atoms. Examples include cyclopropyl, cyclobutyl, cyclopentyl, cyclohexyl, cyclohexenyl and the like.

"$C_3$-$C_6$-heterocycloalkyl" refers to saturated or partially unsaturated rings having 3 to 6 atoms and containing at least one heteroatom selected from N, S and O. Examples include pyrrolidinyl, piperidinyl, piperazinyl, imidazolidinyl, morpholinyl and the like.

"Carboxyl" means (—$CO_2H$).

"Carbocyclyl" means a saturated, partly saturated or unsaturated 3-12 membered hydrocarbon ring, preferably a 6-12 membered hydrocarbon ring, including cycloalkyl and aryl.

"Cycloalkylamino" means —NH-(cycloalkyl).

"Cycloalkylalkylamino" means —NH-(alkyl)-(cycloalkyl), wherein alkyl and cycloalkyl are defined above. Preferably, cycloalkylalkylamino is —$NHCH_2$-cyclohexyl.

"Cycloalkyl" means a monocyclic or polycyclic saturated ring comprising carbon and hydrogen atoms and having no carbon-carbon multiple bonds. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

"Di-alkylamino" means —N(alkyl)(alkyl), wherein each "alkyl" is independently an alkyl group "Di-alkylaminoalkyl" means -(alkyl)-N(alkyl)(alkyl), wherein each "alkyl" is independently an alkyl group.

"Di-alkylaminoalkoxy" means —O-(alkyl)N(alkyl)(alkyl), wherein each "alkyl" is independently an alkyl group "Enantiomeric excess" (ee) refers to the products that are obtained by a synthesis comprising an enantioselective step, whereby a surplus of one enantiomer in the order of at least about 52% ee is yielded.

As used herein the phrase "an effective amount" when used in connection with a JNK2 inhibitor means an amount of the JNK2 inhibitor, that produces a measurable change of invasive, destructive, or peri-insulitis by a histological analysis of the pancreas.

"Expression" means the translation or transcription in expressing a gene.

"Halogen" refers to fluoro, chloro, bromo and iodo atoms.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, quinoxalinyl, cinnolinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"Heteroaryl $C_1$-$C_6$-alkyl" and the like refers to $C_1$-$C_6$-alkyl groups having a heteroaryl substituent, including 2-furylmethyl, 2-thienylmethyl, 2-(1H-indol-3-yl)ethyl and the like.

"Heteroatom-containing alkylidene" means an alkylidene wherein at least one carbon atom is replaced by a heteroatom selected from nitrogen, oxygen, or sulfur, such as —$CH_2CH_2OCH_2CH_2$—, and the like, unsubstituted or substituted with one or more alkyl groups.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

"Heterocycloalkyl" means an alkyl having at least one alkyl hydrogen atom replaced with a heterocycle, such as —$CH_2$ morpholinyl, and the like.

"Keto" means a carbonyl group.

"Inhibiting the activity of JNK2" means interacting with a JNK2 protein or natural substrate (e.g. c-jun and JIP-1) to prevent an ordinary biological process (e.g., c-jun phosphorylation) in vitro or in vivo. However, completely preventing the biological process from occurring is not necessary.

The term "JNK2 inhibitor" and the like mean a compound capable of inhibiting the activity of JNK2 in vitro or in vivo. However, complete inhibition is not required. For example, it is sufficient that the inhibitor has an $IC_{50}$ of less than 10 mM in a c-jun phosphorylation assay. The JNK2 inhibitor can be in the form of a pharmaceutically acceptable salt, free-base, solvate, hydrate, stereoisomer, clathrate or prodrug thereof. Such inhibitory activity can be determined by an assay or animal model well known in the art including those set forth in the "detailed description of the invention."

"JNK2" means a protein or an isoform thereof expressed by a JNK2 gene.

As used herein, the term "manage" when used in connection with a disease or condition means to provide beneficial effects to a patient being administered with a prophylactic or therapeutic agent, which does not result in a cure of the disease. In certain embodiments, a patient is administered with one or more prophylactic or therapeutic agents to manage a disease so as to prevent the progression or worsening of the disease.

"Minimal effect" on activity of a protein means a compound has less than half of the same effect on activity compared to another protein. For example, if a compound has an $IC_{50}$ of 1 μM for JNK2 using c-Jun phosphorylation assay as described below, then the compound has minimal effect on the inhibition of JNK1 as long as the $IC_{50}$ for JNK1 in the same assay is greater than 2 μM. Such minimal effect can be determined by an assay or animal model well known in the art including those set forth in the "detailed description of the invention."

"Mono-alkylamino" means —NH(alkyl).

"Mono-alkylaminoalkoxy" means —O-(alkyl)-NH (alkyl), wherein each "alkyl" is independently an alkyl group.

"Mono-alkylaminoalkyl" means -(alkyl)-NH(alkyl), wherein each "alkyl" is independently an alkyl group.

As used herein and unless otherwise indicated, the term "prodrug" means a JNK2 inhibitor derivative that can hydrolyze, oxidize, or otherwise react under biological conditions (in vitro or in vivo) to provide an active compound, particularly a JNK2 inhibitor. Examples of prodrugs include, but are not limited to, derivatives and metabolites of a JNK2 inhibitor that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule.

"Pharmaceutically active derivative" refers to any compound that upon administration to the recipient, is capable of providing directly or indirectly, the activity disclosed herein.

"Pharmaceutically acceptable salts or "complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, poly glutamic, acid, naphthalene sulfonic acid, naphthalene disulfonic acid, and poly galacturonic acid. Said compounds can also be administered as pharmaceutically acceptable quaternary salts known by a person skilled in the art, which specifically include the quaternary ammonium salts of the formula —NR, R',R"$^+$Z$^-$, wherein R, R', R" is independently hydrogen, alkyl, or benzyl, and Z is a counter ion, including chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the terms "prevent" and "preventing" include the prevention of the recurrence, spread or onset of type I diabetes. It is not intended that the present invention be limited to complete prevention. In some embodiments, the onset is delayed, or the severity of the disease is reduced.

As used herein, the term "prophylactic agent" includes any agent that can be used in the prevention of a disease.

"Sulfonyl" refers to a group "—SO$_2$—R" wherein R is selected from H, "aryl", "heteroaryl", "$C_1$-$C_6$-alkyl", "$C_1$-$C_6$-alkyl" which may be substituted with halogens e.g. an —SO$_2$—CF$_3$ group, "aryl $C_1$-$C_6$-alkyl" or "heteroaryl $C_1$-$C_6$-alkyl".

"Sulfoxy" refers to a group "—S(O)—R" wherein R is selected from H, "$C_1$-$C_6$-alkyl", "$C_1$-$C_6$-alkyl" which may be substituted with halogens e.g. an —SO—CF$_3$ group, "aryl", "heteroaryl", "aryl $C_1$-$C_6$-alkyl" or "heteroaryl $C_1$-$C_6$-alkyl".

"Substituted or unsubstituted" unless otherwise constrained by the definition of the individual substituent, the above set out groups, like "alkyl", "Alkenyl", "alkynyl", "aryl" and "heteroaryl" etc. groups can optionally be substituted with from 1 to 5 substituents selected from the group consisting of "$C_1$-$C_6$-alkyl", "aryl $C_1$-$C_6$-alkyl", "heteroaryl $C_1$-$C_6$-alkyl", "$C_1$-$C_6$-alkenyl", "$C_1$-$C_6$-alkynyl", primary, secondary or tertiary amino groups or quaternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when vicinal functional substituents are involved, thus forming e.g. lactams, lactons, cyclic anhydrides, but also acetals, thioacetals, animals formed by ring closure for instance in an effort to obtain a protective group.

"Substituent(s)" of the "hydrocarbon group optionally having substituent(s)", or the like, means to have, oxo (═O), halogen atom (e.g., fluorine, chlorine, bromine, iodine etc.), $C_1$-$C_3$ alkylenedioxy (e.g., methylenedioxy, ethylenedioxy etc.), nitro, cyano, optionally halogenated $C_1$-$C_6$ alkyl, optionally halogenated $C_2$-$C_6$ alkenyl, carboxy $C_2$-$C_6$ alkenyl (e.g., 2-carboxyethenyl, 2-carboxy-2-methylethenyl etc.), optionally halogenated $C_2$-$C_6$ alkynyl, optionally halogenated $C_3$-$C_8$ cycloalkyl, $C_6$-$C_{14}$ aryl (e.g., phenyl, 1-naphthyl, 2-naphthyl, 2-biphenylyl, 3-biphenylyl, 4-biphenylyl, 2-anthryl etc.), optionally halogenated $C_1$-$C_8$ alkoxy, $C_1$-$C_6$ alkoxy-carbonyl-$C_1$-$C_6$ alkoxy (e.g., ethoxycarbonylmethyloxy etc.), hydroxy, $C_6$-$C_{14}$ aryloxy (e.g., phenyloxy, 1-naphthyloxy, 2-naphthyloxy etc.), $C_7$-$C_{16}$ aralkyloxy (e.g.; benzyloxy, phenethyloxy etc.), mercapto, optionally halogenated $C_1$-$C_6$ alkylthio, $C_6$-$C_{14}$ arylthio (e.g., phenylthio, 1-naphthylthio, 2-naphthylthio etc.), $C_7$-$C_{16}$ aralkylthio (e.g., benzylthio, phenethylthio etc.), amino, mono-$C_1$-$C_6$ alkylamino (e.g., methylamino, ethylamino etc.), mono-$C_6$-$C_{14}$ arylamino (e.g., phenylamino, 1-naphthylamino, 2-naphthylamino etc.), di-$C_1$-$C_6$ alkylamino (e.g., dimethylamino, diethylamino, ethylmethylamino etc.), $C_3$-$C_8$ cycloalkylamino (e.g., cyclopentylamino, cyclohexylamino etc.), di-$C_6$-$C_{14}$ arylamino (e.g., diphenylamino etc.), formyl, carboxy, carboxy-$C_1$-$C_6$ alkyl (e.g., carboxymethyl, carboxyethyl etc.), $C_1$-$C_6$ alkyl-carbonyl (e.g., acetyl, propionyl, pivaloyl etc.), $C_3$-$C_8$ cycloalkylcarbonyl (e.g., cyclopropylcarbonyl, cyclopentylcarbonyl, cyclohexylcarbonyl etc.), $C_1$-$C_6$ alkoxy-carbonyl (e.g., methoxycarbonyl, ethoxycarbonyl, propoxycarbonyl, tert-butoxycarbonyl etc.), $C_6$-$C_{14}$ aryl-carbonyl (e.g., benzoyl, 1-naphthoyl, 2-naphthoyl etc.), $C_7$-$C_{16}$ aralkyl-carbonyl (e.g., phenylacetyl, 3-phenylpropionyl etc.), $C_6$-$C_{14}$ aryloxy-carbonyl (e.g., phenoxycarbonyl etc.), $C_7$-$C_{16}$ aralkyloxy-carbonyl (e.g., benzyloxycarbonyl, phenethyloxycarbonyl etc.), 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.), carbamoyl, thiocarbamoyl, mono-$C_1$-$C_6$ alkyl-carbamoyl (e.g., methylcarbamoyl, ethylcarbamoyl etc.), di-$C_1$-$C_6$ alkyl-carbamoyl (e.g., dimethylcarbamoyl, diethylcarbamoyl, ethylmethylcarbamoyl etc.), mono- or di-$C_6$-$C_{14}$ arylcarbamoyl (e.g., phenylcarbamoyl, 1-naphthylcarbamoyl, 2-naphthylcarbamoyl etc.), mono- or di-5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), $C_1$-$C_6$ alkylsulfonyl (e.g., methylsulfonyl, ethylsulfonyl etc.), $C_1$-$C_6$ alkylsulfinyl (e.g., methylsulfinyl, ethylsulfinyl etc.), $C_6$-$C_{14}$ arylsulfonyl (e.g., phenylsulfonyl, 1-naphthylsulfonyl, 2-naphthylsulfonyl etc.), $C_6$-$C_{14}$ arylsulfinyl (e.g., phenylsulfinyl, 1-naphthylsulfinyl, 2-naphthylsulfinyl etc.), formylamino, $C_1$-$C_6$ alkyl-carbonylamino (e.g., acetylamino, propionylamino, pivaloylamino etc.), $C_3$-$C_8$ cycloalkyl-carbonylamino (e.g., cyclopentylcarbonylamino-, cyclohexylcarbonylamino etc.), $C_6$-$C_{14}$ aryl-carbonylamino (e.g., benzoylamino, naphthoylamino etc.), $C_1$-$C_6$ alkoxy-carbonylamino (e.g., methoxycarbonylamino, ethoxycarbonylamino, propoxycarbonylamino, butoxycarbonylamino etc.), $C_1$-$C_6$ alkylsulfonylamino (e.g., methylsulfonylamino, ethylsulfonylamino etc.), $C_6$-$C_{14}$ arylsulfonylamino (e.g., phenylsulfonylamino, 2-naphthylsulfonylamino, 1-naphthylsulfonylamino etc.), $C_1$-$C_6$ alkyl-carbonyloxy (e.g., acetoxy, propionyloxy etc.), $C_6$-$C_{14}$ aryl-carbonyloxy (e.g., benzoyloxy, naphthylcarbonyloxy etc.), $C_1$-$C_6$ alkoxy-carbonyloxy (e.g., methoxycarbonyloxy, ethoxycarbonyloxy, propoxycarbonyloxy, butoxycarbonyloxy etc.), mono-$C_1$-$C_6$ alkylcarbamoyloxy (e.g., methylcarbamoyloxy, ethylcarbamoyloxy etc.), di-$C_1$-$C_6$ alkyl-carbamoyloxy (e.g., dimethylcarbamoyloxy, diethylcarbamoyloxy etc.), mono- or di-$C_6$-$C_{14}$ arylcarbamoyloxy (e.g., phenylcarbamoyloxy, naphthylcarbamoyloxy etc.), nicotinoyloxy, isonicotinoyloxy, 5- to 7-membered saturated cyclic amino optionally having substituents, 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), sulfo, sulfamoyl, sulfinamoyl, sulfenamoyl, a group wherein 2 or more (e.g., 2-3) of these substituents are bonded and the like can be mentioned.

"Selective inhibition" means that the inhibition of protein activity of a compound on one molecular entity has a minimal effect on a second molecular entity.

As used herein in connection with the term "therapeutic agent", "therapeutically effective amount" includes the amount of the therapeutic agent sufficient to delay, reduce or minimize symptoms associated with type I diabetes. A therapeutically effective amount also includes the amount of the therapeutic agent that provides a therapeutic benefit in the treatment or management of type I diabetes.

"Thioalkoxy" refers to groups —S—R where R includes "$C_1$-$C_6$-alkyl" or "aryl" or "heteroaryl" or "aryl $C_1$-$C_6$-alkyl" or "heteroaryl $C_1$-$C_6$-alkyl". Examples include thiomethoxy, thioethoxy, and the like.

As used herein, the term "therapeutic agent" includes any agent(s) that can be used in the treatment of a disease.

As used herein, the terms "treat" and "treating" are not limited to the case where the subject (e.g. patient) is cured and the disease is eradicated. Rather, the present invention also contemplates treatment that merely reduces symptoms, and/or delays disease progression. Thus, in certain embodiments, treatment aids in the management or control of type I diabetes.

DETAILED DESCRIPTION OF THE INVENTION

The invention relates to the treatment and prevention of type I diabetes. More specifically, the invention relates to compounds that treat or prevent the body's immune system from destroying β-cells (i.e., insulin-producing cells in the pancreatic islets of Langerhans) by inhibition of JNK2, selective inhibition of JNK2, or inhibition of the expression of the MAPK9 gene or gene product. In one embodiment, the present invention contemplates the diagnosis, identification, production, and use of compounds which modulate MAPK9 gene expression or the activity of the MAPK9 gene product including but not limited to, JNK2, the nucleic acid encoding MAPK9 and homologues, analogues, and deletions thereof, as well as antisense, ribozyme, triple helix, antibody, and polypeptide molecules as well as small inorganic molecules.

The present invention contemplates a variety of pharmaceutical formulations and routes of administration for such compounds. The pancreas is an organ located behind the lower part of the stomach. It makes insulin and enzymes that help the body digest and use food. Spread all over the pancreas are clusters of cells called the islets of Langerhans. Islets are made up of two types of cells: alpha cells, which make glucagon, a hormone that raises the level of glucose (sugar) in the blood, and beta (β) cells, which make insulin. Failure of the insulin-producing beta cells in the pancreatic islets of Langerhans is a characteristic of type I (insulin-dependent) diabetes.

JNK1, JNK2, and JNK3 c-jun N-terminal protein kinase isoforms comprise a family of serine/threonine protein kinases of the mitogen-activating protein kinase (MAPK) group. As regulators of stress-signaling responses, JNKs play key roles in: tumor suppression, aging, neurogenesis, and immune responses. JNK2 (c-Jun N-terminal knase 2) is also called Stress-activated protein kinase 2 (SAPK2). The JNK2 gene (MAPK9) maps on chromosome 5q35 spanning 58494 base pairs (Accession No. U09759). It contains 17 confirmed introns, 14 of which are alternative. By alternative splicing, JNK2 gene encodes 12 types of transcripts that translate into 12 distinct JNK2 isoforms. The molecular weight of JNK2 is about 55 kD.

JNK1 is a protein comprising the amino acid sequence of GenBank Accession Number: L26318: Sequence Identification Number 1: (M S R S K R D N N F Y S V E I G D S T F T V L K R Y Q N L K P I G S G A Q G I V C A A Y D A I L E R N V A I K K L S R P F Q N Q T H A K R A Y R E L V L M K C V N H K N I I G L L N V F T P Q K S L E E F Q D V Y I V M E L M D A N L C Q V I Q M E L D H E R M S Y L L Y Q M L C G I K H L H S A G I I H R D L K P S N I V V K S D C T L K I L D F G L A R T A G T S F M M T P Y V V T R Y Y R A P E V I L G M G Y K E N V D L W S V G C I M G E M V C H K I L F P G R D Y I D Q W N K V I E Q L G T P C P E F M K K L Q P T V R T Y V E N R P K Y A G Y S F E K L F P D V L F P A D S E H N K L K A S Q A R D L L S K M L V I D A S K R I S V D E A L Q H P Y I N V W Y D P S E A E A P P P K I P D K Q L D E R E H T I E E W K E L I Y K E V M D L E E R T K N G V I R G Q P S P L A Q V Q Q)

In one embodiment, JNK2 is a protein comprising the amino acid sequence of GenBank Accession No. L3195: Sequence Identification Number 2: (M S D S K C D S Q F Y S V Q V A D S T F T V L K R Y Q Q L K P I G S G A Q G I V C A A F D T V L G I S V A V K K L S R P F Q N Q T H A K R A Y R E L V L L K C V N H K N I I S L L N V F T P Q K T L E E F Q D V Y L V M E L M D A N L C Q V I H M E L D H E R M S Y L L Y Q M L C G I K H L H S A G I I H R D L K P S N I V V K S D C T L K I L D F G L A R T A C T N F M M T P Y V V T R Y Y R A P E V I L G M G Y K E N V D I W S V G C I M G E L V K G C V I F Q G T D H I D Q W N K V I E Q L G T P S A E F M K K L Q P T V R N Y V E N R P K Y P G I K F E E L F P D W I F P S E S E R D K I K T S Q A R D L L S K M L V I D P D K R I S V D E A L R H P Y I T V W Y D P A E A E A P P P Q I Y D A Q L E E R E H A I E E W K E L I Y K E V M D W E E R S K N G V V K D Q P S D A A V S S N A T P S Q S S S I N D I S S M S T E Q T L A S D T D S S L D A S T G P L E G C R).

Daxx is a Fas-binding protein that activates JNK and apoptosis as described in U.S. Pat. No. 6,159,731, which is hereby incorporated by reference.

JNK2 and Type I Diabetes

Mitogen-activated protein kinases (MAPKs) form a large family of serine-threonine protein kinases conserved through evolution. In mammalian cells, four distinct MAPK cascades have been identified: extracellular signal-regulated kinases (ERKs), c-Jun amino-terminal kinases (JNKs) or stress-activated protein kinases (SAPKs), p38 MAP kinase (p38) or cytokine suppressive anti-inflammatory drug binding protein, and Erk5/BMK. JNK protein kinases are activated by dual phosphorylation on Tyr and Thr. The JNK family includes JNK1 (46 kDa isoform), JNK2 (55-kDa isoform), and JNK3. JNK1 and JNK2 are ubiquitously expressed, while JNK3 is largely restricted to brain, heart and testis. Ip and Davis, Curr Opin Cell Biol. 1998 April; 10(2):205-19; Sluss et al., Mol Cell Biol. 1994 December; 14(12):8376-84. In addition to stress such as UV exposure, the INK family is activated by cytokines and TNF-α.

Recently, it has been suggested that JNK1, but not JNK2, is implicated in obesity and insulin resistance associated with type II diabetes. International publication PCT (WO 02/085396), Lee et al., c-Jun N-terminal kinase (JNK) mediates feedback inhibition of the insulin signaling cascade. J Biol Chem 278, 2896-902 (2003), and Aguirre et al., The c-Jun NH(2)-terminal kinase promotes insulin resistance during association with insulin receptor substrate-1 and phosphorylation of Ser(307). J Biol Chem 275, 9047-54 (2000).

JNKs take part in the regulation of CD4+ T cell differentiation. Recently studies suggest the cooperation of CD4+ and CD8+ T cells for islet infiltration and destruction of β-cells. The cytokine environment enables the differentiation of CD4+ T cells to two different phenotypes: 1) Th1 cells which produce interleukin-2 (IL-2) and interferon-γ (IFN-γ) inducing a cellular immune response or 2) Th2 cells that secrete IL-4, IL-5, and IL-10 which support humoral immunity and down-regulate the inflammatory actions of Th1 cells. Benign insulitis is associated with differentiation of CD+ T cells in a phenotype of Th2 cells, whereas destructive insulitis appears to be associated with Th1 cells. Pro-inflammatory cytokines produced by islet infiltrating immune cells act as effector molecules, and IL-1β in combination with IFN-γ and TNF-α triggers apoptosis of the β-cells.

The applicant has discovered that JNK2 plays role in type I (insulin-dependent) diabetes that is caused by autoimmune destruction of β-cells. Studies of non-obese diabetic (NOD) mice demonstrated that disruption of the MAPK9 gene (which encodes the JNK2 protein kinase) decreased destructive insulitis and reduced disease progression to type I diabetes. CD4+ T cells from JNK2-deficient NOD mice produced less IFN-γ, and significantly increased amounts of IL-4 and IL-5, indicating polarization towards the Th2 phenotype. This role of JNK2 to control the Th1/Th2 balance of the immune response motivated the applicant to use JNK2 inhibitors to protect against type I autoimmune diabetes.

The applicants discovered reduced insulitis and reduced progression to type I diabetes in NOD/Mapk9−/− mice. The transition from non-pathogenic insulitis to type I diabetes correlates with the change from a predominance of Th2 to Th1 cytokines in the islets. A Th1 (IFN-γ) environment accelerates the recruitment of islet-specific CD4+ T cells and also accelerates the onset of type I diabetes. In contrast, a Th2 pancreatic environment appears to protect against autoimmune diabetes. Thus, administration of IL-4 systemically or expression of IL-4 in NOD mice in vivo interferes with the islet infiltration by T cells and prevents Th1-mediated destructive insulitis and type I diabetes. The observation that JNK2-deficiency causes selective polarization of CD4+ T cells to the Th2 phenotype with increased IL-4 expression can lead to creation of a Th2 pancreatic environment that protects against autoimmune diabetes. Thus, one embodiment of the current invention is the treatment and prevention of type I diabetes by administering to a subject an inhibitor of JNK2. In further embodiments, the JNK2 inhibitor selectively inhibits JNK2.

Inappropriate activation of T cells initiates many autoimmune diseases. Although, the applicant does not desire the invention to be limited to any particular mechanism, JNK2 inhibitors may play several roles in preventing type I diabetes. JNK2 inhibitors may play a suppressive role in autoimmune disease by causing a negative selection of autoreactive T cells in the thymus. In type I diabetes, JNK2 inhibitors may prevent beta-cell apoptosis caused by cytokines and oxidative stress caused by reactive oxygen species and nitric oxide. Furthermore, JNK2 inhibitors may prevent the production of macrophage-derived cytokines, including TNF-α, contributing to the development of destructive insulitis and diabetes. It is possible that JNK2 inhibitors act in multiple ways as those mentioned or those not mentioned.

JNK2 Inhibitors

The present invention is direct to methods useful for treating or preventing type I diabetes in a subject, comprising administering an effective amount of a JNK2 inhibitor or selective JNK2 inhibitor. Illustrative JNK2 inhibitors and JNK2 selective inhibitors are set forth below.

Antisense oligonucleotides of JNK2 have been described in U.S. Pat. Nos. 6,221,850 and 6,133,246, which are hereby incorporated by reference. Oligonucleotides that are specifically hybridizable with nucleic acids encoding JNK2 are JNK2 inhibitors. Embodiments include oligonucleotides comprising up to 30 nucleotides (typically between 15 and 25 nucleotides) in length wherein said oligonucleotides have a sequence that specifically binds to nucleic acids encoding JNK2 (e.g. human MAPK9 gene, GenBank Accession number NC 000005 and any corresponding mRNA). Further illustrative embodiments can be found in the corresponding patents provided above. JNK-interacting protein-1 (JIP-1) was first identified as a direct binding partner for JNK1 in yeast two-hybrid analysis. The specificity of interactions was underlined by JIP-1 interacting with JNK1, JNK2, and JNK3, but not ERK or p38 MAPKs, and failing to alter the activity of these two closely related MAPKs. Furthermore, JNKs bound to JIP-1 with greater affinity than its transcription factor substrates, c-Jun and activating transcription factor-2 (ATF2). A number of amino acid sequences based on the binding domain of JIP-1, JIP-2, and c-Jun have been disclosed as JNK inhibitors including those disclosed in WO 03/103698, U.S. Pat. No. 6,780,970, and U.S. Patent Application Publication 2002/0119135, all of which or any present or future corresponding U.S. application or patent are hereby incorporated by reference. Examples of JNK2 inhibitor peptides include a peptide which includes (in whole or in part) the sequence NH$_2$-DTYRPKRPTTLNLFPQVPRSQDT-COOH [SEQ ID NO:3]. In another embodiment, the peptide includes the sequence NH$_2$-EEPHKHRPTTLRLTTLGAQDS-COOH [SEQ ID NO:4]. In another embodiment, the peptide includes the sequence NH2-FLNLTTPRKPR-COOH [SEQ ID NO:5]. In another embodiment the peptide includes the sequence NH$_2$-FLNLTTPRKPRYTDGSGTGPG-COOH [SEQ ID NO:6]. Further illustrative embodiments can be found in the identified references.

The JNK2 inhibitor peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

The following sulfonamide derivatives are contemplated for use as therapeutics in treating type I diabetes:

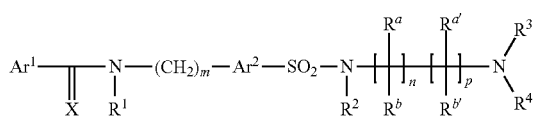

wherein: $Ar^1$ is a substituted or unsubstituted aryl or heteroaryl group; X is O or S; $Ar^2$ a substituted or unsubstituted aryl or heteroaryl group; $R^1$ and $R^2$ are independently selected from the group consisting of hydrogen and a $C_1$-$C_6$-alkyl group; $R^a$, $R^{a\prime}$, $R^b$, $R^{b\prime}$ are independently selected from the group consisting of hydrogen and $C_1$-$C_6$-alkyl; or $R^{a\prime}$ and $R^a$ or $R^{b\prime}$ together with the carbon atoms they are linked, form a substituted or unsubstituted 5-8-membered saturated, partially unsaturated or aromatic ring containing optionally one or more heteroatoms selected from O, N, S; $R^3$ is selected from the group consisting of H, $C_2$-$C_{10}$-alkenyl, $C_2$-$C_{10}$-alkynyl, aryl, heteroaryl, 3-8 membered cycloalkyl optionally containing 1-3 heteroatoms selected from the group consisting of N, O, and S; aryl $C_1$-$C_{10}$-alkyl and heteroaryl $C_1$-$C_{10}$-alkyl; or $R^3$ and $R^a$ or $R^{a\prime}$ form, together with the N atom linked to $R^3$, a 5-8-membered saturated ring, containing optionally at least one further heteroatom selected from O, N, S; $R^4$ is selected from the group consisting of H and —C(H)$R^5R^6$; $R^5$ and $R^6$ are independently selected from the group consisting of H, $C_1$-$C_{10}$-alkyl, $C_2$-$C_{10}$-alkenyl, $C_2$-$C_{10}$-alkynyl, aryl, heteroaryl, 3-8 membered cycloalkyl optionally containing 1-3 heteroatoms selected from the group consisting of N, O, and S; aryl $C_1$-$C_{10}$-alkyl and heteroaryl $C_1$-$C_{10}$-alkyl; m is an integer from 1 to 5; n is an integer from 0 to 2; and p is an integer from 1 to 10. These compounds have been described in United States Patent Application Publication US 2004/0248886 as particular efficient and selective inhibitors of JNK2, and this publication or any present or future corresponding U.S. application or patent are hereby incorporated by reference.

Preferred embodiments include compounds of the following formula:

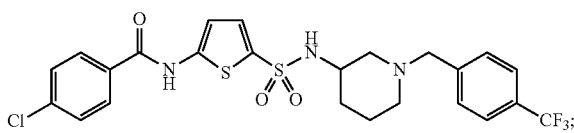
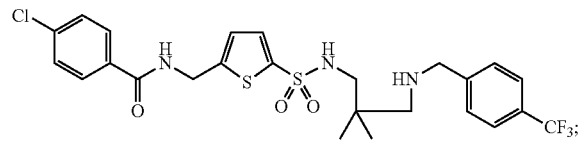
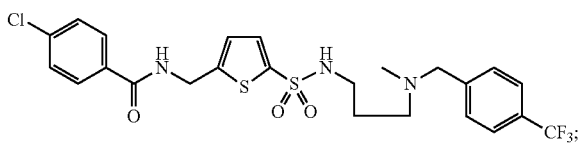
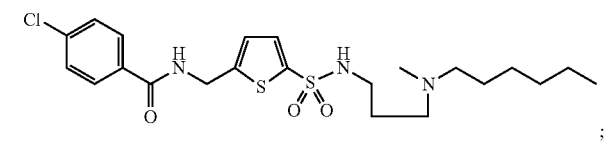
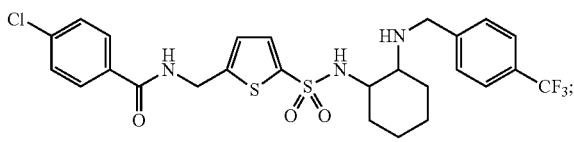
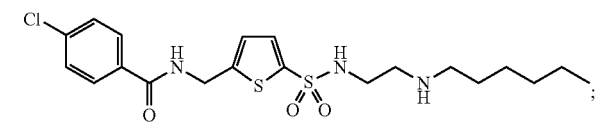
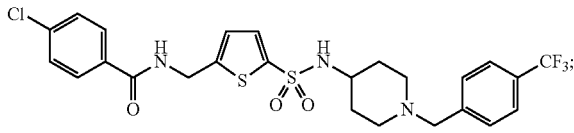
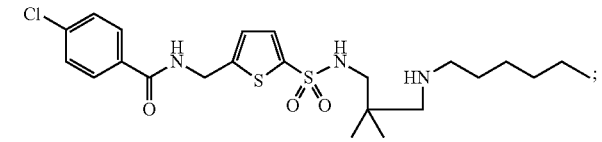
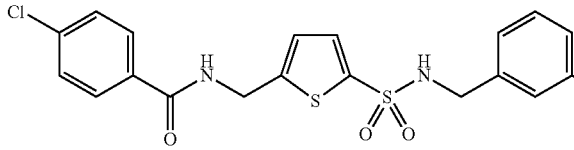
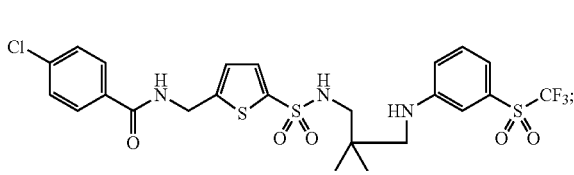
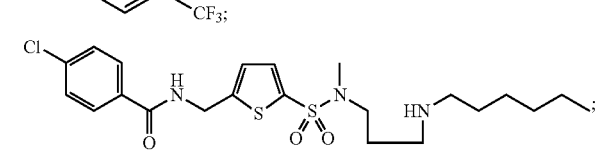

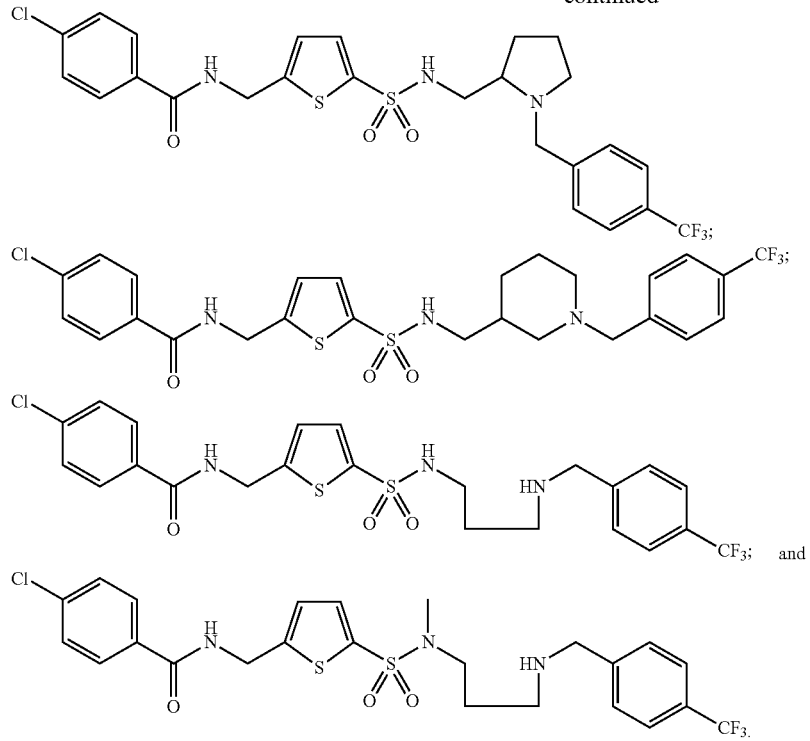

Further illustrative embodiments can be found in the identified reference.

The following sulfonamide derivatives are contemplated for use as therapeutics in treating type I diabetes:

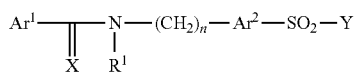

wherein $Ar^1$ and $Ar^2$ are independently from each other substituted or unsubstituted aryl or heteroaryl groups; X is O or S, preferably O; $R^1$ is hydrogen or a $C_1$-$C_6$ alkyl group, or $R^1$ forms a substituted or unsubstituted 5-6 membered saturated or unsaturated ring with $Ar^1$; n is an integer from 0 to 5, preferably between 1-3 and most preferred 1; Y is an unsubstituted or a substituted 4-12 membered saturated cyclic or bicyclic alkyl containing at least one nitrogen atom, whereby one nitrogen atom within said ring is forming a bond with the sulfonyl group thus providing a sulfamide. These compounds have been described in PCT International Publication Number WO 01/23378 as particular efficient and selective inhibitors of JNK2, and this publication or any present or future corresponding U.S. application or patent are hereby incorporated by reference. Preferred embodiments include:

4-chloro-N-[(5-{[4-(2,4-difluorobenzoyl)piperidin-1-yl]sulfonyl}thien-2-yl)methyl]benzamide;
4-chloro-N-[(5-{[4-(phenylacetyl)-1,4-diazepan-1-yl]sulfonyl}thien-2-yl)methyl]benzamide;
N-({5-[(4-anilinopiperidin-1-yl)sulfonyl]thien-2-yl}methyl)-4-chlorobenzamide;
N-[(5-{[4-(1H-1,2,3-benzotriazol-1-yl)piperidin-1-yl]sulfonyl}thien-2-yl)methyl]-4-chlorobenzamide;
N-[(5-{[4-(1H-benzimidazol-1-yl)piperidin-1-yl]sulfonyl}thien-2-yl)methyl]-4-chlorobenzamide;
4-chloro-N-{[5-({4-[3-propylanilino]piperidin-1-yl}sulfonyl)thien-2-yl]methyl}benzamide;
4-chloro-N-[(5-{[4-(4-chloroanilino)piperidin-1-yl]sulfonyl}thien-2-yl)methyl]benzamide;
4-chloro-N-({5-[(4-{3-[(2-hydroxyethyl)sulfonyl]anilino}piperidin-1-yl)sulfonyl]thien-2-yl}methyl)benzamide;
N-{[5-({4-[3-(aminosulfonyl)anilino]piperidin-1-yl}sulfonyl)thien-2-yl]methyl}-4-chlorobenzamide;
4-chloro-N-[(5-{[4-(1-naphtholyl)piperazin-1-yl]sulfonyl}thien-2-yl)methyl]benzamide;
4-nitro-N-[(5-{[4-(3-methoxyanilino)piperidin-1-yl]sulfonyl}thien-2-yl)methyl]benzamide;
methyl 3-{[1-({5-[({4-nitrobenzoyl}amino)methyl]thien-2-yl}sulfonyl)piperidin-4-yl]amino}benzoate;
N-[(5-[4-(1H-1,2,3-benzotriazol-1-yl)piperidin-1-yl)sulfonyl]thien-2-yl)methyl]-2-hydroxybenzamide;
N-({5-[(4-{2-nitroanilino}piperidin-1-yl)sulfonyl]thien-2-yl}methyl)-3-methoxybenzamide. Further illustrative embodiments can be found in the identified reference.

The following sulfonyl derivatives are contemplated for use as therapeutics in treating type I diabetes:

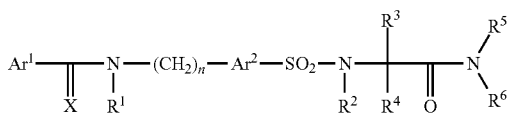

wherein $Ar^1$ and $Ar^2$ are independently from each other substituted or unsubstituted aryl or heteroaryl groups; X is O or S, preferably O; $R^1$ is hydrogen or a $C_1$-$C_6$ alkyl group, preferably hydrogen; alternatively, $R^1$ forms a substituted or unsubstituted 5-6 membered saturated or unsaturated fused ring with $Ar^1$; According to a further alternative R2 and R4 could form a substituted or unsubstituted 5-6-membered saturated or unsaturated ring. $R^2$ is hydrogen, or a substituted or unsubstituted $C_1$-$C_6$-alkyl, preferably hydrogen; n is an integer from 0 to 5, preferably between 1-3 and most preferred 1; $R_3$ and $R_4$ are independently from each other selected form the group comprising or consisting of natural or synthetic amino acid residues, hydrogen, substituted or unsubstituted $C_1$-$C_6$-alkyl, like trihalomethyl, substituted or unsubstituted $C_1$-$C_6$ alkoxy, $NH_2$, SH, $C_1$-$C_6$-thioalkyl, acylamino, aminocarbonyl, substituted or unsubstituted $C_1$-$C_6$-alkoxycarbonyl, aryl, heteroaryl, substituted or unsubstituted 4-8-membered cyclic alkyl, optionally contain 1-3 heteroatoms, carboxyl, cyano, halogen, hydroxyl, nitro, acyloxy, sulfoxy, sulfonyl $C_1$-$C_6$-thioalkoxy, whereby though, at least one of $R_3$ and/or $R_4$ must be an amino acid residue; $R^5$ is H or substituted or unsubstituted $C_1$-$C_6$-alkyl; $R^6$ is selected from the group comprising or consisting of substituted or unsubstituted $C_1$-$C_6$ aliphatic alkyl, substituted or unsubstituted saturated cyclic $C_4$-$C_s$-alkyl optionally containing 1-3 heteroatoms and optionally fused with an aryl or an heteroaryl; or $R^6$ is a substituted or unsubstituted aryl, substituted or unsubstituted heteroaryl whereby said aryl or heteroaryl groups are optionally substituted or unsubstituted $C_1$-$C_6$-alkoxy, substituted or unsubstituted $C_2$-$C_6$ alkenyl, substituted or unsubstituted $C_2$-$C_6$ alkynyl, amino acylamino aminocarbonyl, substituted or unsubstituted $C_1$-$C_6$-alkoxycarbonyl, aryl, carboxyl, cyano, halogen, hydroxy, nitro, acyloxy, acylamino, sulfoxy, sulfonyl, $C_1$-$C_6$-thioalkoxy or; or $R^5$ and $R^6$ taken together form a substituted or unsubstituted 4-8-membered saturated cyclic alkyl or heteroalkyl group. These compounds have been described in PCT International Publication Number WO 01/23379 as particular efficient and selective inhibitors of JNK2, and this publication or any present or future corresponding U.S. application or patent are hereby incorporated by reference. Preferred embodiments include:

4-chloro-N-({5-[({2-[(2-{[3-chloro-5-(trifluoromethyl)pyridin-2-yl]amino}ethyl)amino]-2-oxoethyl}amino)sulfonyl]thien-2-yl}methyl)benzamide and 4-chloro-N-[(5-{[(2-oxo-2-{3-{(trifluoromethyl)sulfonyl}anilino}ethyl)amino]sulfonyl}thien-2-yl)methyl]benzamide. Further illustrative embodiments can be found in the identified reference.

The following sulfonyl hydrazine derivatives are contemplated for use as therapeutics in treating type I diabetes:

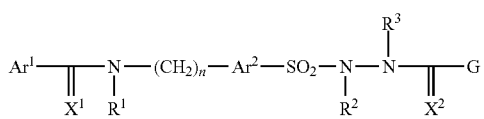

wherein $Ar^1$ and $Ar^2$ are independently from each other substituted or unsubstituted aryl or heteroaryl groups; $X^1$ and $X^2$ are independently from each other O or S; $R^1$, $R^2$, and $R^3$ are independently from each other hydrogen or a $C_1$-$C_6$ alkyl substituent or $R^1$ forms a substituted or unsubstituted 5-6-membered saturated or unsaturated ring with $Ar^1$; or $R^2$ and $R^3$ form a substituted or unsubstituted 5-6-membered saturated or unsaturated ring; n is an integer from 0 to 5; G is selected from a group comprising or consisting of an unsubstituted or substituted 4-8-membered heterocycle containing at least one heteroatom, or G is a substituted or unsubstituted $C_1$-$C_6$ alkyl group. These compounds have been described in PCT International Publication Number WO 01/23382 as particular efficient and selective inhibitors of JNK2, and this publication or any present or future corresponding U.S. application or patent are hereby incorporated by reference. Preferred embodiments include:

4-chloro-N-(4-{[2-(4-{[3-chloro-5-(trifluoromethyl)pyridin-2-yl]amino}butanoyl)hydrazino]sulfonyl}benzyl)benzamide;

N-[(5-{[2-(4-{[3-chloro-5-(trifluoromethyl)pyridin-2-yl]amino}butanoyl)hydrazino]sulfonyl}thien-2-yl)methyl]-2-oxo-1,2-dihydropyridine-3-carboxamide;

N-[(5-{[2-(4-{[3-chloro-5-(trifluoromethyl)pyridin-2-yl]amino}butanoyl)hydrazino]sulfonyl}thien-2-yl)methyl]-2-hydroxybenzamide;

4-chloro-N-[(5-{[2-({2-[(2-chlorophenoxy)methyl]-1,3-thiazol-4-yl}carbonyl)hydrazino]sulfonyl}thien-2-yl)methyl]benzamide 4-chloro-N-[(5-{[2-({2-[4-(1,3-dithiolan-2-yl)phenyl]-1,3-thiazol-4-yl}carbonyl)hydrazino]sulfonyl}thien-2-yl)methyl]benzamide. Further illustrative embodiments can be found in the identified reference.

The following derivatives are contemplated for use as therapeutics in treating type I diabetes:

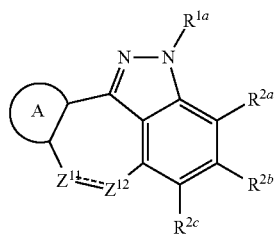

Wherein $Z^{11}$ and $Z^{12}$ each independently represent a carbonyl group, an oxygen atom, a sulfur atom, a methine group which may be substituted, a methylene group which may be substituted or a nitrogen atom which may be substituted; ==== represents a double bond or a single bond; $R^{1a}$ represents a hydrogen atom, a $C_1$-$C_6$ alkyl group, a phenyl group or a benzyl group; $R^{2a}$, $R^{2b}$ and $R^{2c}$ each independently represent a group selected from the following Substituent Group (a); the ring A represents a benzene ring which may have one to three groups selected from the following Substituent Group (a), a naphthalene ring which may have one to three groups selected from the following Substituent Group (a) or a 5- to 10-membered aromatic heterocyclic ring which may have one to three groups selected from the following Substituent Group (a); Substituent Group (a) (1) a hydrogen atom, (2) halogen atoms, (3) a nitro group, (4) a hydroxyl group, (5) a cyano group, (6) a carboxyl group, (7) an amino group, (8) a formyl group or (9) a group represented by the formula:

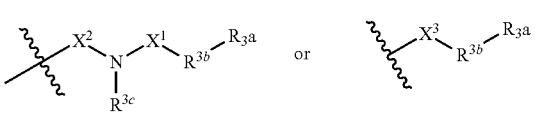

wherein $X^1$ and $X^2$ each independently represent a single bond, —CO—, —$SO_2$— or $C_1$-$C_6$-methylene group; $X^3$ represents a single bond, —CO—, —$SO_2$, —O—, —CO—O— or —O—CO—; $R^{3b}$ represents a $C_1$-$C_6$ alkylene group or a single bond; $R^{3a}$ and $R^{3c}$ represent a hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_8$ cycloalkyl group which may be substituted, a $C_6$-$C_{14}$ aromatic cyclic hydrocarbon group which may be substituted, a 5- to 14-membered aromatic heterocyclic group which may be substituted or a hydrogen atom. These compounds have been described in PCT International Publication Number WO 03/072550, and this publication or any present or future corresponding U.S. application or patent are hereby incorporated by reference. Preferred embodiments include:

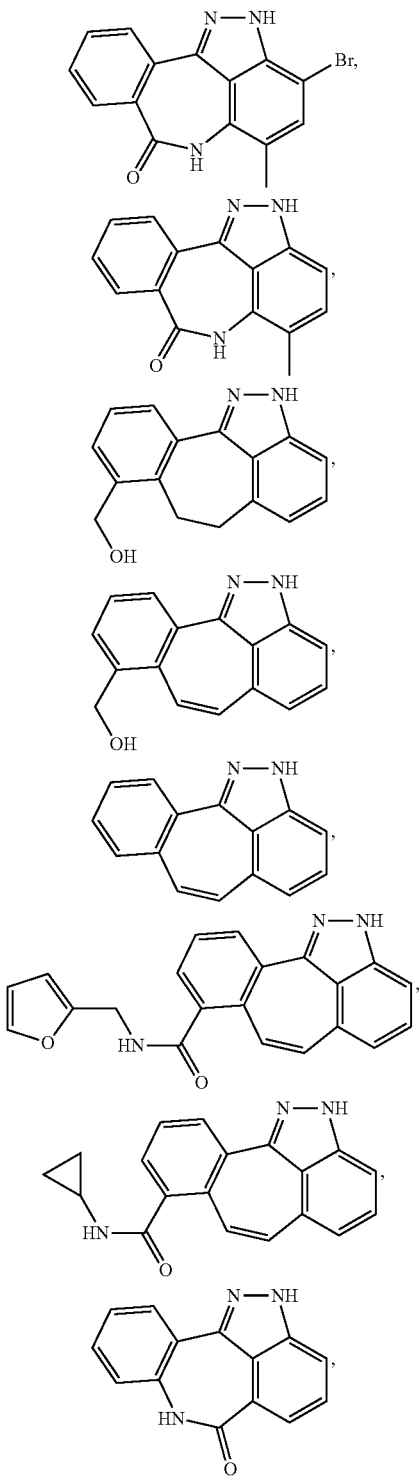

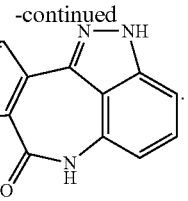

Further illustrative embodiments can be found in the identified references.

The following derivatives are contemplated for use as therapeutics in treating type I diabetes:

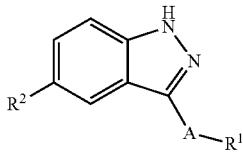

wherein: A is a direct bond, —$(CH_2)_a$—$(CH_2)_b$CH=CH$(CH_2)_c$—, or —$(CH_2)_b$C≡C$(CH_2)_c$—; $R^1$ is aryl, heteroaryl or heterocycle fused to phenyl, each being optionally substituted with one to four substituents independently selected from $R^3$; $R^2$ is —$R^3$, —$R^4$, —$(CH_2)_b$C(=O)$R^5$, —$(CH_2)_b$C(=O)O$R^5$, —$(CH_2)_b$C(=O)N$R^5R^6$, —$(CH_2)_b$C(=O)N$R_5$(CH_2)CC(=O)$R^6$, —$(CH_2)_b$N$R^5$C(=O)$R^6$, —$(CH_2)_b$N$R^5$C(=O)N$R^6R^7$, —$(CH_2)_b$N$R^5R^6$, —$(CH_2)_b$O$R^5$, —$(CH^2)_b$SO$_d R^5$ or —$(CH_2)_b$SO$_2$N$R^5R^6$; a is 1, 2, 3, 4, 5 or 6; b and c are the same or different and at each occurrence independently selected from 0, 1, 2, 3 or 4; d is at each occurrence 0, 1 or 2; $R^3$ is at each occurrence independently halogen, hydroxy, carboxyl, alkyl, alkoxy, haloalkyl, acyloxy, thioalkyl, sulfinylalkyl, sulfonylalkyl, hydroxyalkyl, aryl, arylalkyl, heterocycle, heterocycloalkyl, —C(=O)O$R^8$, —OC(=O)$R^8$, —C(=O)N$R^8R^9$, —C(=O)N$R^8$O$R^9$, —SO$_2$N$R^8R^9$, —N$R^8$SO$_2R^9$, —CN, —NO$_2$, —N$R^8R^9$, —N$R^8$C(=O)$R^9$, —N$R^8$C(=)(CH$_2$)$_b$O$R^9$, —N$R^8$C(=O)(CH$_2$)$_bR^9$, —O(CH$_2$)$_b$N$R^8R^9$, or heterocycle fused to phenyl; $R^4$ is alkyl, aryl, arylalkyl, heterocycle or heterocycloalkyl, each being optionally substituted with one to four substituents independently selected from $R^3$, or $R^4$ is halogen or hydroxy; $R^5$, $R^6$ and $R^7$ are the same or different and at each occurrence independently hydrogen, alkyl, aryl, arylalkyl, heterocycle or heterocycloalkyl, wherein each of $R^5$, $R^6$ and $R^7$ are optionally substituted with one to four substituents independently selected from $R^3$; and $R^8$ and $R^9$ are the same or different and at each occurrence independently hydrogen, alkyl, aryl, arylalkyl, heterocycle, or heterocycloalkyl, or $R^8$ and $R^9$ taken together with the atom or atoms to which they are bonded form a heterocycle, wherein each of $R^8$, $R^9$, and $R^8$ and $R^9$ taken together to form a heterocycle are optionally substituted with one to four substituents independently selected from $R^3$. These compounds have been described in PCT International Publication Number WO 02/10137, as well as, U.S. Patent Application Publication 2004/0077877 and 2004/0127536 as particular efficient and selective inhibitors of JNK2, all of which or any present or future corresponding U.S. application or patent are hereby incorporated by reference. Preferred embodiments include:

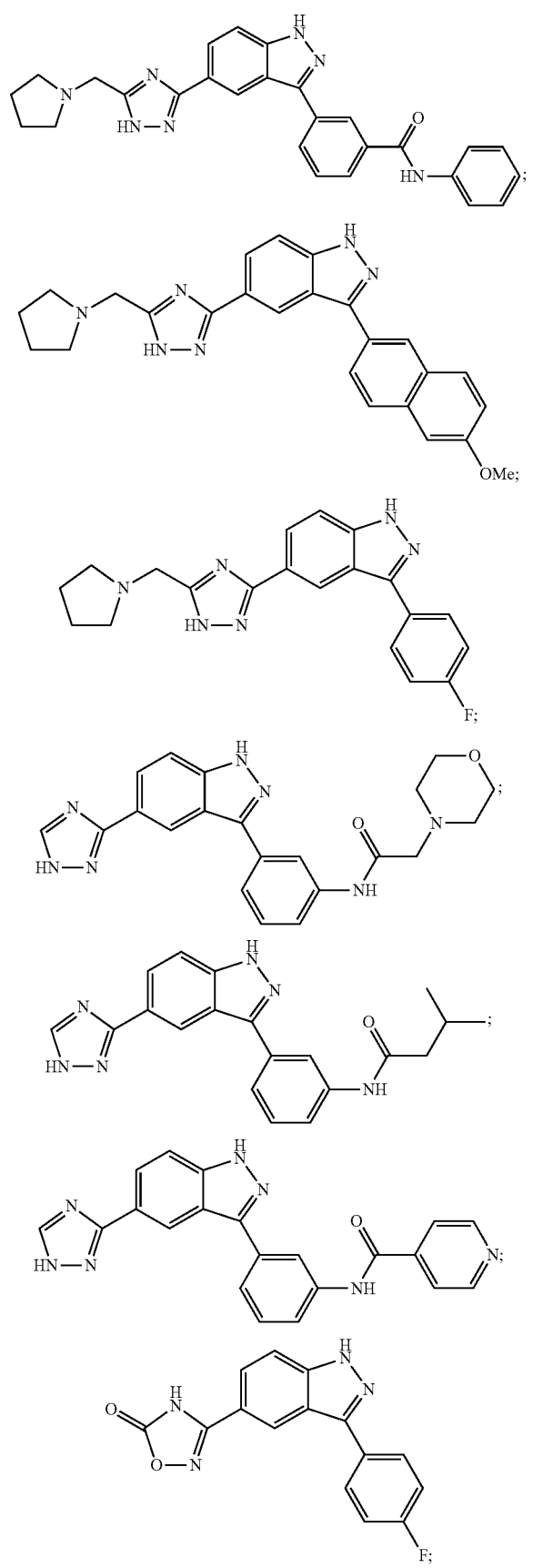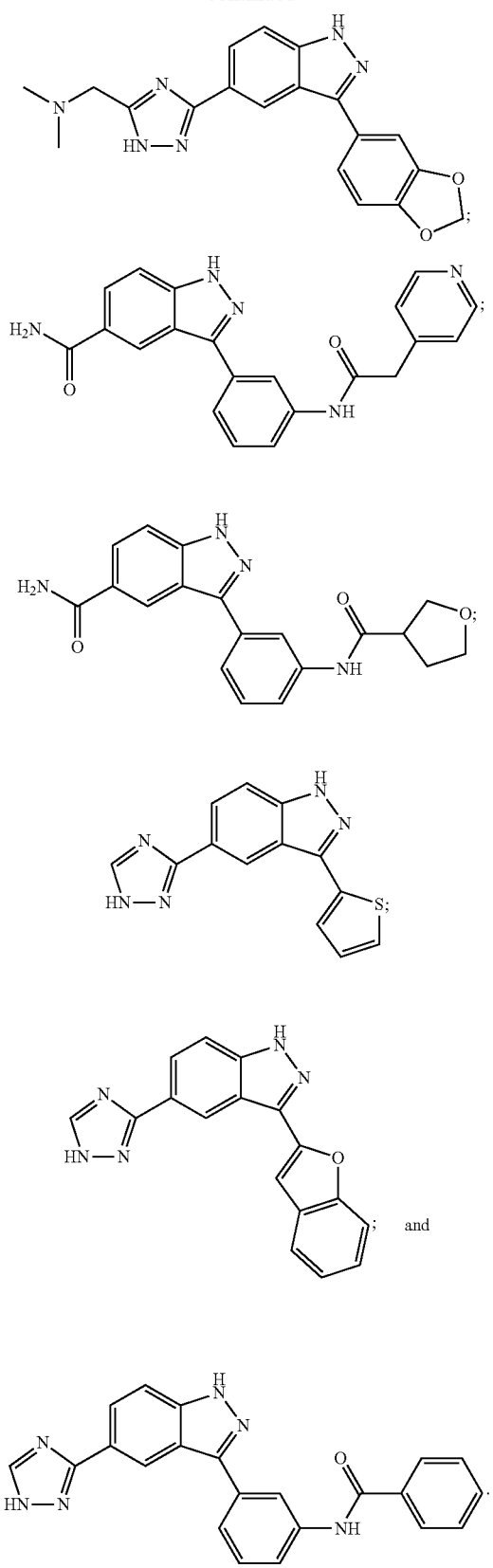
Further illustrative embodiments can be found in the identified reference(s).

The following derivatives are contemplated for use as therapeutics in treating type I diabetes:

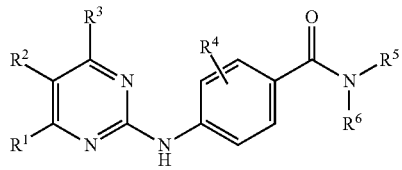

wherein R¹ is aryl or heteroaryl optionally substituted with one to four substituents independently selected from $R^7$; $R^2$ is hydrogen; $R^3$ is hydrogen or lower alkyl; $R^4$ represents one to four optional substituents, wherein each substituent is the same or different and independently selected from halogen, hydroxy, lower alkyl and lower alkoxy; $R^5$ and $R^6$ are the same or different and independently —$R^8$, —$(CH_2)_aC(=O)R^9$, —$(CH2)_aC(=O)OR^9$, —$(CH2)_aC(=O)NR^9R(CH2)_aC(=O)NR^9(CH2)_bC(=O)R^{10}$, —$(CH2)_aNR^9C(=O)R^{10}$, $(CH2)_aNR^{11}C(=O)NR^9R^{10}$, —$(CH2)_aNR^9R^{10}$, —$(CH2)_aOR^9$, —$(CH2)_aSO_cR^9$ or —$(CH2)_nSO2NR^9R^{10}$; or $R^5$ and $R^6$ taken together with the nitrogen atom to which they are attached to form a heterocycle or substituted heterocycle; $R^7$ is at each occurrence independently halogen, hydroxy, cyano, nitro, carboxyl, alkyl, alkoxy, haloalkyl, acyloxy, thioalkyl, sulfinylalkyl, sulfonylalkyl, hydroxyalkyl, aryl, arylalkyl, heterocycle, substituted heterocycle, heterocycloalkyl, —$C(=O)OR^8$, —$OC(=O)R^8$, —$C(=O)NR^8R^9$, —$C(=O)NR^8OR^9$, —$SO_cR^8$, —$SO_cNR^8R^9$, $NR^8SOR^9$, —$NR^8R^9$, —$NR^8C(=O)R^9$, —$NR^8C(=O)(CH_2)_bOR^9$, —$NR^8C(=O)(CH2)_bR^9$, —$O(CH2)_bNR^8R^9$, or heterocycle fused to phenyl; $R^8$, $R^9$, $R^{10}$ and $R^{11}$ are the same or different and at each occurrence independently hydrogen, alkyl, aryl, arylalkyl, heterocycle, heterocycloalkyl; or $R^8$ and $R^9$ taken together with the atom or atoms to which they are attached to form a heterocycle; a and b are the same or different and at each occurrence independently selected from 0, 1, 2, 3 or 4; and c is at each occurrence 0, 1 or 2. These compounds have been described in PCT International Publication Number WO 02/46170, as well as U.S. Patent Application Publication 2004/01066634 as particular efficient and selective inhibitors of JNK2, and all of which or any present or future corresponding U.S. application or patent are hereby incorporated by reference. Preferred embodiments include:

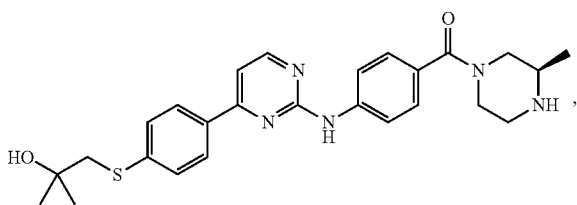

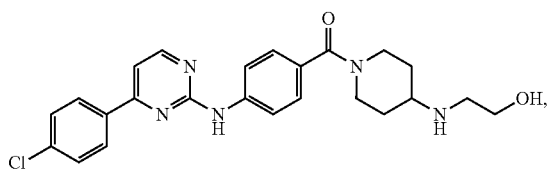

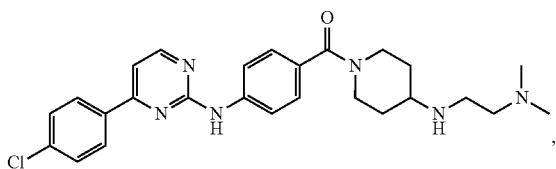

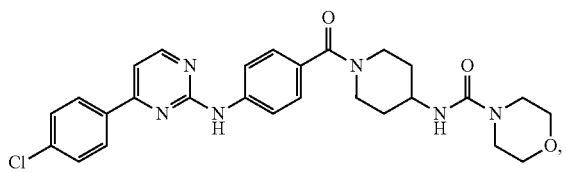

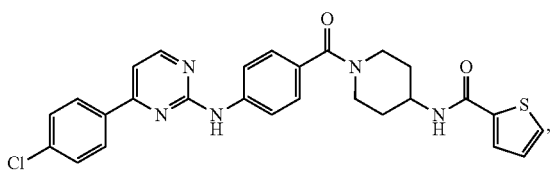

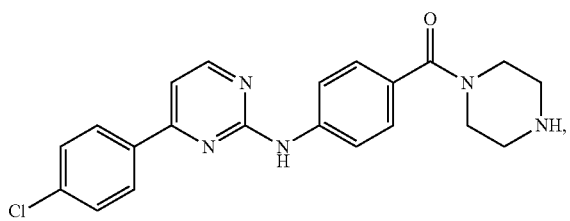

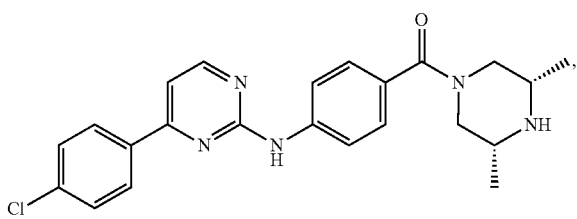

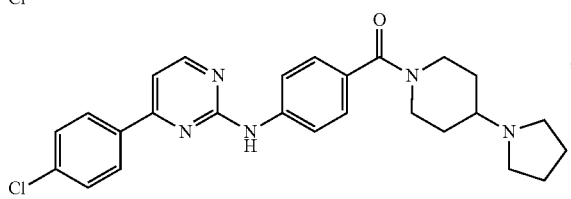

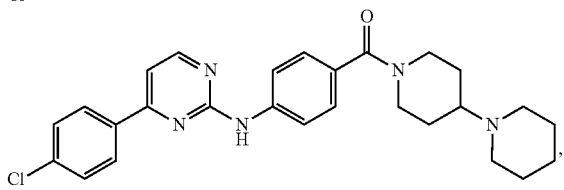

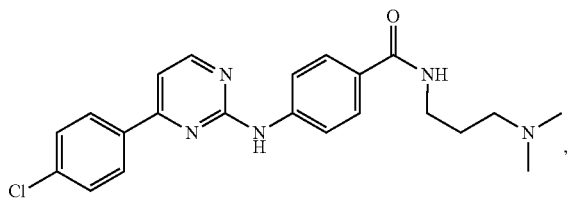

-continued

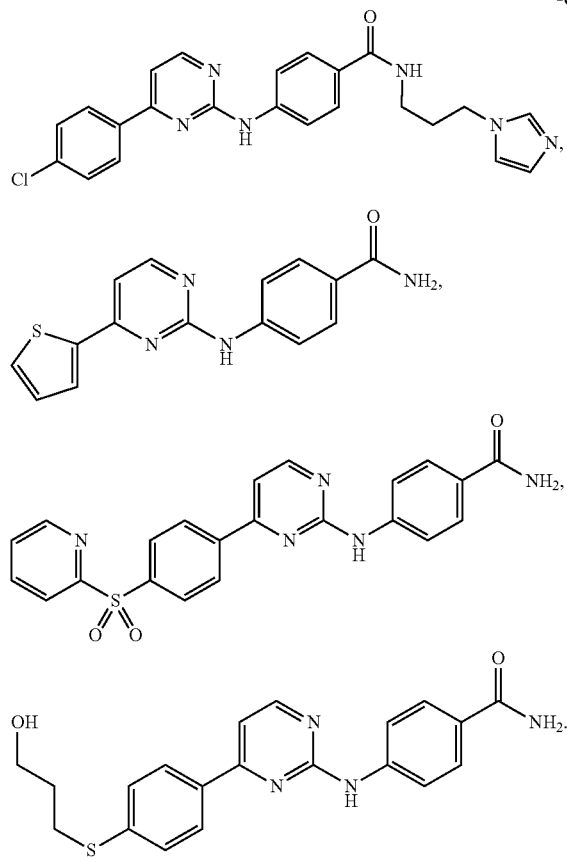

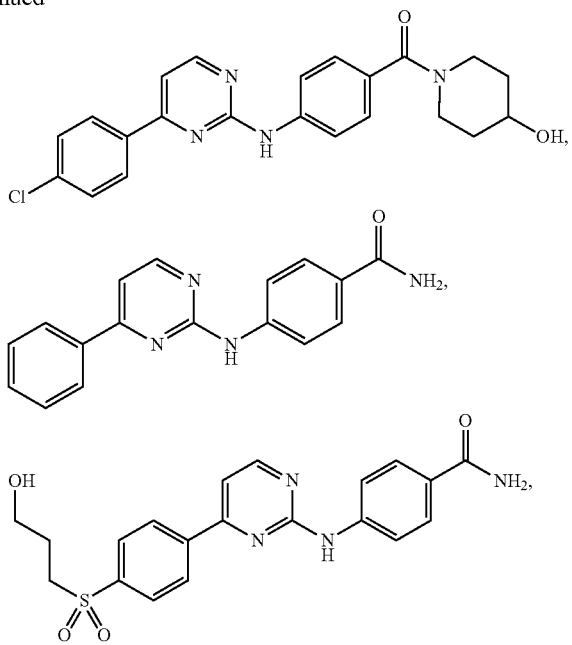

Further illustrative embodiments can be found in the identified reference.

The following derivatives are contemplated for use as therapeutics in treating type I diabetes:

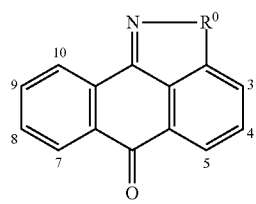

wherein $R^0$ is —O—, —S(O)—, —S(O)$_2$—, NH or —CH$_2$—; being: (i) unsubstituted, (ii) monosubstituted and having a first substituent, or (iii) disubstituted and having a first substituent and a second substituent; the first or second substituent, when present, is at the 3, 4, 5, 7, 8, 9, or 10 position, wherein the first and second substituent, when present, are independently alkyl, hydroxy, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono-alkylaminoalkoxy, di-alkylaminoalkoxy, —NHR$^3$R$^4$, —NH(CH$_2$)$_n$NR$^3$R$^4$, —NH(=O)R$^5$, —NHSO$_2$R$^5$, —C(=O)NR$^3$,R$^4$, or —SO$_2$NR$^3$R$^4$; wherein n is 0-6, R$^3$ and R$^4$ are taken together and represent alkylidene or a heteroatom-containing cyclic alkylidene or R$^3$ and R$^4$ are independently hydrogen, alkyl, cycloalkyl, aryl, arylalkyl, cycloalkylalkyl, aryloxyalkyl, alkoxyalkyl, aminoalkyl, mono-alkylaminoalkyl, or di-alkylaminoalkyl; and R$^5$ is hydrogen, alkyl, cycloalkyl, aryl, arylalkyl, cycloalkylalkyl, alkoxy, alkoxyalkyl, alkoxycarbonylalkyl, amino, mono-alkylamino, di-alkylamino, arylamino, arylalkylamino, cycloalkylamino, cycloalkylalkylamino, aminoalkyl, mono-alkylaminoalkyl, or di-alkylaminoalkyl. These compounds have been described in PCT International Publication Number WO 01/12609, as well as WO 02/066450, as well as U.S. Patent Application Publication 2004/0092562 and all of which or any present or future corresponding U.S. application or patent are hereby incorporated by reference. Preferred embodiments include:

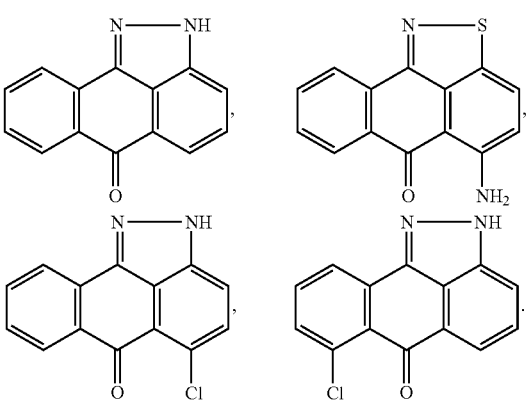

Further illustrative embodiments can be found in the identified reference(s).

The following derivatives are contemplated for use as therapeutics in treating type I diabetes:

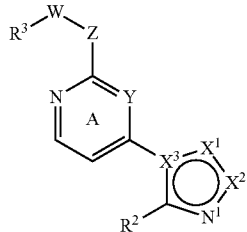

wherein N¹ is a nitrogen atom optionally having a substituent or a hydrogen atom, X¹ is (i) a carbon atom optionally having substituent(s) or hydrogen atom(s), (ii) an oxygen atom, (iii) a sulfur atom or (iv) a nitrogen atom optionally having a substituent or a hydrogen atom, X² is (i) a carbon atom optionally having substituent(s) or hydrogen atom(s), (ii) an oxygen atom, (iii) a sulfur atom or (iv) a nitrogen atom optionally having a substituent or a hydrogen atom, X³ is (i) a carbon atom or (ii) a nitrogen atom, wherein (1) when X¹ is an oxygen atom or a sulfur atom, X² is a carbon atom optionally having substituent(s) or hydrogen atom(s), X³ is a carbon atom and N¹ is a nitrogen atom, (2) when X¹ is a nitrogen atom having a substituent or a hydrogen atom and X³ is a carbon atom, X2 is a carbon atom optionally having substituent(s) or hydrogen atom(s) and N¹ is a nitrogen atom, (3) when X¹ and X³ are each a nitrogen atom, X² is a carbon atom optionally having substituent(s) or hydrogen atom(s), and N¹ is a nitrogen atom, (4) when X¹ is a carbon atom optionally having substituent(s) or hydrogen atom(s) and X² is an oxygen atom or a sulfur atom, X³ is a carbon atom and N¹ is a nitrogen atom, (5) when X¹ is a carbon atom optionally having substituent(s) or hydrogen atom(s) and X³ is a carbon atom, one of N¹ and X² is a nitrogen atom, and the other is a nitrogen atom having a substituent or a hydrogen atom, (6) when X¹ and X² are each a carbon atom optionally having substituent(s) or hydrogen atom(s) and X³ is a carbon atom, N¹ is a nitrogen atom having a substituent or a hydrogen atom, and (7) when X¹ and X² are each a carbon atom optionally having substituent(s) or hydrogen atom(s) and X³ is a nitrogen atom, N¹ is a nitrogen atom, ring A optionally further has substituent(s), ring B is an aromatic ring, Y is (i) a carbon atom optionally having substituent(s) or hydrogen atom(s) or (ii) a nitrogen atom, Z is a bond, —NR⁴— (R⁴ is a hydrogen atom or a hydrocarbon group optionally having substituent(s)), an oxygen atom or an optionally oxidized sulfur atom, W is a bond or a divalent hydrocarbon group optionally having substituent(s), R² is an aromatic group optionally having substituent(s), and R³ is a hydrocarbon group optionally having substituent(s) or a heterocyclic group optionally having substituent(s). These compounds have been described in U.S. Patent Application Publication 2004/0063946 and all of which or any present or future corresponding U.S. application or patent are hereby incorporated by reference. Preferred embodiments include:

4-[4-(3-methylphenyl)-2-propyl-1,3-thiazol-5-yl]-2-pyridylamine;

[5-(2-cyclohexylamino-4-pyridyl)-4-(3-methylphenyl)-1,3-thiazol-2-yl]amine;

[5-(2-cyclopentylamino-4-pyridyl)-4-(3-methylphenyl)-1,3-thiazol-2-yl]amine;

4-[4-(3-chlorophenyl)-2-ethyl-1,3-thiazol-5-yl]-N-[(1S)-1-phenylethyl]-2-Pyridylamine Hydrochloride;

N-[4-[2-ethyl-4-(3-methylphenyl)-1,3-thiazol-5-yl]-2-pyridyl]Phenylacetamide;

N-[4-[4-(4-chlorophenyl)-2-ethyl-1,3-thiazol-5-yl]-2-pyridyl]benzamide;

N-[4-[2-ethyl-4-(4-fluoro-3-methyl-phenyl)-1,3-thiazol-5-yl]-2-pyridyl]benzamide. Further illustrative embodiments can be found in the identified reference(s).

The following derivatives are contemplated for use as therapeutics in treating type I diabetes:

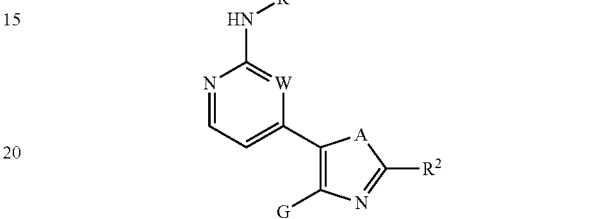

wherein: W is nitrogen or CH; G is hydrogen or $C_{1-3}$ aliphatic wherein one methylene unit of G is optionally replaced by —C(O)—, —C(O)O—, —C(O)NH—, —SO₂—, or —SO₂NH—; A is —N-T$_{(n)}$-R, oxygen, or sulfur; R¹ is selected from -T$_{(n)}$-R or -T$_{(n)}$-Ar¹; each n is independently 0 or 1; T is a $C_{1-4}$ alkylidene chain wherein one methylene unit of T is optionally replaced by —C(O)—, —C(O)O—, —C(O)NH—, —SO₂—, or —SO₂NH—; Ar¹ is a 3-7 membered monocyclic saturated, partially saturated or aromatic ring having 0-3 heteroatoms independently selected from nitrogen, oxygen, or sulfur, or a 8-10 membered bicyclic saturated, partially saturated or aromatic ring having 0-5 heteroatoms independently selected from nitrogen, oxygen, or sulfur, wherein each member of Ar¹ is optionally substituted with one —Z—R³ and one to three additional groups independently selected from —R, halogen, oxo, —NO₂, —CN, —OR, —SR, —N(R)₂, —NRC(O)R, —NRC(O)N(R)₂, —NRCO₂R, —C(O)R, —CO₂R, —OC(O)R, —C(O)N(R)₂, —OC(O)N(R)₂, —S(O)R, —SO₂R, —SO₂N(R)₂, —NRSO₂R, —NRSO₂N(R)₂, —C(O)C(O)R, or —C(O)CH₂C(O)R; each R is independently selected from hydrogen or a $C_{1-6}$ aliphatic, wherein said aliphatic is optionally substituted with one to three groups independently selected from oxo, —CO₂R', —OR', —N(R')₂, —SR', —NO₂, —NR'C(O)R', —NR'C(O)N(R')₂, —NR'CO₂R', —C(O)R', —OC(O)R', —C(O)N(R)₂, —OC(O)N(R')₂, —S(O)R', —SO₂R', —SO₂N(R')₂, —NR'SO₂R', —NR'SO₂N(R')₂, —C(O)C(O)R', —C(O)CH₂C(O)R', halogen, or —CN, or two R bound to the same nitrogen atom are taken together with that nitrogen atom to form a five or six membered heterocyclic or heteroaryl ring having one to two additional heteroatoms independently selected from oxygen, nitrogen, or sulfur; each R' is independently selected from hydrogen or $C_{1-6}$ aliphatic, wherein said aliphatic is optionally substituted with one to three groups independently selected from oxo, —CO₂H, —OH, —NH₂, —SH, —NO₂, —NHC(O)H, —NHC(O)NH₂, —NHCO₂H, —C(O)H, —OC(O)H, —C(O)NH₂, —OC(O)NH₂, —S(O)H, SO₂H, —SO₂NH₂, —NHSO₂H, —NHSO₂NH₂, —C(O)C(O)H, —C(O)CH₂C(O)H, halogen, or —CN, or two R' bound to the same nitrogen atom are taken together with that nitrogen atom to form a five or six membered heterocyclic or heteroaryl ring optionally having one or two additional heteroatoms independently selected from nitrogen, oxygen, or sulfur; Z is a $C_1$-$C_6$ alkylidene chain wherein up to two nonadjacent methylene units of Z are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, —N(R)C(O)N(R)—, —S(O)—, —SO₂—, —N(R)SO₂—, —N(R)SO₂N(R)—, —O—, —S—, or —N(R)—; R² is -Q$_{(n)}$-Ar²; Ar² is selected from a 3-7 membered monocyclic saturated, saturated or aromatic ring having 0-3 heteroatoms independently selected from nitrogen, oxygen, or sulfur, or a 8-10 membered bicyclic saturated, saturated or aromatic ring having 0-5 heteroatoms independently selected from nitrogen, oxygen, or sulfur, wherein each member of Ar² is optionally substituted with 1-5 groups independently selected from —Z—R³, —R, halogen, oxo, —NO2, —CN, —OR, —SR, —N(R)₂, NRC(O)R, —NRC(O)N(R)₂, —NRCO₂R, —C(O)R, —CO₂R, OC(O)R, —C(O)N(R)₂, —OC(O)N(R)₂, —S(O)R, —SO₂R, SO₂N(R)₂, —N(R)SO₂R, —N(R)SO₂N(R)₂, —C(O)C(O)R, or —C(O)CH₂C(O)R; Q is a C$_{1-3}$ alkylidene chain wherein up to two nonadjacent methylene units of Q are optionally replaced by —C(O)—, —C(O)O—, —C(O)C(O)—, —C(O)N(R)—, —OC(O)N(R)—, —N(R)N(R)—, —N(R)N(R)C(O)—, —N(R)C(O)—, —N(R)C(O)O—, —N(R)C(O)N(R)—, —S(O)—, —SO₂—, —N(R)SO₂—, —SO₂N(R)—, —N(R)SO₂N(R)—, —O—, —S—, or —N(R)—; R³ is selected from —Ar³, —R, halogen, —NO₂, —CN, —OR, —SR, —N(R)₂, —NRC(O)R, —NRC(O)N(R)₂, —NRCO₂R, —C(O)R, —CO₂R, —OC(O)R, —C(O)N(R)₂, —OC(O)N(R)₂, —SOR, —SO₂R, —SO₂N(R)₂, —NRSO₂R, —NRSO₂N(R)₂, —C(O)C(O)R, or —C(O)CH2C(O)R; and Ar³ is a 5-6 membered saturated, partially saturated, or aromatic ring having 0-3 heteroatoms independently selected from nitrogen, oxygen, or sulfur, wherein each member of Ar³ is optionally substituted with halogen, oxo, —CN, —NO₂, —R', —OR', —N(R')₂, —N(R')C(O)R', N(R')C(O)N(R')₂, —N(R)CO₂R', —C(O)R', —CO₂R', OC(O)R', —C(O)N(R')₂, —OC(O)N(R')₂, or —SO₂R'; provided that when W is nitrogen and: (i) A is —N-T$_{(n)}$R and R2 is a saturated ring or (ii) A is sulfur, then R¹ is other than an optionally substituted phenyl. These compounds have been described in U.S. Patent Application Publication 2004/0097531 and all of which or any present or future corresponding U.S. application or patent are hereby incorporated by reference. Preferred embodiments include:

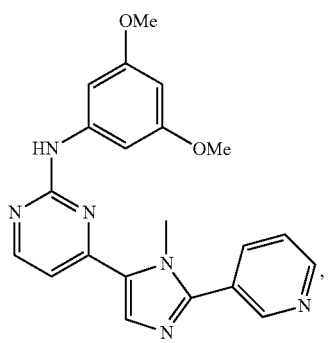

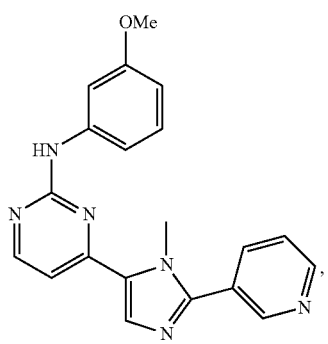

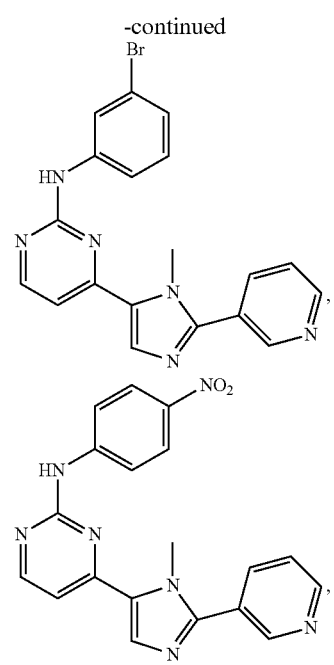

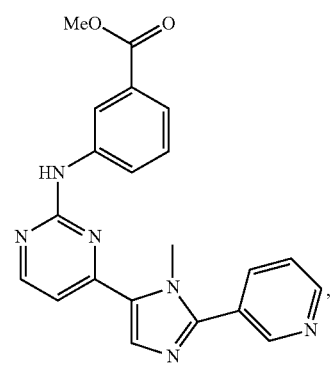

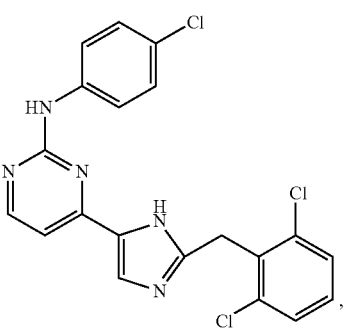

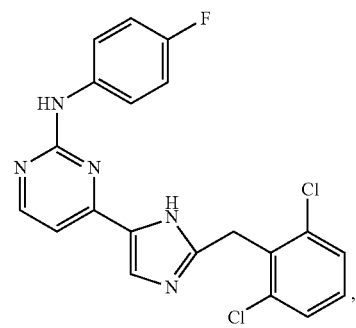

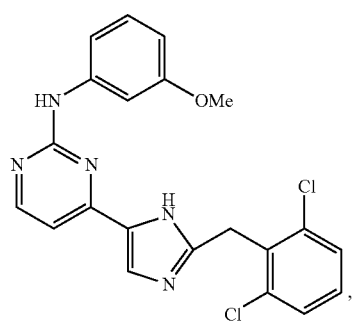
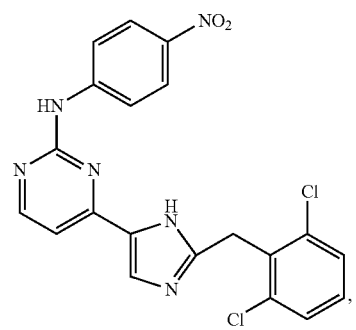
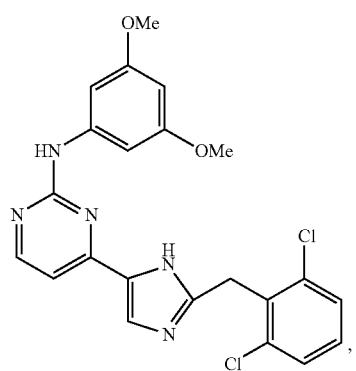
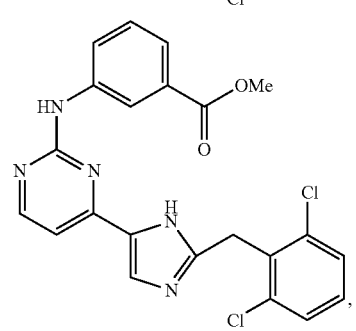
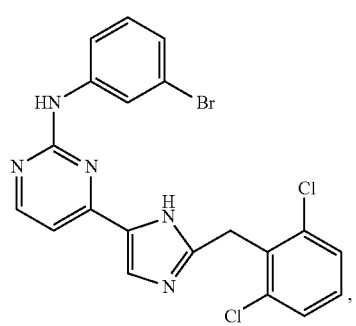
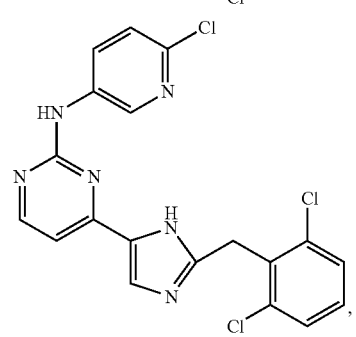
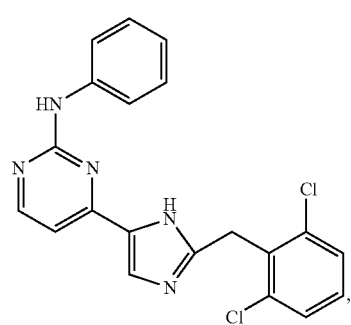
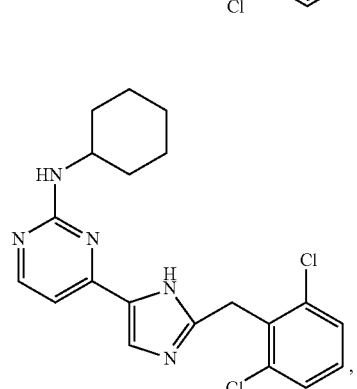
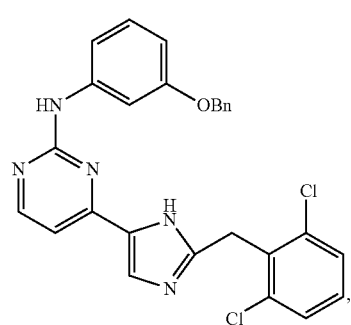
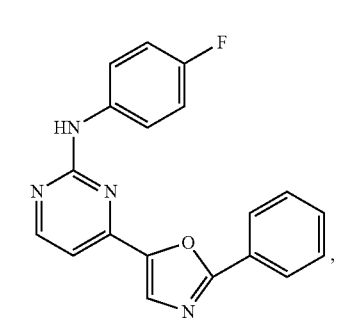

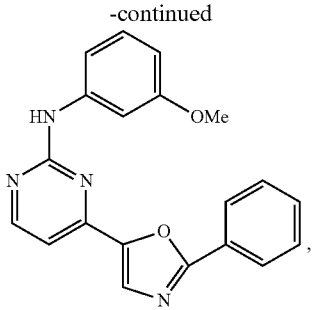

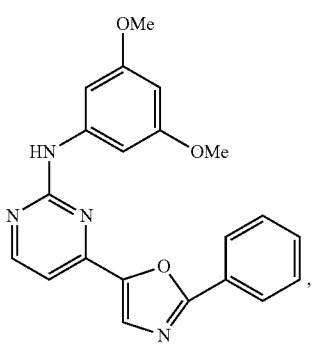

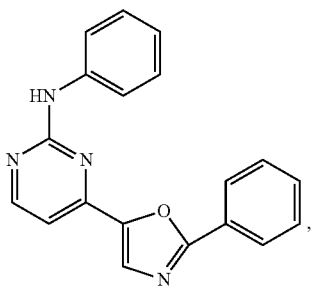

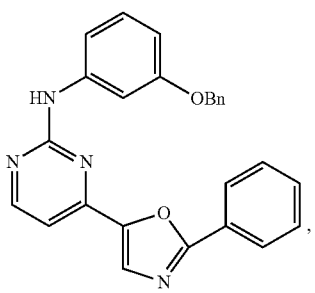

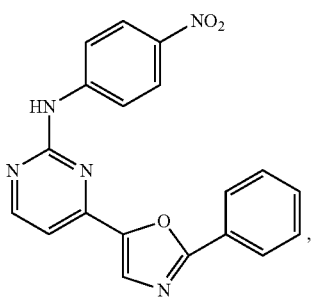

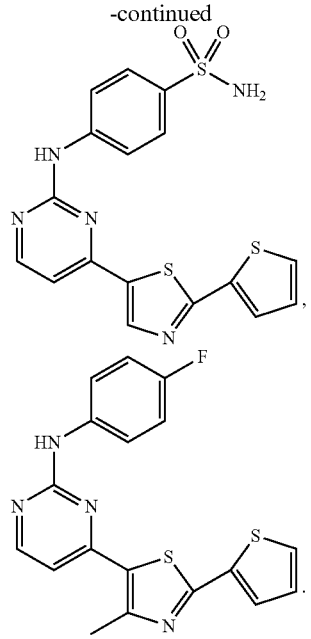

Further illustrative embodiments can be found in the identified reference.

The following derivatives are contemplated for use as therapeutics in treating type I diabetes:

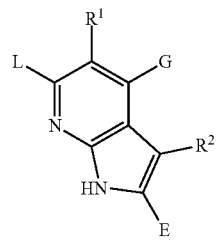

wherein R¹ is optionally substituted carbocyclyl or heterocyclyl group, R² is an optionally substituted five or six membered heterocyclyl group or an optionally substituted six membered carbocyclyl group, E is hydrogen, halogen cyano, $C_{1-6}$ alkoxyl or $C_{1-6}$ alkyl, G is hydrogen, halogen, cyano, $C_{1-6}$ alkoxy or $C_{1-6}$ alkyl, and L is hydrogen, halogen, cyano, $C_{1-6}$ alkoxy or $C_{1-6}$ alkyl. These compounds have been described in International Publication Number WO 2004/078756 and all of which or any present or future corresponding U.S. application or patent are hereby incorporated by reference. Preferred embodiments include:

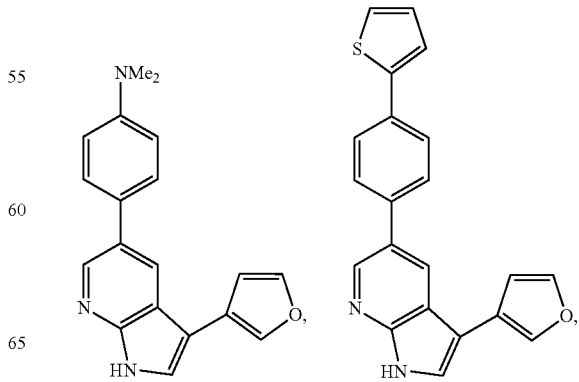

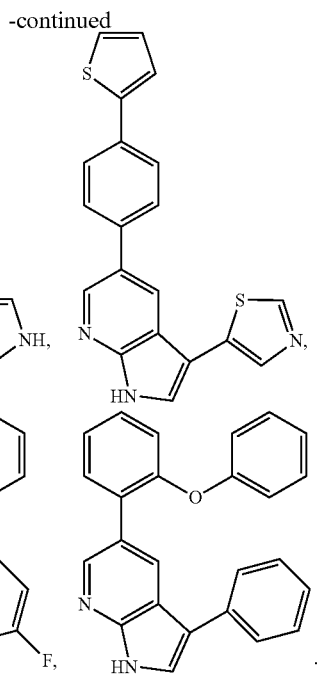

Further illustrative embodiments can be found in the identified reference.

The following derivatives are contemplated for use as therapeutics in treating type I diabetes:

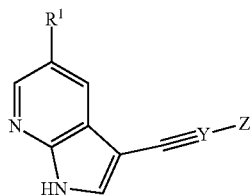

wherein $R^1$ is an optionally substituted $C_{3-16}$ carbocyclyl or $C_{3-12}$ heterocyclyl group, Y is N or C and Z is lone electron pair, hydrogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $-(CH_2)_nOR^2$, $-(CH_2)_nNR^2{}_2$, $-CO_2R^2$, $-COR^2$, $-CONR^2{}_2$, wherein the $C_{1-12}$ alkyl group optionally contains one or more insertions selected from $-O-$, $-N(R^2)-$, $-SO-$, $-SO_2-$; and each substitutable nitrogen atom in Z is optionally substituted by $-R^3$, $-COR^3$, $-SO_2R^3$ or $-CO_2R^3$; wherein n is 1 to 6, preferably n is 1, 2, or 3; wherein $R^2$ is hydrogen, $C_{1-12}$ alkyl, $C_{3-16}$ carbocyclyl or $C_{3-12}$ heterocyclyl, $C_{1-12}$ alkyl$C_{3-16}$ carbocyclyl, or $C_{1-12}$ alkyl$C_{3-12}$ heterocyclyl optionally substituted by one or more of $C_{1-6}$ alkyl, halogen, $C_{1-6}$ haloalkyl, $-OR^4$, $-SR^4$, $-NO_2$, CN, $-NR^4R^4$, $NR^4COR^4$, $-NR^4CONR^4R^4$, $-NR^4CO_2R^4$, $-CO_2R^4$, $-COR^4$, $-CONR^4{}_2$, $-SO_2R^4$, $-SONR^4{}_2$, $-SOR^4$, $-SO_2NR^4R^4$, $-NR^4SO_2R^4$, wherein the $C_{1-12}$ alkyl group optionally incorporates on or two insertions selected for the group consisting of $-O-$, $-N(R^4)-$, $-S-$, $-SO-$, $-SO_2-$, wherein each $R^4$ may be the same or different and is defined below; wherein two $R^2$ and $NR^2{}_2$ may form a partially saturated, unsaturated or fully saturated five to seven membered ring containing one to three heteroatoms, optionally and independently substituted with one or more halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $-OR^5$, $-SR^5$, $-NO_2$, CN, $-NR^5R^5$, $-NR^5COR^5$, $-NR^5CONR^5R^5$, $-NR^5CO_2R^5$, $-CO_2R^5$, $-COR^5$, $-CONR^5{}_2$, $-SO_2R^5$, $-SONR^5{}_2$, $-SOR^5$, $-SO_2NR^5R^5$, $-NR^5SO_2R^5$; and each saturated carbon in the optional ring is further optionally and independently substituted by $=O$, $=S$, $NNR^6{}_2$, $=N-OR^6$, $=NNR^6COR^6$, $=NNR^6CO_2R^6$, $=NNSO_2R^6$, or $=NR^6$; wherein $R^3$ is hydrogen, $C_{1-6}$ alkyl, $C_{1-6}$ haloalkyl, or $C_{6-12}$ aryl; wherein $R^4$ is hydrogen, $C_{1-6}$ alkyl, $C_{1-6}$ haloalkyl, or $C_{6-12}$ aryl; wherein $R^5$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, $-OR^7$, $-SR^7$, $-NO_2$, CN, $-NR^7R^7$, $-NR^7COR^7$, $-NR^7CONR^7R^7$, $-NR^7CO_2R^7$, $-CO_2R^7$, $-COR^7$, $-CONR^7{}_2$, $-SO_2R^7$, $-SONR^7{}_2$, $-SOR^7$, $-SO_2NR^7R^7$, $-NR^7SO_2R^7$; wherein the $C_{1-12}$ alkyl group optionally incorporates one or two insertions selected from the group consisting of $-O-$, $-N(R^7)-$, $-S-$, $-SO-$, $-SO_2-$, wherein each $R^7$ may be the same or different and is defined below; wherein $R^6$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, $-OR^7$, $-SR^7$, $-NO_2$, CN, $-NR^7R^7$, $-NR^7COR^7$, $-NR^7CONR^7R^7$, $-NR^7CO_2R^7$, $-CO_2R^7$, $-COR^7$, $-CONR^7{}_2$, $-SO_2R^7$, $-SONR^7{}_2$, $-SOR^7$, $-SO_2NR^7R^7$, $-NR^7SO_2R^7$; wherein the $C_{1-12}$ alkyl group optionally incorporates one or two insertions selected from the group consisting of $-O-$, $-N(R^7)-$, $-S-$, $-SO-$, $-SO_2-$, wherein each $R^7$ may be the same or different and is defined below; wherein $R^7$ is hydrogen, $C_{1-6}$ alkyl, or $C_{1-6}$ haloalkyl; wherein the optionally substituted carbocyclyl or heterocyclyl group in $R^1$ and Z is optionally and independently fused to a partially saturated, unsaturated or fully saturated five to seven membered ring containing zero to three heteroatoms, and each substitutable carbon atom in R1 or Z, including the optional fused ring, is optionally and independently substituted by one or more of halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $-(CH_2)_nOR^{12}$, $-(CH_2)_nNR^{12}{}_2$, $-OR^{12}$, $-SR^{12}$, $-NO_2$, CN, $-NR^{12}R^{12}$, $-NR^{12}COR^{12}$, $-NR^{12}CONR^{12}R^{12}$, $-NR^{12}CO_2R^{12}$, $-CO_2R^{12}$, $-COR^{12}$, $-CONR^{12}{}_2$, $-SO_2R^{12}$, $-SONR^{12}{}_2$, $-SOR^{12}$, $-SO_2NR^{12}R^{12}$, $-NR^{12}SO_2R^{12}$; wherein the $C_{1-12}$ alkyl group optionally contains one or more insertions selected from $-O-$, $-N(R^{12})-$, $-S-$, $-SO-$, $-SO_2-$, and each saturated carbon in the optionally fused ring is further optionally and independently substituted by $=O$, $=S$, $NNR^{13}{}_2$, $=N-OR^{13}$, $=NNR^{13}COR^{13}$, $=NNR^{13}CO_2R^{13}$, $=NNSO_2R^{13}$, or $=NR^{13}$; and each substitutable nitrogen atom in R' is optionally substituted by $-R^{14}$, $-COR^{14}$, $-SO_2R^{14}$, or $-CO_2R^{14}$; wherein n is 1 to 6, preferably n is 1,2, or 3; wherein $R^{12}$ is hydrogen, $C_{1-12}$ alkyl, $C_{3-16}$ carbocyclyl or $C_{3-12}$ heterocyclyl, optionally substituted by one or more of $C_{1-6}$ alkyl, halogen, $C_{1-6}$ haloalkyl, $-OR^{15}$, $-SR^{15}$, $-NO_2$, CN, $-NR^{15}R^{15}$, $-NR^{15}COR^{15}$, $-NR^{15}CONR^{15}R^{15}$, $-NR^{15}CO_2R^{15}$, $-CO_2R^{15}$, $-COR^{15}$, $-CONR^{15}{}_2$, $-SO_2R^{15}$, $-SONR^{15}{}_2$, $-SOR^{15}$, $-SO_2NR^{15}R^{15}$, $-NR^{15}SO_2R^{15}$; wherein the $C_{1-12}$ alkyl group optionally incorporates one or two insertions selected from the group consisting of $-O-$, $-N(R^{15})-$, $-S-$, $-SO-$, $-SO_2-$, wherein each $R^7$ may be the same or different and is defined below; wherein two $R^{12}$ and $NR^{12}{}_2$ may form a partially saturated, unsaturated or fully saturated five to seven membered ring containing one to three heteroatoms, optionally and independently substituted with one or more halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $-OR^{16}$, —SR$^{16}$, —NO$_2$, CN, —NR$^{16}$R$^{16}$, —NR$^{16}$COR$^{16}$, —NR$^{16}$CONR$^{16}$R$^{16}$, —NR$^{16}$CO$_2$R$^{16}$, —CO$_2$R$^{16}$, —COR$^{16}$, —CONR$^{16}_2$, —SO$_2$R$^{16}$, —SONR$^{16}_2$, —SOR$^{16}$, —SO$_2$NR$^{16}$R$^{16}$, —NR$^{16}$SO$_2$R$^{16}$; and each saturated carbon in the optional ring is further optionally and independently substituted by =O, NNR$^{17}_2$, =N—OR$^{17}$, =NNR$^{17}$COR$^{17}$, =NNR$^{17}$CO$_2$R$^{17}$, =NNSO$_2$R$^{17}$, or =NR$^{17}$; wherein R$^{13}$ is hydrogen, C$_{1-12}$ alkyl, C$_{3-16}$ carbocyclyl or C$_{3-12}$ heterocyclyl, optionally substituted by one or more of C$_{1-6}$ alkyl, halogen, C$_{1-6}$ haloalkyl, —OR$^{15}$, —SR$^{15}$, —NO$_2$, CN, —NR$^{15}$R$^{15}$, —NR$^{15}$COR$^{15}$, —NR$^{15}$CONR$^{15}$R$^{15}$, —NR$^{15}$CO$_2$R$^{15}$, —CO$_2$R$^{15}$, —COR$^{15}$, —CONR$^{15}_2$, —SO$_2$R$^{15}$, —SONR$^{15}_2$, —SOR$^{15}$, —SO$_2$NR$^{15}$R$^{15}$, —NR$^{15}$SO$_2$R$^{15}$; wherein the C$_{1-12}$ alkyl group optionally incorporates one or two insertions selected from the group consisting of —O—, —N(R$^{15}$)—, —SO—, —SO$_2$—, wherein each R$^{15}$ may be the same or different and is defined below; wherein R$^{14}$ is hydrogen, C$_{1-6}$ alkyl, C$_{1-6}$ haloalkyl, or C$_{6-12}$ aryl; wherein R$^{15}$ is hydrogen, C$_{1-6}$ alkyl, C$_{1-6}$ haloalkyl; wherein R$^{16}$ is hydrogen, C$_{1-12}$ alkyl, C$_{3-16}$ carbocyclyl or C$_{3-12}$ heterocyclyl, optionally substituted by one or more of C$_{1-6}$ alkyl, halogen, C$_{1-6}$ haloalkyl, —OR$^{18}$, —SR$^{18}$, —NO$_2$, CN, —NR$^{18}$R$^{18}$, —NR$^{18}$COR$^{18}$, —NR$^{18}$CONR$^{18}$R$^{18}$, —NR$^{18}$CO$_2$R$^{18}$, —CO$_2$R$^{18}$, —COR$^{18}$, —CONR$^{18}_2$, —SO$_2$R$^{18}$, —SONR$^{18}_2$, —SOR$^{18}$, —SO$_2$NR$^{18}$R$^{18}$, —NR$^{18}$SO$_2$R$^{18}$; wherein the C$_{1-12}$ alkyl group optionally incorporates one or two insertions selected from the group consisting of —O—, —N(R$^{18}$)—, —S—, —SO—, —SO$_2$—, wherein each R$^{18}$ may be the same or different and is defined below; wherein R$^{17}$ is hydrogen, C$_{1-12}$ alkyl, C$_{3-16}$ carbocyclyl or C$_{3-12}$ heterocyclyl, optionally substituted by one or more of C$_{1-6}$ alkyl, halogen, C$_{1-6}$ haloalkyl, —OR$^{18}$, —NO$_2$, CN, —NR$^{18}$R$^{18}$, —NR$^{18}$CONR$^{18}$R$^{18}$, —NR$^{18}$CO$_2$R$^{18}$, —CO$_2$R$^{18}$, —COR$^{18}$, —CONR$^{18}_2$, —SO$_2$R$^{18}$, —SONR$^{18}_2$, —SOR$^{18}$, —SO$_2$NR$^{18}$R$^{18}$, —NR$^{18}$SO$_2$R$^{18}$; wherein the C$_{1-12}$ alkyl group optionally incorporates one or two insertions selected from the group consisting of —O—, —N(R$^{18}$)—, —S—, —SO—, —SO$_2$—, wherein each R$^{18}$ may be the same or different and is defined below; wherein R$^{18}$ is hydrogen, C$_{1-6}$ alkyl, C$_{1-6}$ haloalkyl. These compounds have been described in International Publication Number WO 2004/101565 and all of which or any present or future corresponding U.S. application or patent are hereby incorporated by reference. Preferred embodiments include:

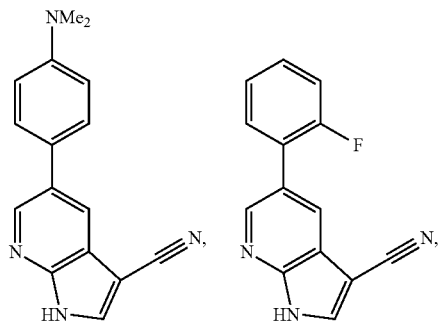

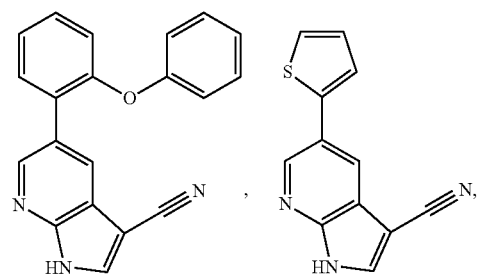

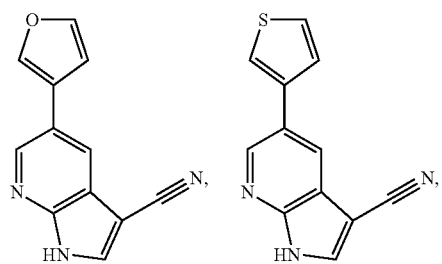

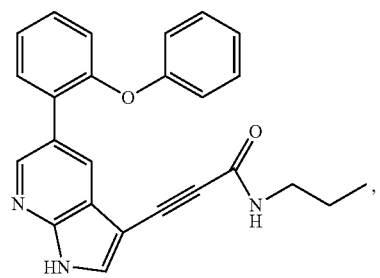

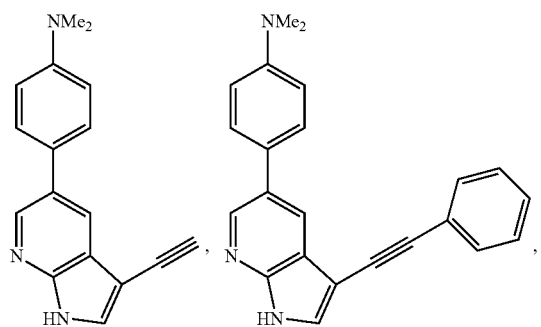

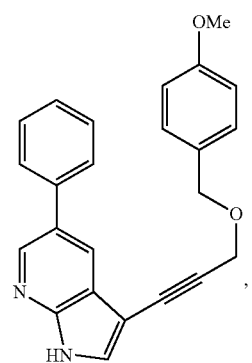

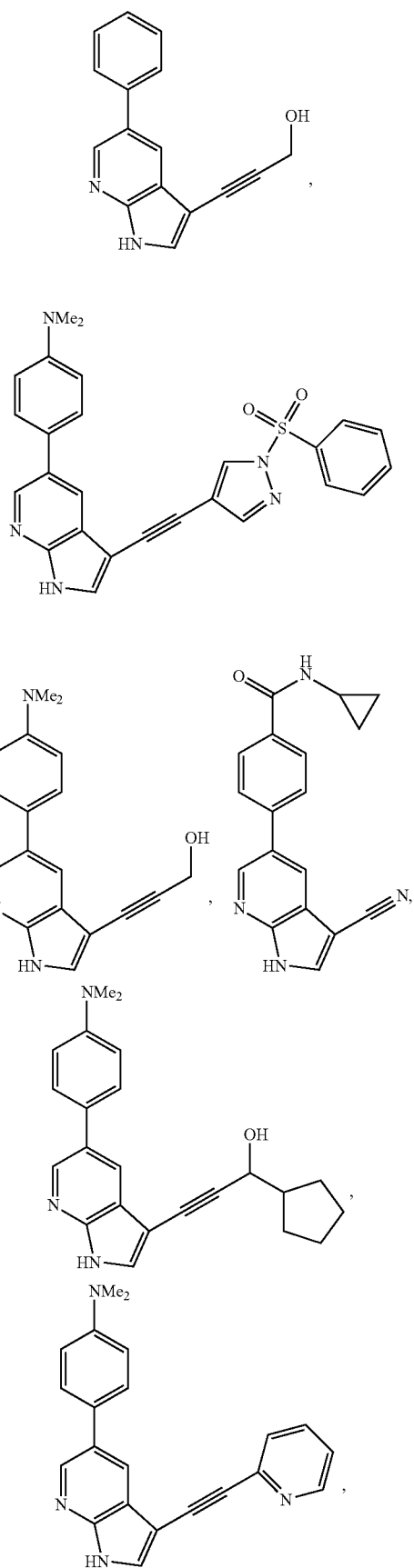

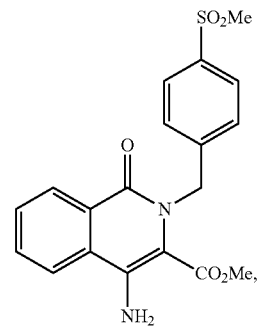

The following derivatives are contemplated for use as therapeutics in treating type I diabetes:

wherein ring A is an optionally substituted benzene ring, X is —O—, —N=, —NR³— or —CHR³—, R² is an acyl group, an optionally esterified or thioesterified carboxyl group, and optionally substituted carbamoyl group or an optionally substituted amino group and the line, a broken line shows a single bond or a double bond, and R' is a hydrogen atom, optionally substituted hydrocarbon group, and optionally substituted heterocyclic group and the like. These compounds have been described in Japanese Publication JP2004210772 and all of which or any present or future corresponding U.S. application or patent are hereby incorporated by reference. Preferred embodiments include:

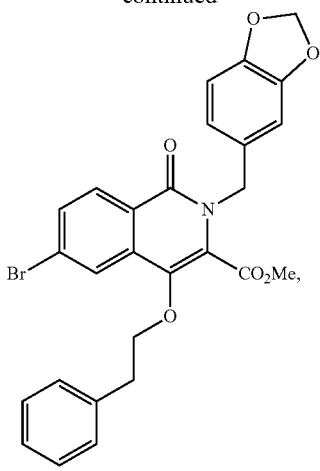

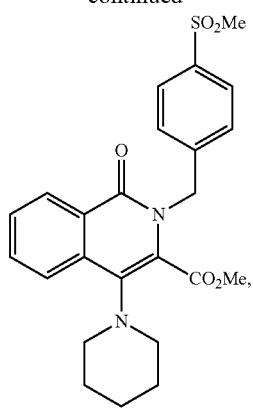

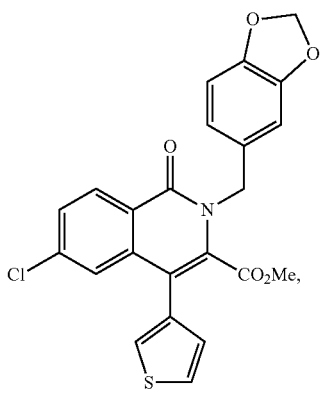

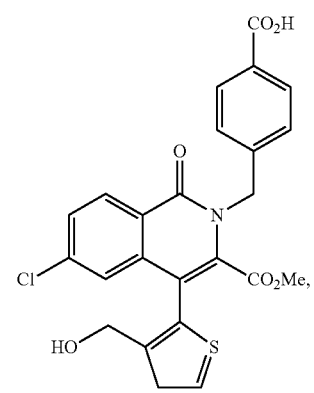

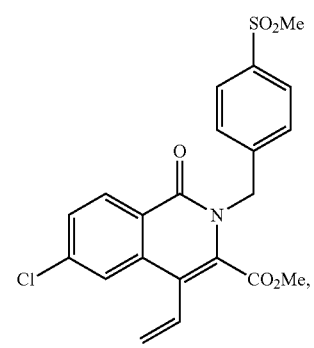

Further illustrative examples can be found in the identified reference.

The following derivatives are contemplated for use as therapeutics in treating type I diabetes:

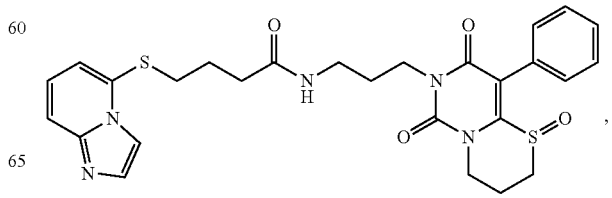

wherein each of $Ar^a$ and $Ar^b$ is an aromatic group optionally having substituents, $Ar^a$ and $Ar^b$ optionally form a condensed cyclic group together with the adjacent carbon atom; ring $B^a$ is a nitrogen-containing heterocycle optionally having substituents; $X^a$ and $Y^a$ are the same or different and each is (1) a bond, (2) an oxygen atom, (3) $S(O)_p$ (wherein p is an integer of 0 to 2), (4) $NR^d$ (wherein $R^d$ is a hydrogen atom or a lower alkyl group) or (5) a divalent linear lower hydrocarbon group optionally having substituents and containing 1 to 3 hetero atom(s); ring $A^a$ is a 5-membered ring optionally having substituents; $R^a$ and $R^b$ are the same or different and each is (1) a hydrogen atom, (2) a halogen atom, (3) a hydrocarbon group optionally having substituents, (4) an acyl group or (5) a hydroxy group optionally having a substituent; $R^c$ is (1) a hydrogen atom, (2) a hydroxy group optionally substituted by a lower alkyl group or (3) a carboxyl group. These compounds have been described in U.S. Patent Application Publication 2004/0254189 and Japanese Publication JP2004161716, all of which or any present or future corresponding U.S. application or patent are hereby incorporated by reference. Preferred embodiments include:

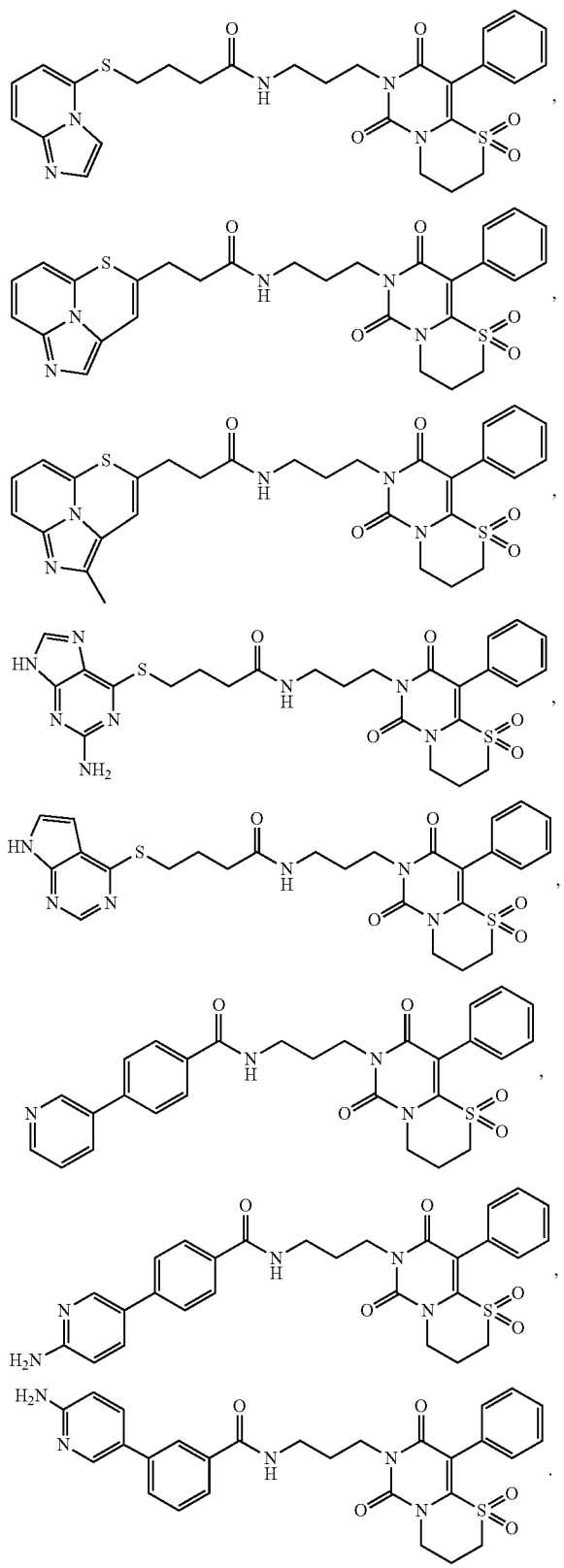
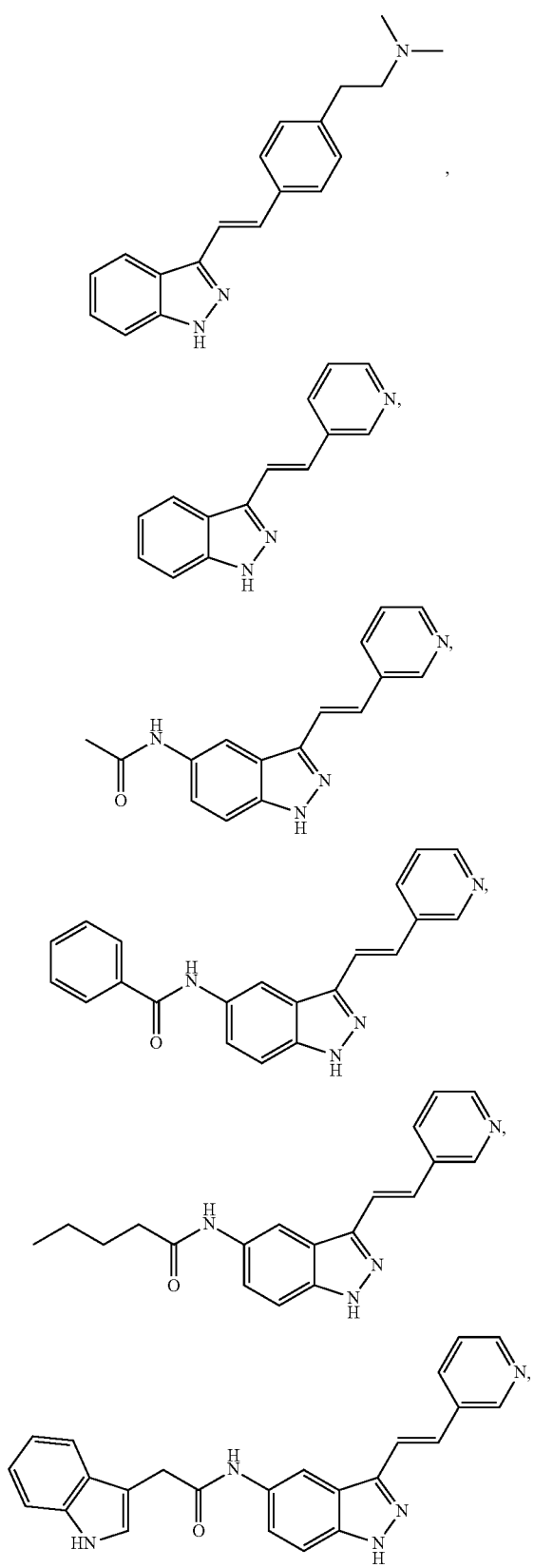
The following derivatives are contemplated for use as therapeutics in treating type I diabetes:
Further illustrative embodiments can be found in the corresponding identified references.

67
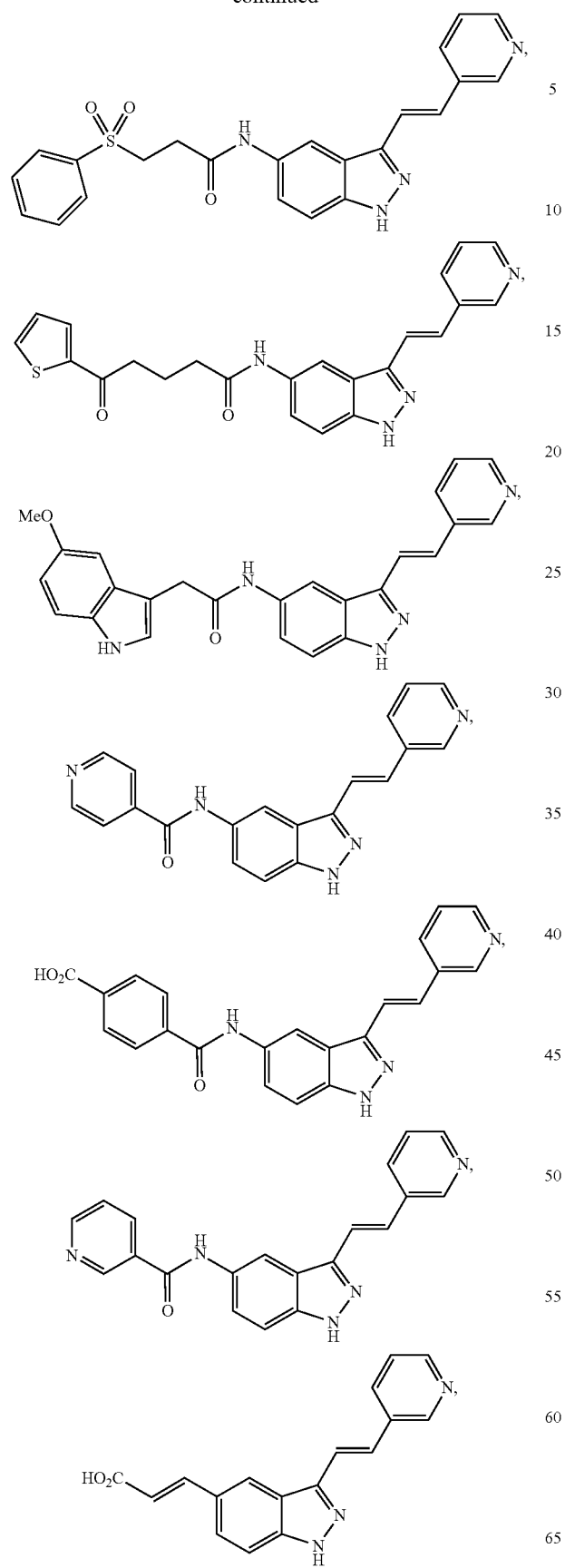
68
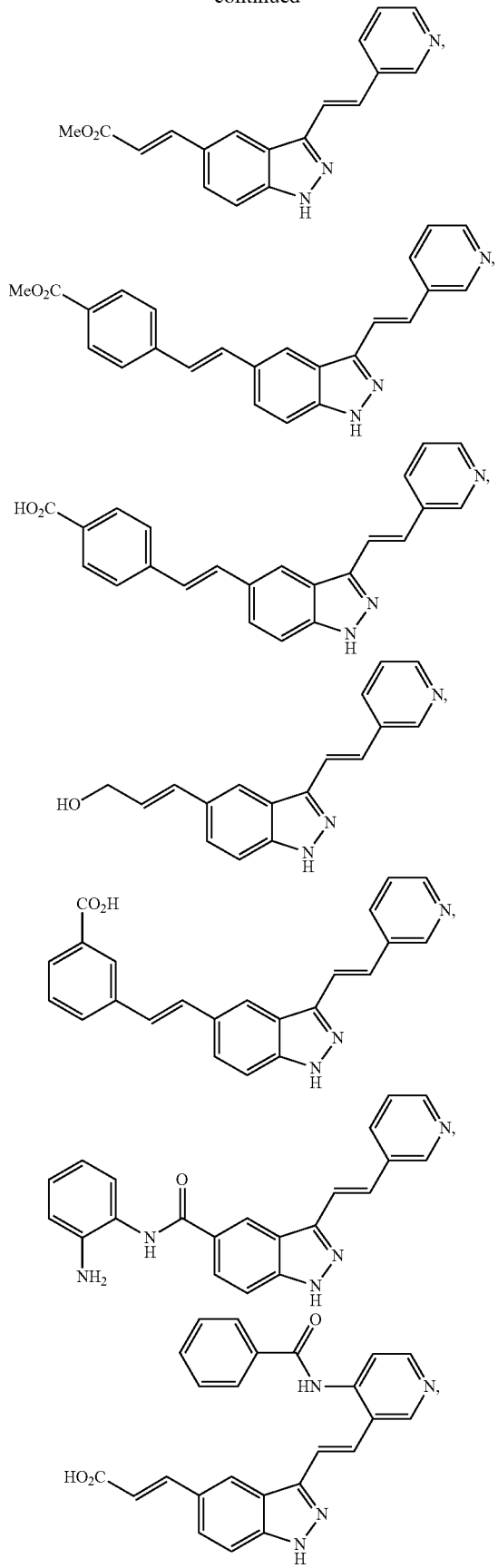

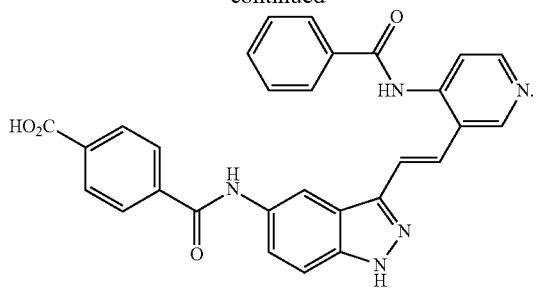

These compounds have been described in Japanese Publication JP2003015481 and all of which or any present or future corresponding U.S. application or patent are hereby incorporated by reference.

The following derivatives are contemplated for use as therapeutics in treating type I diabetes:

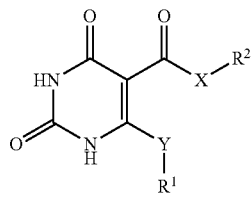

wherein Y is selected from O, NH, N(R), S, S(O) or S(O)$_2$; X is selected from O, NH or N(R); $R^1$ and $R^2$ are each independently selected from H, a $C_1$-$C_6$ straight chain or branched alkyl or alkenyl group, optionally substituted with one to four substituents, each of which is independently selected from NH$_2$, NHR, N(R)$_2$, NO$_2$, OH, OR, CF$_3$, halo, CN, CO$_2$H, CONH$_2$, CONHR, CON(R)$_2$, COR, SR, S(O)R, S(O)$_2$R, S(O)$_2$NH$_2$, S(O)$_2$NHR or R; a 5-7 membered aromatic or non-aromatic carbocyclic or heterocyclic ring, optionally substituted with one to four substituents, each of which is independently selected from NH$_2$, NHR, N(R)$_2$, NO$_2$, OH, OR, CF$_3$, halo, CN, CO$_2$H, CONH$_2$, CONHR, CON(R)$_2$, COR, SR, S(O)R, S(O)$_2$R, S(O)$_2$NH$_2$, S(O)$_2$NHR or R; or a 9-10 membered bicyclic aromatic or non-aromatic carbocyclic or heterocyclic ring optionally substituted with one to four substituents, each of which is independently selected from NH$_2$, NHR, N(R)$_2$, NO$_2$, OH, OR, CF$_3$, halo, CN, CO$_2$H, CONH$_2$, CONHR, CON(R)$_2$, COR, SR, S(O)R, S(O)$_2$R, S(O)$_2$NH$_2$, S(O)$_2$NHR or R; wherein said heterocyclic ring contains 1 to 4 heteroatoms, each of which heteroatoms are independently selected from N, O, S, SO or SO$_2$; and R is selected from a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system. These compounds have been described in U.S. Patent Application Publication 2003/100549 and all of which or any present or future corresponding U.S. application or patent are hereby incorporated by reference. Preferred embodiments include:

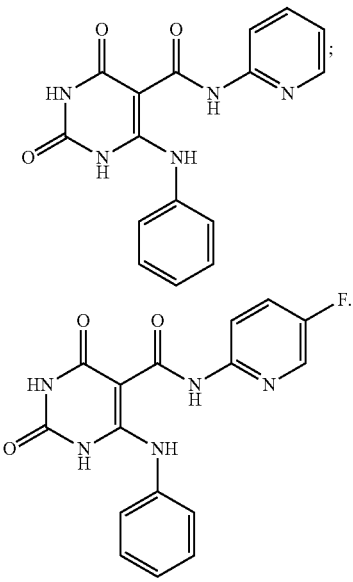

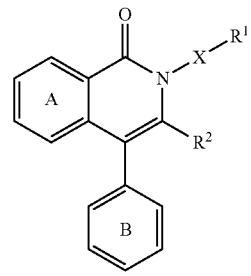

Further illustrative embodiment can be found in the corresponding identified reference.

The following derivatives are contemplated for use as therapeutics in treating type I diabetes:

wherein ring A and ring B are each an optionally substituted benzene ring, X is —O—, —N=, —NR$^3$— or —CHR$^3$—, R$^2$ is an acyl group, an optionally esterified or thioesterified carboxyl group, and optionally substituted carbamoyl group or an optionally substituted amino group and the line, a broken line shows a single bond or a double bond, and R$^1$ is a hydrogen atom, optionally substituted hydrocarbon group, and optionally substituted heterocyclic group and the like. These compounds have been described in International Publication Number WO 2003/068750 and all of which or any present or future corresponding U.S. application or patent are hereby incorporated by reference. Preferred embodiments include:

2-(benzo[1,3]dioxol-5-ylmethyl)-6-bromo-1-oxo-4-phenyl-1,2-dihydroisoquinoline-3-carboxylic acid methyl ester;

6-bromo-1-oxo-4-phenyl-2-(4-sulfamoylbenzyl)-1,2-dihydroisoquinoline-3-carboxylic acid methyl ester;

6-bromo-2-(4-methanesulfonylbenzyl)-1-oxo-4-phenyl-1,2-dihydroisoquinoline-3-carboxylic acid methyl ester;

6-bromo-2-(4-carboxylbenzyl)-1-oxo-4-phenyl-1,2-dihydroisoquinoline-3-carboxylic acid methyl ester;

2-(2-acetylpiperidin-4-ylmethyl)-6-bromo-1-oxo-4-phenyl-1,2-dihydroisoquinoline-3-carboxylic acid methyl ester;

6-bromo-2-[4-(3-carboxylpropionylamino)benzyl]-1-oxo-4-phenyl-1,2-dihydroisoquinoline-3-carboxylic acid methyl ester;

6-bromo-1-oxo-4-phenyl-2-[4-(2-(pyrrolidini-1-yl)ethylcarbamoyl)benzyl]-1,2-dihydroisoquinoline-3-carboxylic acid methyl ester;
6-amino-2-(benzo[1,3]dioxol-5-ylmethyl)-1-oxo-4-phenyl-1,2-dihydroisoquinoline-3-carboxylic acid methyl ester;
6-bromo-2-(4-methanesulfonylbenzyl)-4-phenyl-3-propionyl-2H-isoquinolin-1-one;
6-bromo-2-[4-(N',N'-diethylhydrazinocarbonyl)benzyl]-1-oxo-4-phenyl-1,2-dihydroisoquinoline-3-carboxylic acid methyl ester;
3-acetyl-6-bromo-4-phenyl-2-(4-sulfamoylbenzyl)-2H-isoquinolin-1-one;
4-(6-chloro-3-butyryl-1-oxo-4-phenyl-1H-isoquinolin-2-ylmethyl)benzenesulfonamide;
4-(6-bromo-1-oxo-4-phenyl-3-propionyl-1H-isoquinolin-2-ylmethyl)benzoic acid;
4-(6-chloro-1-oxo-4-phenyl-3-propionyl-1H-isoquinolin-2-ylmethyl)benzoic acid;
6-bromo-4-phenyl-3-propionyl-2-[4-(1H-tetrazol-5-yl)benzyl]-2H-isoquinolin-1-one; and
3-[(2Z)-3-aminobut-2-enoyl]-6-bromo-2-(4-methanesulfonylbenzyl)-4-phenyl-2H-isoquinolin-1-one. Further illustrative embodiments can be found in the identified reference(s).

The following derivatives are contemplated for use as therapeutics in treating type I diabetes:

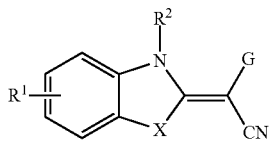

wherein X is O, S or $NR^O$, with $R^O$ being H or an unsubstituted or substituted $C_1$-$C_6$ alkyl; G is an unsubstituted or substituted pyrimidinyl group; $R^1$ is selected from the group comprising or consisting of hydrogen, unsubstituted or substituted $C_1$-$C_6$-alkoxy, unsubstituted or substituted $C_1$-$C_6$-thioalkoxy, unsubstituted or substituted $C_1$-$C_6$-alkyl, unsubstituted or substituted $C_2$-$C_6$-alkenyl unsubstituted or substituted $C_2$-$C_6$-alkynyl, primary, secondary or tertiary amino groups, aminoacyl, aminocarbonyl, unsubstituted or substituted $C_1$-$C_6$ alkoxycarbonyl unsubstituted or substituted aryl, unsubstituted or substituted heteroaryl, carboxyl, cyano, halogen, hydroxy, nitro, sulfoxy, sulfonyl sulfonamide, unsubstituted or substituted hydrazides; $R^2$ is selected from the group comprising or consisting of hydrogen, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkyl-aryl, unsubstituted or substituted aryl or heteroaryl unsubstituted or substituted $C_1$-$C_6$-alkyl-heteroaryl, —C(O)—$OR^3$, —C(O)—$R^3$, —C(O)—$NR^3R^{3'}$, —($SO_2$)$R^3$, with $R^3$ and $R^{3'}$ being independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alknyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl. These compounds have been described in U.S. Patent Application Publication 2003/0162794 and all of which or any present or future corresponding U.S. application or patent are hereby incorporated by reference. Preferred embodiments include:
1,3-benzothiazol-2-yl(2-chloro-4-pyrimidinyl)-acetonitrile;
1,3-benzothiazol-2-yl[2-methylsulfanyl)-4-pyrimidinyl]acetonitrile;
1,3-benzothiazol-2-yl(2-{[2-(1H-imidazolyl-4-yl)ethyl-1]amino}-4-pyrimidinyl)acetonitrile;
1,3-benzothiazol-2-yl[2-(methylamino)-4-pyrimidinyl]acetonitrile;
1,3-benzothiazol-2-yl{2-[(2-hydroxyethyl)amino]-4-pyrimidinyl}acetonitrile;
1,3-benzothiazol-2yl[2-(benzyloxy)pyrimidin-4-yl]acetonitrile;
1,3-benzothiazol-2-yl[2-(4-methoxyphenoxy)pyrimidin-4-yl]acetonitrile; and
1,3-benzothiazol-2-yl(2-methoxy-4-pyrimidinyl)-acetonitrile. Further illustrative embodiments can be found in the identified reference.

The following derivatives are contemplated for use as therapeutics in treating type I diabetes:

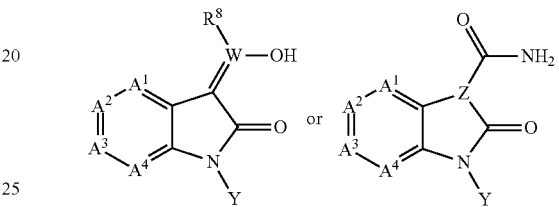

wherein Y is selected from —($CH_2$)-$Q^1$; —(CO)-$Q^1$; —(CO)NH-$Q^1$; —(CO)—O-$Q^1$; —($SO_2$)-$Q^1$ or —($SO_2$)NH-$Q^1$; $Q^1$ is a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring system, wherein said alkyl, alkenyl, ring or ring system is optionally substituted with one to four substituents, each of which is independently selected from $NH_2$, NH—R, N(R)$_2$, $NO_2$, OH, OR, $CF_3$, halo, CN, $CO_2H$, C(O)—$NH_2$, C(O)—NH—R, C(O)—N(R)$_2$, C(O)—R, SR, S(O)—R, S(O)$_2$—R, S(O)$_2$—NH—R or —R; W is N or C; wherein when W is N, $R^8$ is a lone pair of electrons; and wherein when W is C, $R^8$ is $R^7$. $A^1$ is N or $CR^1$; $A^2$ is N or $CR^2$; $A^3$ is N or $CR^3$; $A^4$ is N or $CR^4$; provided that at least one of $A^1$, $A^2$, $A^3$ and $A^4$ must not be N; $R^1$ is —$NHR^5$, —$OR^5$, —$SR^5$, or —$R^5$; $R^2$, $R^3$, and $R^4$ are independently selected from —(CO)$NH_2$, —(CO)NHR, —(CO)N(R)$_2$, —$NHR^5$, —$NHCH_2R^5$, —$OR^5$, —$SR^5$, —$R^5$, —NH(CO)—$R^6$, —NH(CO)—$NHR^6$, —NH(CO)—NH(CO)$R^6$, —NH(CO)—$OR^6$, —NH($SO_2$)—$R^6$, —NH($SO_2$)—$NHR^6$, —C(O)OH, —C(O)OR, —(CO)-$Q^1$, —(CO)NH-$Q^1$, —(CO)NR-$Q^1$, —(CO)—O-$Q^1$, —($SO_2$)-$Q^1$ or —($SO_2$)NH-$Q^1$; $R^5$ and $R^6$ are each independently selected from H; N(R)$_2$, NHOH, $NO_2$, C(O)OR or halo; a $C_1$-$C_6$ straight chain or branched alkyl, alkenyl or alkynyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, NHR, NHC(O)OR, N(R)$_2$, $NO_2$, OH, OR, $CF_3$, halo, CN, Si(R)$_3$, CO2H, COOR, $CONH_2$, CONHR, CON(R)$_2$, COR, SR, S(O)R, S(O)$_2$R, S(O)$_2$NHR or R; $R^7$ is H; a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, NHR, N(R)$_2$, NO$_2$, OH, OR, CF$_3$, halo, CN, CO$_2$H, CONH$_2$, CONHR, CON(R)$_2$, COR, SR, S(O)R, S(O)$_2$R, S(O)$_2$NHR or R; R is a C$_1$-C$_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system; and Z is CH or N. These compounds have been described in U.S. Patent Application Publication 2003/0162794 and all of which or any present or future corresponding U.S. application or patent are hereby incorporated by reference. Preferred embodiments include:

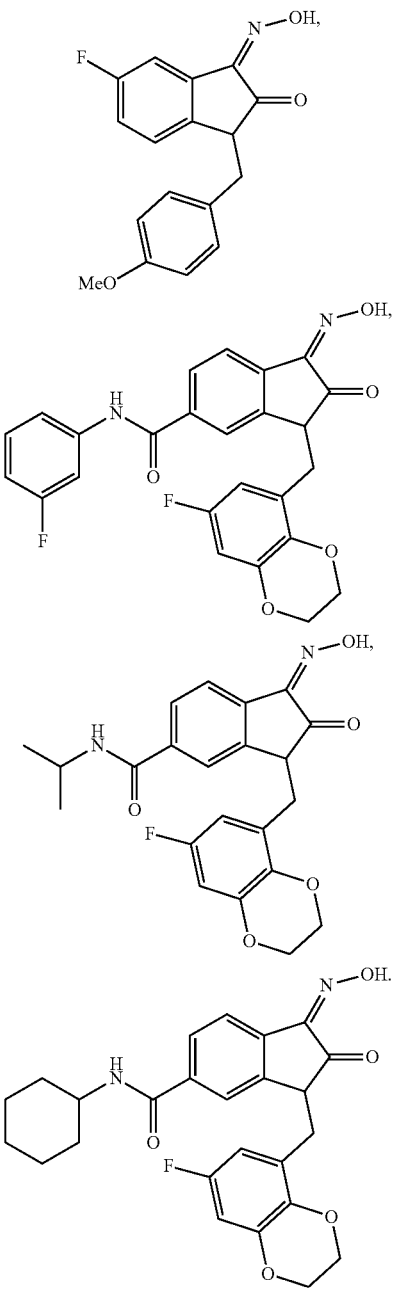

Further illustrative embodiments can be located in the identified reference.

The following derivatives are contemplated for use as therapeutics in treating type I diabetes:

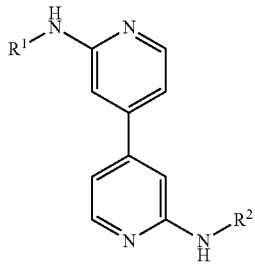

wherein: R$^1$ is aryl or heteroaryl, each of which is optionally substituted with one or more of R$^3$, OR$^3$, OCOR$^3$, COOR$^3$, COR$^3$, CON$^4$R$^3$R$^4$, NHCOR$^3$, NR$^3$R$^4$, NHSO$_2$R$^3$, SO$_2$R$^3$, SO$_2$NR$^3$R$^4$, SR$^3$, CN, halogeno and NO$_2$; R$^2$ is R$^5$, R$^6$, COR$^5$, COR$^5$, CONHR$^5$, CONHR$^6$, CON(R$^6$)$_2$, COOR$^5$, COOR$^6$, SO$^2$R$^5$ or SO$_2$R$^6$; R$^3$ and R$^4$ are each independently hydrogen, C$_{1-6}$ alkyl, C$_{2-6}$ alkenyl, C$_{2-6}$ alkynyl, C$_{3-8}$ cycloalkyl, (C$_{3-8}$ cycloalkyl) C$_{1-6}$ alkyl, heterocycle, heterocycle C$_{1-6}$ alkyl, C$_{1-6}$ fluoroalkyl, C$_{1-6}$ trifluoroalkoxyl; R$^5$ is aryl or heteroaryl, each of which is optionally substituted with one or more of R$^7$, OR$^7$, OCOR$^7$, COOR$^7$, COR$^7$, CONR$^7$R$^8$, CONHOR$^7$, NHCOR$^7$, NR$^7$R$^8$, NHSO$_2$R$^7$, SO$_2$R$^7$, SO$_2$NHR$^7$R$^8$, SR$^7$, R$^7$SR$^8$, CN, halogeno, oxygen and NO$_2$; R$^6$ is hydrogen, C$_{1-6}$ alkyl, C$_{3-8}$ cycloalkyl, (C$_{3-8}$ cycloalkyl) C$_{1-6}$ alkyl, heterocycle, heterocycle C$_{1-6}$ alkyl, heteroaryl C$_{1-6}$ alkyl; aryl C$_{1-6}$ alkyl, C$_{1-6}$ alkoxyl, or C$_{2-6}$ alkenyl, wherein any of C$_{1-6}$ alkyl, C$_{3-8}$ cycloalkyl, (C$_{3-8}$ cyclolakyl) C$_{1-6}$ alkyl, heterocycle, heterocycle C$_{1-6}$ alkyl, heteronaryl C$_{1-6}$ alkyl, aryl C$_{1-6}$ alkyl, C$_{1-6}$ alkoxyl and C$_{2-6}$ alkenyl is optionally substituted with one or more A; R$^7$ and R$^8$ are each independently hydrogen, C$_{1-6}$ alkyl, C$_{3-8}$ cycloalkyl, (C$_{3-8}$ cycloalkyl) C$_{1-6}$ alkyl, C$_{2-6}$ alkenyl, aryl, heteroaryl, heteroaryl C$_{1-6}$ alkyl, heterocycle, heterocycle C$_{1-6}$ alkyl, aryl, C$_{1-6}$ fluoroalkyl and C$_{1-6}$ chloroalkyl, wherein any of C$_{1-6}$ alkyl, C$_{3-8}$ cycloalkyl, (C$_{3-8}$ cycloalkyl) C$_{1-6}$ alkyl, C$_{2-6}$ alkenyl, heteroaryl, heteroaryl C$_{1-6}$ alkyl, heterocycle and heterocycle C$_{1-6}$ alkyl is optionally substituted with one or more B; R$^9$ and R$^{10}$ are each independently hydrogen, C$_{1-6}$ alkyl, C$_{3-8}$ cycloalkyl, (C$_{3-8}$ cycloalkyl) C$_{1-6}$ alkyl, C$_{2-6}$ alkenyl, heterocycle, heterocycle C$_{1-6}$ alkyl, heteroaryl, heteroaryl C$_{1-6}$ alkyl, aryl or aryl C$_{1-6}$ alkyl, wherein any of C$_{1-6}$ alkyl, C$_{3-8}$ cycloalkyl, (C$_{3-8}$ cycloalkyl) C$_{1-6}$ alkyl, C$_{2-6}$ alkenyl, heterocycle, heterocycle C$_{1-6}$ alkyl, heteroaryl, heteroaryl C$_{1-6}$ alkyl, aryl or aryl C$_{1-6}$ alkyl is optionally substituted with one or more B; A is R$^9$, OR$^9$, OCOR$^9$, COOR$^S$, COR$^S$, CONR$^9$R$^{10}$, CONHOR$^9$, NHCOR$^9$, NR$^9$R$^{10}$, NR$^9$SO$_2$R$^{10}$, SO$_2$R$^9$, SO$_2$NR$^9$R$^{10}$, SR$^9$, R$^9$SR$^{10}$, CN or halogen; B is C$_{1-6}$ alkyl, C$_{1-6}$ alkoxy, C$_{1-6}$ alkylamino, di (C$_{1-6}$ alkyl)amino or halogen. These compounds have been described in International Publication Number WO 2004/101565 and all of which or any present or future corresponding U.S. application or patent are hereby incorporated by reference. Preferred embodiments include:

N,N'-Bis[4-(trifluoromethyl)phenyl]-4,4'-bipyridine-2,2'-diamine;
N,N'-Bis(4-fluorophenyl)-4,4'-bipyridine-2,2'-diamine;
N,N'-Bis(3,4-difluorophenyl)-4,4'-bipyridine-2,2'-diamine;
N,N'-Bis[3-(trifluoromethyl)phenyl]-4,4'-bipyridine-2,2'-diamine;
N,N'-Bis[3-(trifluoromethyl)phenyl]-4,4'-bipyridine-2,2'-diamine;
N,N'-Bis(2-fluorophenyl)-4,4'-bipyridine-2,2'-diamine;

N,N'-Bis(2-methylphenyl)-4,4'-bipyridine-2,2'-diamine;
N,N'-Bis(2-aminophenyl)-4,4'-bipyridine-2,2'-diamine;
N,N'-Bis(2-methoxyphenyl)-4,4'-bipyridine-2,2'-diamine;
N,N'-Bis(2-ethoxyphenyl)-4,4'-bipyridine-2,2'-diamine;
N-(2'-anilino-4,4-bipyridin-2-yl)trans-4-methoxycyclohexanecarboxamide;
N (2'-anilino-4,4'-bipyridin-2-yl)-cis-4-methoxycyclohexanecarboxamide;
N-12'-[(4-fluorophenyl)amino]-4,4'-bipyridin-2-yl}-trans-4-methoxy-cyclohexanecarboxamide;
N-{2'-[(4-fluorophenyl)amino]-4,4'-bipyridin-2-yl}-cis-4-methoxy-cyclohexanecarboxamide;
N-(6-methylpyridin-2-yl)-N-phenyl-4,4'-bipyridine-2,2'-diamine; N-phenyl-N-pyridin-2-yl-4,4'-bipyridine-2,2'-diamine;
{4-[(4-methylpiperazin-1-yl) sulfonyl]phenyl}-N-phenyl-4,4'-bipyridine-2,2'-diamine;
N-phenyl-N'-pyridin-3-yl-4,4'-bipyridine-2,2'-diamine;
N-phenyl-N'-pyrimidin-2-yl-4,4'-bipyridine-2,2'-diamine;
N-phenyl-N'-pyrimidin-5-yl-4,4'-bipyridine-2,2'-diamine;
(2E)-1-{4-[(2'-anilino-4,4'-bipyridin-2-yl)amino]phenyl}-3-(dimethylamino)prop-2-en-1-one;
4-[(2'-anilino-4,4'-bipyridin-2-yl)amino]-N-(2-pyrrolidin-1-ylethyl)benzenesulfonamide;
4-[(2'-anilino-4,4'-bipyridin-2-yl)amino]-N-(2-morpholin-4-ylethyl)benzenesulfonamide;
N-{4-[(4-ethylpiperazin-1-yl)sulfonyl]phenyl}-N'-phenyl-4,4'-bipyridine-2,2'-diamine;
N-phenyl-N'-pyridin-4-yl-4,4'-bipyridine-2,2'-diamine;
N-(2'-anilino-4,4'-bipyridin-2-yl)tetrahydrofuran-3-carboxamide;
N-(2'-anilino-4,4'-bipyridin-2-yl)-3-piperidin-1-ylpropanamide;
N-(2'-anilino-4,4'-bipyridin-2-yl) tetrahydrofuran-3-carboxamide;
N-(2'-anilino-4,4'-bipyridin-2-yl)nicotinamide;
N-(2'-anilino-4,4'-bipyridin-2-yl)-4-(dimethylamino) benzamide;
N-(2'-anilino-4,4'-bipyridin-2-yl)-2,6-dimethoxynicotinamide;
N-(2'-anilino-4,4'-bipyridin-2-yl)-1H-indole-2-carboxamide;
N-(2'-anilino-4,4'-bipyridin-2-yl)pyridine-2-carboxamide;
N-(2'-anilino-4,4'-bipyridin-2-yl)-3-furamide;
N-(2'-anilino-4,4'-bipyridin-2-yl)-1,2,3-thiadiazole-4-carboxamide;
N-(2'-anilino-4,4'-bipyridin-2-yl) isoxazole-5-carboxamide;
N-(2'-anilino-4,4'-bipyridin-2-yl)-5-methylisoxazole-3-carboxamide;
N-(2'-anilino-4,4'-bipyridin-2-yl)pyrazine-2-carboxamide;
N-(2'-anilino-4,4'-bipyridin-2-yl)-1-methyl-1H-imidazole-4-carboxamide;
N-(2'-anilino-4,4'-bipyridin-2-yl)-2-furamide;
N-(2'-anilino-4,4'-bipyridin-2-yl)-4-methoxybenzamide;
N-(2'-anilino-4,4'-bipyridin-2-yl)-5-bromo-2-furamide;
N-(2'-anilino-4,4'-bipyridin-2-yl)-2-(methylthio)nicotinamide;
Methyl-4-{[(2'-anilino-4,4'-bipyridin-2-yl)amino] carbonyl}benzoate;
3-(acetylamino)-N-(2'-anilino-4,4'-bipyridin-2-yl)benzamide;
N-(2'-anilino-4,4'-bipyridin-2-yl)-4-oxo-4,5,6,7-tetrahydro-1-benzofuran-3-carboxamide;
N-(2'-anilino-4,4'-bipyridin-2-yl)-5-[(pyridin-2-ylthio) methyl]-2-furamide;
N-(2'-anilino-4,4'-bipyridin-2-yl)nicotinamide 1-oxide;
N-(2'-anilino-4,4'-bipyridin-2-yl)-3-hydroxypyridine-2-carboxamide;
N-(2'-anilino-4,4'-bipyridin-2-yl)-6-bromopyridine-2-carboxamide;
N-(2'-anilino-4,4'-bipyridin-2-yl)isonicotinamide 1-oxide;
N-(2'-anilino-4,4'-bipyridin-2-yl)-2-hydroxynicotinamide;
N-(2'-anilino-4,4'-bipyridin-2-yl)-6-hydroxypyridine-2-carboxamide;
N-(2'-anilino-4,4'-bipyridin-2-yl)-3-benzoylpyridine-2-carboxamide;
N-(2'-anilino-4,4'-bipyridin-2-yl)-6-methylpyridine-2-carboxamide;
N-(2'-anilino-4,4'-bipyridin-2-yl)-3,5-dimethylisoxazole-4-carboxamide;
N-(2'-anilino-4,4'-bipyridin-2-yl)-2-methoxynicotinamide;
N-(2'-anilino-4,4'-bipyridin-2-yl)-4-methyl-1,2,3-thiadiazole-5-carboxamide;
N-(2'-anilino-4,4'-bipyridin-2-yl)-2-chloroisonicotinamide;
N-(2'-anilino-4,4'-bipyridin-2-yl)-5-methylisoxazole-4-carboxamide;
N-(2'-anilino-4,4'-bipyridin-2-yl)-3-methylisoxazole-4-carboxamide;
N-(2'-anilino-4,4'-bipyridin-2-yl)-1-methyl-1H-pyrrole-2-carboxamide;
N-(2'-anilino-4,4'-bipyridin-2-yl)-2-chloronicotinamide;
N-(2'-anilino-4,4'-bipyridin-2-yl)-5-chloro-1H-indole-2-carboxamide;
N-(2'-anilino-4,4'-bipyridin-2-yl)-4-chloro-1H-pyrazole-3-carboxamide;
N-(2'-anilino-4,4'-bipyridin-2-yl)-5-methyl-1H-pyrazole-3-carboxamide;
(2E)-N-(2'-anilino-4,4'-bipyridin-2-yl)-3-(3-furyl)acrylamide;
N-(2'-anilino-4,4'-bipyridin-2-yl)-3-(2-oxo-1,3-benzoxazol-3(2H)-yl) propanamide;
N'-(2'-anilino-4,4'-bipyridin-2-yl)-N,N-dimethylsuccinamide;
N-(2'-anilino-4,4'-bipyridin-2-yl)-2-[(4-chlorophenyl) sulfonyl]acetamide;
N-(2'-anilino-4,4'-bipyridin-2-yl)-5-oxoprolinamide;
N-(2'-anilino-4,4'-bipyridin-2-yl)-3-methoxypropanamide;
N-(2'-anilino-4,4'-bipyridin-2-yl)-4-methoxycyclohexanecarboxamide;
N-(2'-anilino-4,4'-bipyridin-2-yl)-3-methoxypropanamide;
N-(2'-anilino-4,4'-bipyridin-2-yl) tetrahydrofuran-3-carboxamide;
N-(2'-anilino-4,4'-bipyridin-2-yl)-4-(dimethylamino) butanamide;
N-(2'-anilino-4,4'-bipyridin-2-yl)nicotinamide;
N-(2'-anilino-4,4'-bipyridin-2-yl)-4-(dimethylamino) benzamide;
N-(2'-anilino-4,4'-bipyridin-2-yl)-2,6-dimethoxynicotinamide;
N-(2'-anilino-4,4'-bipyridin-2-yl)-1H-indole-2-carboxamide;
N-(2'-anilino-4,4'-bipyridin-2-yl)-5-methylpyrazine-2-carboxamide;
N-(2'-anilino-4,4'-bipyridin-2-yl)pyridine-2-carboxamide;
N-(2'-anilino-4,4'-bipyridin-2-yl)-3-furamide; N (2'-anilino-4,4'-bipyridin-2-yl)-N-phenylurea;
N-(2'-anilino-4,4'-bipyridin-2-yl)-N'-phenylurea;
N-(2'-anilino-4,4'-bipyridin-2-yl)-N'-[1-(4-bromophenyl) ethyl]urea;
N-(2'-anilino-4,4'-bipyridin-2-yl)-N'-thien-3-ylurea; N-(2'-anilino-4,4'-bipyridin-2-yl)-N'-(2-methylphenyl)urea;

N-(2'-anilino-4,4'-bipyridin-2-yl)-N'-(4-methylphenyl)urea;
N-(2'-anilino-4,4'-bipyridin-2-yl)-N'-(3-fluorophenyl) urea;
N-(2'-anilino-4,4'-bipyridin-2-yl)-N'-(2-fluorophenyl)urea;
N-(2'-anilino-4,4'-bipyridin-2-yl)-N'-(4-fluorophenyl)urea;
N-(2'-anilino-4,4'-bipyridin-2-yl)-N'-[4-(chloromethyl)phenyl]urea;
N-(2'-anilino-4,4'-bipyridin-2-yl)-N-(3-cyanophenyl)urea;
N-(2'-anilino-4,4'-bipyridin-2-yl)-N'-(4-cyanophenyl)urea;
N-(2'-anilino-4,4'-bipyridin-2-yl)-N'-(2-cyanophenyl)urea;
N-(2'-anilino-4,4'-bipyridin-2-yl)-N'-(2,3-dimethylphenyl) urea;
N-(2'-anilino-4,4'-bipyridin-2-yl)-N'-(2,5-dimethylphenyl) urea;
N-(2'-anilino-4,4'-bipyridin-2-yl)-N'-(4-ethylphenyl)urea;
N-(2'-anilino-4,4'-bipyridin-2-yl)-N'-(3-ethylphenyl)urea;
N-(2'-anilino-4,4'-bipyridin-2-yl)-N'-(4-methoxyphenyl) urea;
N-(2'-anilino-4,4'-bipyridin-2-yl)-N'-(3-methoxyphenyl) urea;
N-(2'-anilino-4,4'-bipyridin-2-yl)-N'-(2-methoxyphenyl) urea;
N-(2'-anilino-4,4'-bipyridin-2-yl)-N'-(5-fluoro-2-methylphenyl)urea;
N-(2'-anilino-4,4'-bipyridin-2-yl)-N'-(2-fluorobenzyl)urea;
N-(2'-anilino-4,4'-bipyridin-2-yl)-N'-(2-fluoro-5-methylphenyl)urea;
N-(2'-anilino-4,4'-bipyridin-2-yl)-N'-(3-fluorobenzyl)urea;
N-(2'-anilino-4,4'-bipyridin-2-yl)-N'-(2-chlorophenyl)urea;
N-(2'-anilino-4,4'-bipyridin-2-yl)-N'-(3-chlorophenyl)urea;
N-(2'-anilino-4,4'-bipyridin-2-yl)-N'-(2-chlorobenzyl)urea;
N-(2'-anilino-4,4'-bipyridin-2-yl)-N'-(2,5-difluorophenyl) urea;
N-(2'-anilino-4,4'-bipyridin-2-yl)-N'-(2,4-difluorophenyl) urea;
N-(2'-anilino-4,4'-bipyridin-2-yl)-N'-(3,4-dichlorobenzyl) urea;
N-(4-acetylphenyl)-N'-(2'-anilino-4,4'-bipyridin-2-yl)urea;
N-(3-acetylphenyl)-N'-(2'-anilino-4,4'-bipyridin-2-yl)urea;
N-(T-anilino-4,4'-bipyridin-2-yl)-N'-(4-isopropylphenyl) urea;
N-(2'-anilino-4,4'-bipyridin-2-yl)-N'-(2-isopropylphenyl) urea;
N-(2'-anilino-4,4'-bipyridin-2-yl)-N'-(2-ethyl-6-methylphenyl)urea;
N-(2'-anilino-4,4'-bipyridin-2-yl)-N'-mesitylurea;
N-(2'-anilino-4,4'-bipyridin-2-yl)-N'-(2-propylphenyl)urea;
N-(T-anilino-4,4'-bipyridin-2-yl)-N'-[4-(dimethylamino) phenyl]urea;
N-(2'-anilino-4,4'-bipyridin-2-yl)-N'-1,3-benzodioxol-5-ylurea;
N-(2'-anilino-4,4'-bipyridin-2-yl)-N'-(4-methoxy-2-methylphenyl)urea;
N-(2'-anilino-4,4'-bipyridin-2-yl)-N'-(2-methoxy-5-methylphenyl)urea;
N-(2'-anilino-4,4'-bipyridin-2-yl)-N'-(4-ethoxyphenyl)urea;
N-(2'-anilino-4,4'-bipyridin-2-yl)-N'-(4-methoxybenzyl) urea;
N-(2'-anilino-4,4'-bipyridin-2-yl)-N'-(4-nitrophenyl)urea;
N-(2'-anilino-4,4'-bipyridin-2-yl)-N'-(3-nitrophenyl)urea;
N-(2'-anilino-4,4'-bipyridin-2-yl)-N'-[3-(methylthio) phenyl]urea;
N-(2'-anilino-4,4'-bipyridin-2-yl)-N'-[4-(methylthio) phenyl]urea;
N-(2'-anilino-4,4'-bipyridin-2-yl)-N'-(2-methylbenzyl)urea;
N-(2'-anilino-4,4'-bipyridin-2-yl)-N'-(5-chloro-2-methylphenyl)urea;
N-(2'-anilino-4,4'-bipyridin-2-yl)-N'-(2-chloro-5-methylphenyl)urea;
N-(2'-anilino-4, (2-chlorobenzyl)urea;
N-(2'-anilino-4,4'-bipyridin-2-yl)-N'-(3-chloro-4-fluorophenyl)urea;
N-(2'-anilino-4,4'-bipyridin-2-yl)-N'-(2,3,4-trifluorophenyl) urea;
N-(2'-anilino-4,4'-bipyridin-2-yl)-N'-(4-butylphenyl)urea;
N-(T-anilino-4,4'-bipyridin-2-yl)-N'-(2-isopropyl-6-methylphenyl)urea;
N-(2'-anilino-4,4'-bipyridin-2-yl)-N'-(2-tert-butylphenyl) urea;
methyl 4-({[(2'-anilino-4,4'-bipyridin-2-yl)amino] carbonyl}amino) benzoate;
N-(2'-anilino-4,4'-bipyridin-2-yl)-N'-(3,4-dimethoxyphenyl)urea;
N-(T-anilino-4,4'-bipyridin-2-yl)-N'-(3,5-dimethoxyphenyl) urea;
N-(2'-anilino-4, (3-chloro-4-methoxyphenyl)urea;
N-(2'-anilino-4,4'-bipyridin-2-yl)-N-[4-(difluoromethoxy) phenyl]urea;
N-(2'-anilino-4,4'-bipyridin-2-yl)-N'4-[2-(trifluoromethyl) phenyl]urea;
N-(2'-anilino-4,4'-bipyridin-2-yl)-N-[3-(trifluoromethyl) phenyl]urea;
N-(2'-anilino-4,4'-bipyridin-2-yl)-N'-[4-(trifluoromethyl) phenyl]urea;
N-(2'-anilino-4,4'-bipyridin-2-yl)-N'-(2,5-dichlorophenyl) urea;
N-(2'-anilino-4,4'-bipyridin-2-yl)-N'-(3,5-dichlorophenyl) urea;
N-(2'-anilino-4,4'-bipyridin-2-yl)-N'-(3,4-dichlorophenyl) urea;
N-(2'-anilino-4,4'-bipyridin-2-yl)-N'-(2,3-dichlorophenyl) urea;
N-(2'-anilino-4,4'-bipyridin-2-yl)-N'-(2,4-dichlorophenyl) urea;
N-(2'-anilino-4,4'-bipyridin-2-yl)-N'-(4-bromo-3-methylphenyl)urea;
N-(2'-anilino-4,4'-bipyridin-2-yl)-N'-(2,6-dichloropyridin-4-yl)urea;
N-(2'-anilino-4,4'-bipyridin-2-yl)-N'-(4-butyl-2-methylphenyl)urea;
N-(2'-anilino-4,4'-bipyridin-2-yl)-N'-[5-methyl-2-(trifluoromethyl)-3-furyl]urea;
ethyl3-({[(2'-anilino-4,4'-bipyridin-2-yl)amino] carbonyl}amino) benzoate;
N-(2'-anilino-4,4'-bipyridin-2-yl)-N'-(4-butoxyphenyl)urea;
N-(2'-anilino-4,4'-bipyridin-2-yl)-N'-(2,6-diisopropylphenyl)urea;
N-(2'-anilino-4,4'-bipyridin-2-yl)-N'-(4-methylbenzyl)urea;
N-(2'-anilino-4,4'-bipyridin-2-yl)-N'-(5-chloro-2,4-dimethoxyphenyl)urea;
N-(2'-anilino-4,4'-bipyridin-2-yl)-N'-{4-[(trifluoromethyl) thio]phenyl}urea;
N-(2'-anilino-4,4'-bipyridin-2-yl)-N'-[3,5-bis(trifluoromethyl)phenyl]urea;
1-acetyl-N-(2'-anilino-4,4'-bipyridin-2-yl)piperidine-4-carboxamide;
N-(2'-anilino-4,4'-bipyridin-2-yl)-5-oxoprolinamide;
N3-acetyl-N1-(2'-anilino-4,4'-bipyridin-2-yl)-1-alaninamide;
N-(2'-anilino-4,4'-bipyridin-2-yl)piperidine-4-carboxamide;
3-amino-N-(2'-anilino-4,4'-bipyridin-2-yl) butanamide;
N-(T-anilino-4,4'-bipyridin-2-yl)-L-prolinamide;
N-(2'-anilino-4,4'-bipyridin-2-yl)acetamide;
Methyl 2'-anilino-4,4'-bipyridin-2-ylcarbamate;

N-(2'-anilino-4,4'-bipyridin-2-yl)methanesulfonamide;
N-(2'-anilino-4,4'-bipyridin-2-yl)cyclohexanecarboxamide;
1-Acetyl-N-(2'-anilino-4,4'-bipyridin-2-yl)piperidine-2-carboxamide;
1-Acetyl-N-(2'-anilino-4,4'-bipyridin-2-yl)piperidine-3-carboxamide;
Ethyl-4-[(2'-anilino-4,4'-bipyridin-2-yl)amino]-4-oxobutanoate;
N-(2'-anilino-4,4'-bipyridin-2-yl) tetrahydrofuran-2-carboxamide;
(S)-3 N2-acetyl-N1-(2'-anilino-4,4'-bipyridin-2-yl)methioninamide;
N-(2'-anilino-4,4'-bipyridin-2-yl) tetrahydro-2H-pyran-4-carboxamide;
Ethyl 3-[(2'-anilino-4,4'-bipyridin-2-yl)amino]-3-oxopropanoate;
N-(2'-anilino-4,4'-bipyridin-2-yl)-3-(methylthio) propanamide;
N-(2'-anilino-4,4'-bipyridin-2-yl)-2-pyrrolidin-2-ylacetamide;
(3S)-3-amino-N (2'-anilino-4,4'-bipyridin-2-yl)-4-cyanobutanamide;
N1-(2'-anilino-4,4'-bipyridin-2-yl)cyclopropane-1,1-dicarboxamide;
(3S)-1-acetyl-N-(2'-anilino-4,4'-bipyridin-2-yl)piperidine-3-carboxamide;
N-(2'-anilino-4,4'-bipyridin-2-yl) tetrahydrofuran-3-carboxamide (+) and (−);
N{2'-[(4-fluorophenyl)amino]-4,4'-bipyridin-2-yl}tetrahydrofuran-3-carboxamide;
N{2'-[(4-fluorophenyl)amino]-4,4'-bipyridin-2-yl}tetrahydro-2H-pyran-4-carboxamide;
Ethyl-4-({2'-[(4-fluorophenyl)amino]-4,4'-bipyridin-2-yl}amino)-4-oxobutanoate; 4-({2'-[(4-Fluorophenyl)amino]-4,4'-bipyridin-2-yl}amino)-4-oxobutanoic acid;
N-2'-[(4-fluorophenyl)amino]-4,4'-bipyridin-2-yl}-3-(methylthio) propanamide;
(f)-1-Acetyl-N {2'-[(4-fluorophenyl)amino]-4,4'-bipyridin-2-yl}piperidine-3-carboxamide;
(3R)-1-Acetyl-N-{2'-[(4-fluorophenyl)amino]-4,4'-bipyridin-2-yl}piperidine-3-carboxamide;
(3R)-1-acetyl-N-{2'-[(4-fluorophenyl)amino]-4,4'-bipyridin-2-yl}piperidine-3-carboxamide;
1-Acetyl-N {2'-[(4-fluorophenyl)amino]-4,4'-bipyridin-2-yl}pyrrolidine-3-carboxamide;
3-(Aminosulfonyl)-N {2'-[(4-fluorophenyl)amino]-4,4'-bipyridin-2-yl}benzamide;
Ethyl2-{[(2'-anilino-4,4'-bipyridin-2-yl)amino] methyl}cyclopropanecarboxylate;
2-{[(2'-Anilino-4,4'-bipyridin-2-yl)amino] methyl}cyclopropanecarboxylic acid;
N-phenyl-N-(tetrahydro-2H-pyran-4-ylmethyl)-4,4'-bipyridine-2,2'-diamine;
N-phenyl-N-(tetrahydrofuran-3-ylmethyl)-4,4'-bipyridine-2,2'-diamine.

The following derivatives are contemplated for use as therapeutics in treating type I diabetes:

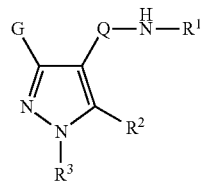

wherein: R' is selected from hydrogen, $CONH_2$, $T_{(n)}$-R, or $T_{(n)}$-$Ar^1$; R is an aliphatic or substituted aliphatic group; n is zero or one; T is $C(=O)$, $CO_2$, CONH, $S(O)_2$, $S(O)_2NH$, $COCH_2$ or $CH_2$; $R_2$ is selected from hydrogen, —R, —$CH_2OR$, —$CH_2OH$, —CH=O, —$CH_2SR$, —$CH_2S(O)_2R$, —$CH_2(C=O)R$, —$CH_2CO_2R$, —$CH_2CO_2H$, —$CH_2CN$, —$CH_2NHR$, —$CH_2N(R)_2$, —CH=N—OR, —CH=NNHR, —CH=NN(R)_2, —CH=NNHCOR, —CH=NNHCO_2R, —CH=NNHSO_2R, -aryl, —$CH_2$(aryl), —$CH_2NH_2$, —$CH_2NHCOR$, —$CH_2NHCONHR$, —$CH_2NHCON(R)_2$, —$CH_2NRCOR$, —$CH_2NHCO_2R$, —$CH_2CONHR$, —$CH_2CON(R)_2$, —$CH_2SO_2NH_2$, —$CH_2$(heterocyclyl), or -(heterocyclyl); $R^3$ is selected from hydrogen, —R, hydroxyalkyl, alkoxyalkyl, alkylthioalkyl, aminoalkyl, alkylaminoalkyl, dialkylaminoalkyl, heterocyclyl, heterocyclylalkyl, aryl, arylalkyl, or aryloxyalkyl; G is hydrogen or $C_{1-3}$ alkyl; Q-NH is

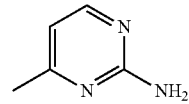

wherein the H of Q-NH is optionally replaced by R, COR, $S(O)_2R$, or $CO_2R$; A is N or CH; $Ar^1$ is aryl, substituted aryl, heterocyclyl or substituted heterocyclyl, wherein $Ar^1$ is optionally fused to a partially unsaturated or fully unsaturated five to seven membered ring containing zero to three heteroatoms; wherein each substitutable carbon atom in $Ar^1$, including the fused ring when present, is optionally and independently substituted by halo, R, OR, SR, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, $S(O)R$, $SO_2NHR$, or $NHS(O)_2R$, and wherein each saturated carbon in the fused ring is further optionally and independently substituted by =O, =S, =NNHR, =$NNR_2$, =$NNHCOR$, =$NNHCO_2R$, =$NNHSO_2R$, or =NR; and wherein each substitutable nitrogen atom in $Ar^1$ is optionally substituted by R, COR, $S(O)_2R$, or $CO_2R$. These compounds have been described in U.S. Patent Application Publication 2002/0111353 and all of which or any present or future corresponding U.S. application or patent are hereby incorporated by reference. Preferred embodiments include:

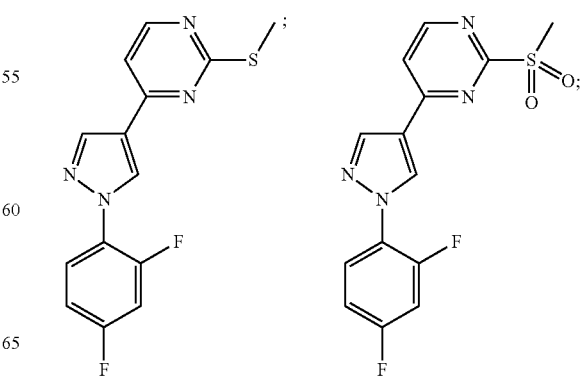

-continued

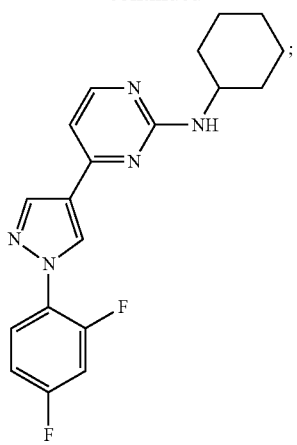

Further illustrative embodiments can be found in the corresponding identified reference.

The following derivatives are contemplated for use as therapeutics in treating type I diabetes:

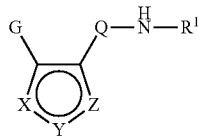

wherein: X—Y—Z is selected from one of the following:

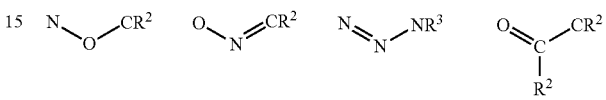

$R^1$ is H, $CONH_2$, $T_{(n)}$-R, or $T_{(n)\text{-}Ar}^2$; R is an aliphatic or substituted aliphatic group; n is zero or one; T is C(=O), $CO_2$, CONH, $S(O)_2$, $S(O)_2NH$, $COCH_2$ or $CH_2$; each $R^2$ is independently selected from hydrogen, —R, —$CH_2OR$, —$CH_2OH$, —CH=O, —$CH_2SR$, —$CH_2S(O)_2R$, —$CH_2$(C=O)R, —$CH_2CH_2CO_2R$, —$CH_2CO_2H$, —$CH_2CN$, —$CH_2NHR$, —$CH_2N(R)_2$, —H=N—OR, —CH=NNHR, —CH=NN(R)_2, —CH=NNHCOR, —CH=NNHCO_2R, —CH=NNHSO_2R, -aryl, -substituted aryl, —$CH_2$(aryl), —$CH_2$(substituted aryl), —$CH_2$ $NH_2$, —$CH_2NHCOR$, —$CH_2NHCONHR$, —$CH_2NHCON(R)_2$, —$CH_2NRCOR$, —$CH_2$ $NHCO_2R$, —$CH_2CONHR$, —$CH_2CON(R)_2$, —$CH_2SO_2NH_2$, —$CH_2$ (heterocyclyl), —$CH_2$ (substituted heterocyclyl), -(heterocyclyl), or -(substituted heterocyclyl); each $R^3$ is independently selected from hydrogen, R, COR, $CO^2R$ or $S(O)^2R$; C is R or $Ar^1$; $Ar^1$ is aryl, substituted aryl, arylalkyl, substituted arylalkyl, heterocyclyl, or substituted heterocyclyl, wherein $Ar^1$ is optionally fused to a partially unsaturated or fully unsaturated five to seven membered ring containing zero to three heteroatoms; Q-NH is

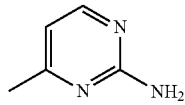

wherein the H of Q-NH is optionally replaced by $R^3$; $Ar^2$ is aryl, substituted aryl, heterocyclyl or substituted heterocyclyl, wherein $Ar^2$ is optionally fused to a partially unsaturated or fully unsaturated five to seven membered ring containing zero to three heteroatoms; wherein each substitutable carbon atom in $Ar^2$, including the fused ring when present, is optionally and independently substituted by halo, R, OR, SR, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, S(O)R, $SONH_2$, S(O)R, $SO_2NHR$, or $NHS(O)_2R$, and wherein each saturated carbon in the fused ring is further optionally and independently substituted by =O, =NNHR, =NNR_2, =NNHCOR, =NNHCO_2R, =NNHSO_2R, or =NR; and wherein each substitutable nitrogen atom in $Ar^2$ is optionally substituted by R, COR, $S(O)_2R$, or $CO_2R$. These compounds have been described in U.S. Pat. No. 6,693,108, and all of which or any present or future corresponding U.S. application or patent are hereby incorporated by reference. Preferred embodiments include:

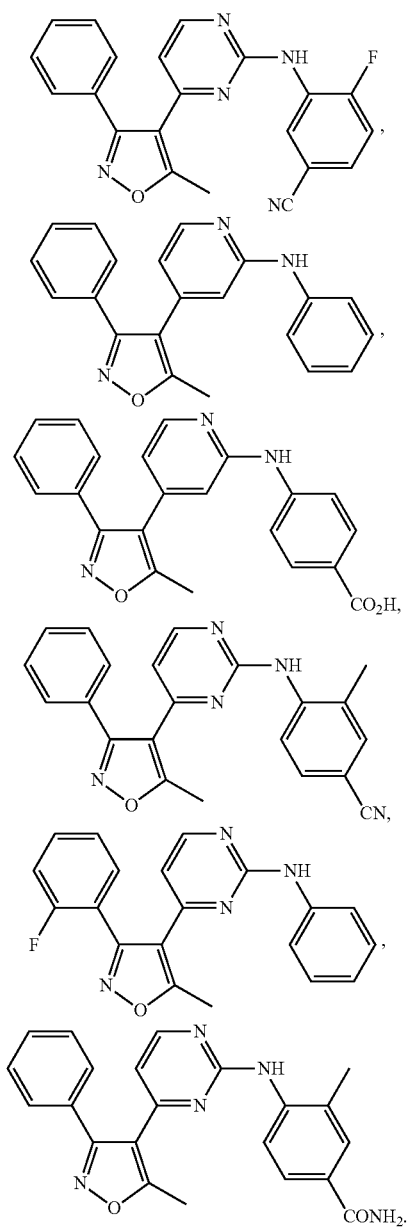

Further illustrative embodiments can be found in the identified reference.

The following derivatives are contemplated for use as therapeutics in treating type I diabetes:

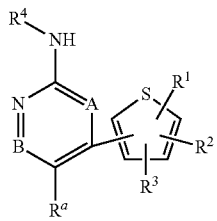

wherein: A and B are each independently selected from N or CH; $R^1$ and $R^2$ are each independently selected from halogen, CN, $NO_2$, $N(R)_2$, OR, SR, or $(T)_n$-$R^5$; $R^3$ is selected from a 3-6 membered carbocyclic or heterocyclic ring having one to two heteroatoms independently selected from nitrogen, oxygen, or sulfur, phenyl, or a 5-6 membered heteroaryl ring having one to three heteroatoms independently selected from nitrogen, oxygen, or sulfur, wherein said phenyl or heteroaryl ring is optionally substituted with one $(T)_n$-Ar and one to two $R^7$; each n is independently selected from zero or one; T is a $C_1$-$C_6$ alkylidene chain, wherein one methylene unit of T is optionally replaced by CO, $CO_2$, COCO, CONR, OCONR, NRNR, NRNRCO, NRCO, $NRCO_2$, NRCONR, $SO_2$, $NRSO_2$, $SO_2NR$, $NRSO_2NR$, O, S, or NR; each R is independently selected from hydrogen or an optionally substituted $C_1$-$C_6$ aliphatic group; or two R on the same nitrogen atom may be taken together with the nitrogen to form a four to eight membered, saturated or unsaturated heterocyclic ring containing one to three heteroatoms independently selected from nitrogen, oxygen, or sulfur; $R^4$ is $(T)_n$-R, $(T)_n$-Ar, or $(T)_n$-$Ar^1$; $R^a$ is selected from $R^b$, halogen, $NO_2$, $OR^b$, $SR^b$, or $N(R^b)_2$; $R^b$ is selected from hydrogen or a $C_1$-$C_4$ aliphatic group optionally substituted with oxo, OH, SH, $NH_2$, halogen, $NO_2$, or CN; $R^5$ is an optionally substituted $C_1$-$C_6$ aliphatic or Ar; Ar is a 5-6 membered saturated, partially unsaturated, or aryl monocyclic ring having zero to three heteroatoms independently selected from nitrogen, sulfur, or oxygen, or an 8-10-membered saturated, partially unsaturated, or aryl bicyclic ring having zero to four heteroatoms independently selected from nitrogen, sulfur, or oxygen, wherein Ar is optionally substituted with one to three $R^7$; $Ar^1$ is a 6-membered aryl ring having zero to two nitrogens, wherein said ring is substituted with one Z—$R^6$ group and optionally substituted with one to three $R^7$; Z is a $C_1$-$C_6$ alkylidene chain wherein up to two non-adjacent methylene units of Z are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; provided that said optionally replaced methylene unit of Z is a methylene unit non-adjacent to $R^6$; $R^6$ is selected from Ar, R, halogen, $NO_2$, CN, OR, SR, $N(R)_2$, NRC(O)R, NRC(O)$N(R)_2$, $NRCO_2R$, C(O)R, $CO_2R$, OC(O)R, C(O)$N(R)_2$, OC(O)$N(R)_2$, SOR, $SO_2R$, $SO_2N(R)_2$, $NRSO_2R$, $NRSO_2N(R)_2$, C(O)C(O)R, or C(O)$CH_2$C(O)R; and each $R^7$ is independently selected from R, halogen, $NO_2$, CN, OR, SR, $N(R)_2$, NRC(O)R, NRC(O)$N(R)_2$, $NRCO_2R$, C(O)R, $CO_2R$, C(O)$N(R)_2$, OC(O)$N(R)_2$, SOR, $SO_2R$, $SO_2N(R)_2$, $NRSO_2R$, $NRSO_2N(R)_2$, C(O)C(O)R, or C(O)$CH_2$C(O)R; or two $R^7$ on adjacent positions of $Ar^1$ may be taken together to form a saturated, partially unsaturated, or fully unsaturated five to seven membered ring containing zero to three heteroatoms selected from O, S, or N. These compounds have been described in U.S. Patent Application Publication Number 2004/0023963 and all of which or any present or future corresponding U.S. application or patent are hereby incorporated by reference. Preferred embodiments include:

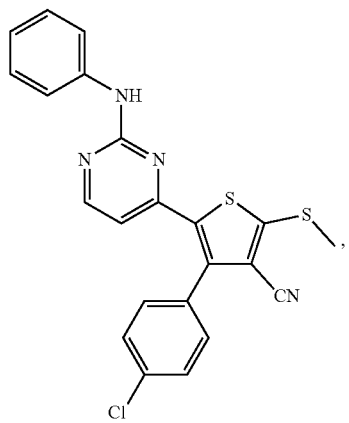

-continued

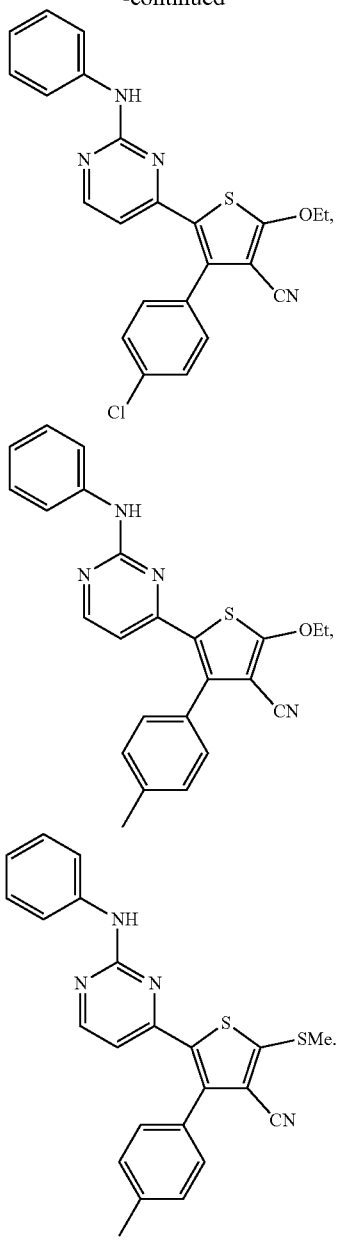

Further illustrative embodiments can be found in the identified reference.

The following derivatives are contemplated for use as therapeutics in treating type I diabetes:

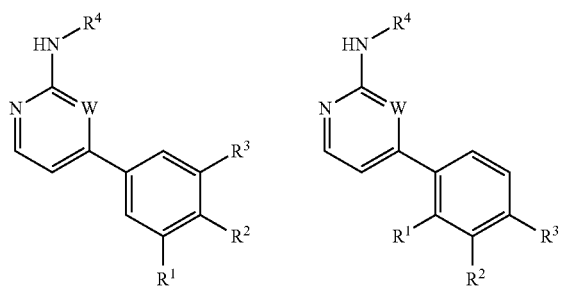

wherein: each W is independently selected from nitrogen or CH; each $R^1$, $R^2$, and $R^3$ is independently selected from halogen, QR, $Q_{(n)}$CN, $Q_{(n)}$NO$_2$, or $Q_{(n)}$Ar; wherein: $R^1$ and $R^2$ or $R^2$ and $R^3$ are optionally taken together to form a 4-8 membered saturated, partially unsaturated, or fully unsaturated ring having 0-3 heteroatoms independently selected from nitrogen, oxygen, or sulfur; n is zero or one; Q is a $C_{1-4}$ alkylidene chain wherein one methylene unit of Q is optionally replaced by O, S, NR, NRCO, NRCONR, NRCO$_2$, CO, CO$_2$, CONR, OC(O)NR, SO$_2$, SO$_2$NR, NRSO$_2$, NRSO$_2$NR, C(O)C(O), or C(O)CH$_2$C(O); each R is independently selected from hydrogen or an optionally substituted $C_1$-$C_4$ aliphatic, wherein: two R bound to the same nitrogen atom are optionally taken together with the nitrogen atom to form a 3-7 membered saturated, partially unsaturated, or fully unsaturated ring having 1-2 additional heteroatoms independently selected from nitrogen, oxygen, or sulfur; $R^4$ is $Ar^1$, T-$Ar^2$, or $T_{(n)}$-$Ar^3$; T is a $C_{1-2}$ alkylidene chain wherein one methylene unit of T is optionally replaced by O, NR, NRCO, NRCONR, NRCO$_2$, CO, CO2, CONR, OC(O)NR, SO$_2$, SO$_2$NR, NRSO$_2$, NRSO$_2$NR, C(O)C(O), or C(O)CH$_2$C(O); $Ar^1$ is a 5-6 membered monocyclic or 8-10 membered bicyclic saturated, partially unsaturated, or fully unsaturated ring system; wherein: Arl is optionally substituted with up to five substituents, wherein the first substituent is selected from $R^x$ or $R^5$ and wherein any additional substituents are independently selected from $R^5$; each $R^x$ is independently selected from a 5-6 membered aryl ring having 0-3 heteroatoms selected from nitrogen, oxygen, or sulfur, wherein: $R^x$ is optionally substituted with 1-3 $R^5$; each $R^5$ is independently selected from R, halogen, NO$_2$, CN, OR, SR, N(R)$_2$, NRC(O)R, NRC(O)N(R)$_2$, NRCO$_2$R, C(O)R, CO$_2$R, C(O)N(R)$_2$, OC(O)N(R)$_2$, SOR, SO$_2$R, SO$_2$N(R)$_2$, NRSO$_2$R, NRSO2N(R)$_2$, C(O)C(O)R, or C(O)CH$_2$C(O)R; $Ar^2$ is a 5-6 membered saturated, partially unsaturated, or fully unsaturated monocyclic ring having 0-3 heteroatoms independently selected from nitrogen, oxygen, or sulfur, or an 8-10 membered saturated, partially unsaturated, or fully unsaturated bicyclic ring system having 0-5 heteroatoms independently selected from nitrogen, oxygen, or sulfur; wherein: Ar2 is optionally substituted with up to five substituents, wherein the first substituent is selected from $R^x$ or $R^5$ and wherein any additional substituents are independently selected from $R^5$; $Ar^3$ is a 6-membered aryl ring having 0-2 nitrogens, wherein: $Ar^3$ is substituted with one Z—R group and optionally substituted with 1-3 $R^5$; Z is a $C_1$-$C_6$ alkylidene chain wherein up to two non adjacent methylene units of Z are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and $R^6$ is selected from $Ar^2$, R, halogen, NO$_2$, CN, OR, SR, N(R)$_2$, NRC(O)R, NRC(O)N(R)$_2$, NRCO$_2$R, C(O)R, CO$_2$R, OC(O)R, C(O)N(R)$_2$, OC(O)N(R)$_2$, SOR, SO$_2$R, SO$_2$N(R)$_2$, NRSO$_2$R, NRSO$_2$N(R)$_2$, C(O)C(O)R, or C(O)CH$_2$C(O)R. These compounds have been described in International Publication Number WO 2002/079197 and all of which or any present or future corresponding U.S. application or patent are hereby incorporated by reference. Preferred embodiments include:

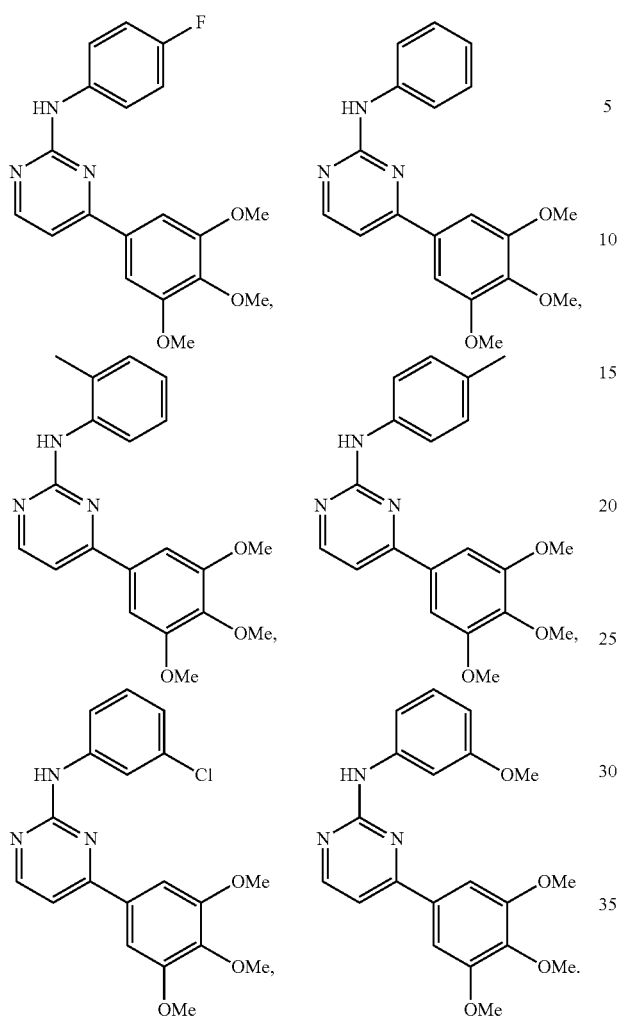

Further illustrative embodiments can be found in the identified reference.

The following derivatives are contemplated for use as therapeutics in treating type I diabetes:

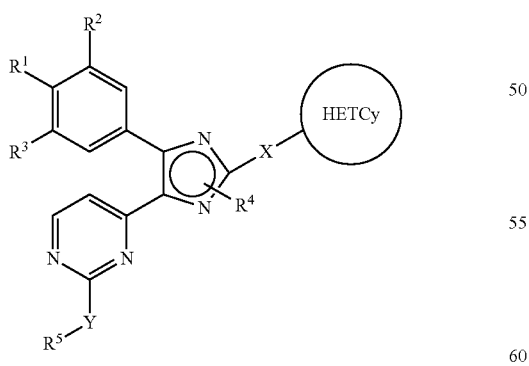

wherein $R^1$ is —F, —Cl, —Br, —OH, —SH, —NH$_2$, or —CH$_3$; $R^2$ is —F, —Cl, —Br —OH, —SH, —NH$_2$, or —CH$_3$; $R^3$ is —H, —F, —Cl, —Br, —OH, —SH, —NH$_2$, —CH$_3$, —OCH$_3$, or —CH$_2$CH$_3$; $R^4$ is —C$_{1-4}$ alkyl optionally substituted with a —C$_{3-7}$ cycloalkyl; $R^5$ is —C$_{1-4}$ alkyl or —C$_{3-7}$ cycloalkyl, wherein the —C$_{1-4}$ alkyl is optionally substituted with a phenyl; X is a bond or an alkyl bridge having 1-3 carbons; Y is —NH— or —NH$_2$+—; and HETCy is a 4 to 10 membered non-aromatic heterocycle containing at least one N atom, optionally containing 1-2 additional N atoms and 0-10 or S atom, and optionally substituted with —C$_{1-4}$ alkyl or —C(O)—O—CH$_2$phenyl. These compounds have been described in International Publication Number WO 2001/091749 and all of which or any present or future corresponding U.S. application or patent are hereby incorporated by reference. Preferred embodiments include:

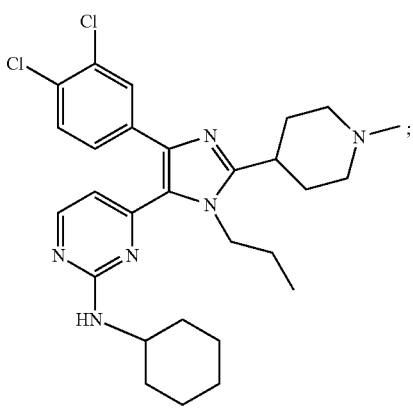

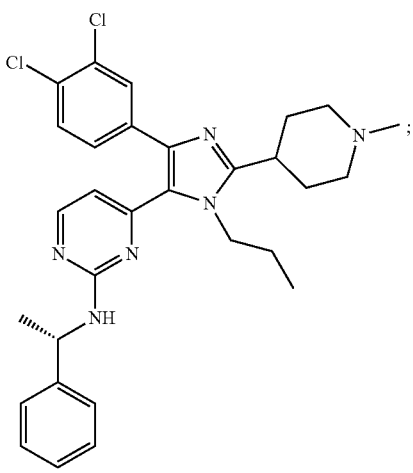

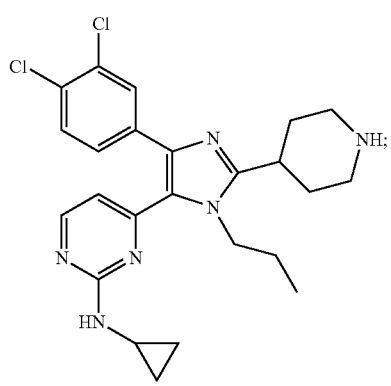

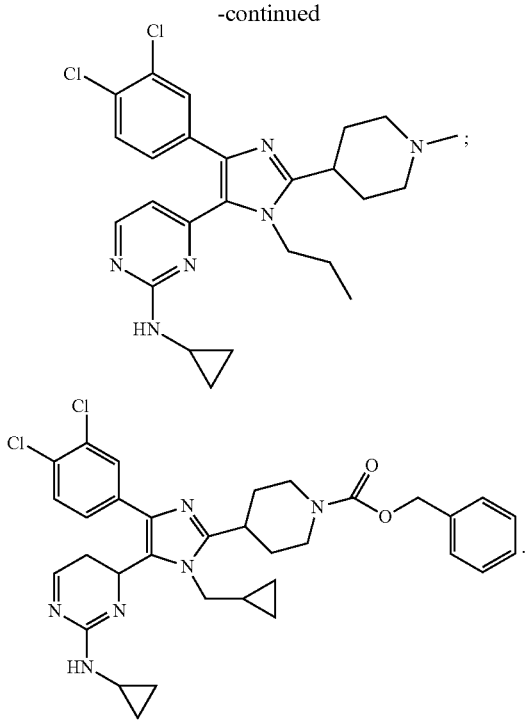

Further illustrative embodiments can be found in the corresponding identified reference.

The embodiments of the current invention are not limited to compounds with the structures provide. JNK2 inhibitors and selective JNK2 inhibitors can be made using organic synthesis techniques known to those skilled in the art, as well as by the methods described in the respective identified references.

JNK2 Assays

Proteins can be purified by expressing the amino acid sequence (i.e., JNK2) in a host, such as *E. coli*. The protein may be expressed in combination with a second amino acid sequence (fusion-proteins) that has properties preferential for purification. For example, The Glutathione S-transferase (GST) gene fusion system is an integrated system for the expression, purification and detection of fusion proteins produced in bacterial, yeast, mammalian and insect cells.

The sequence encoding the GST protein is incorporated into an expression vector, generally upstream of the multi-cloning site. The sequence encoding the protein of interest is then cloned into this vector. Induction of the vector results in expression of a fusion protein—the protein of interest fused to the GST protein. The fusion protein can then be released from the cells and purified.

Purification of the fusion protein is facilitated by the affinity of the GST protein for glutathione residues. Glutathione residues are coupled to a resin and the expressed protein product is brought into contact with the resin. The fusion protein will bind to the glutathione-resin complex and all other non-specific proteins can be washed off. The fusion protein can then be released from the resin using a mild elution buffer that is of low pH. Similarly, poly-histidine sequences (his-tags) can be used.

It is possible to remove the GST or his-tag from the protein of interest by using a number of different enzymes (thrombin, factor X), which cleave specific sites between the GST or his-tag and the protein of interest. Fusion proteins can also be detected easily, with a number of antibodies now available on the market.

There are many well-known methods to one skilled in the art for determining the binding of one protein to another. One or more of the following methods and other methods well-known to those skilled in the art can be used to determine whether a compound is an inhibitor JNK2 or selective inhibitor of JNK2.

For example, to 10 μL of 5-amino-anthra(9,1-cd)isothiazol-6-one in 20% DMSO/80% dilution buffer containing of 20 mM HEPES (pH 7.6), 0.1 mM EDTA, 2.5 mM magnesium chloride, 0.004% Triton×100, 2 μg/mL leupeptin, 20 mM β-glycerolphosphate, 0.1 mM sodium vanadate, and 2 mM DTT in water is added 30 μL of 50-200 ng His6-JNK2 in the same dilution buffer. The mixture is pre-incubated for 30 minutes at room temperature. Sixty μL of 10 μg GST-c-Jun (1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton×100, 11 μM ATP, and 0.5 μCi γ-32P ATP in water is added and the reaction is allowed to proceed for 1 hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of 5-amino-anthra(9,1-cd)isothiazol-6-one at which the c-Jun phosphorylation is reduced to 50% of the control value. Compounds that inhibit JNK2 preferably have an $IC_{50}$ value ranging 0.01-10 μM in this assay. 5-Amino-anthra(9,1-cd)isothiazol-6-one has an $IC_{50}$ according to this assay of 1 μM for JNK2 and 400 nM for JNK3. The measured $IC_{50}$ value for 5-amino-anthra (9,1-cd)isothiazol-6-one, as measured by the above assay, however, shows some variability due to the limited solubility of 5-amino-anthra(9,1-cd)isothiazol-6-one in aqueous media. Despite the variability, however, the assay consistently does show that 5-amino-anthra(9,1-cd)isothiazol-6-one selectively inhibits JNK2. This assay demonstrates that 5-amino-anthra(9,1-cd)isothiazol-6-one, an illustrative JNK2 inhibitor, inhibits JNK2 selectively and, accordingly, is useful for treating or preventing type I diabetes.

In other examples, following pretreatment with JNK2 inhibitor (63-1700 nM in Buffer B (20 mM HEPES, 20 mM $MgCl_2$, 20 mM β-glycerophosphate, pH 7.6, containing 500 μm dithiothreitol, 100 μm sodium orthovanadate), JNK activity is assayed by incubation in Buffer B supplemented with 20 μm ATP, 1 μCi of [γ-$^{32}$P]ATP, and a protein substrate (10 μg of either GST-c-Jun, GST-Elk, or GST-ATF2). The reaction is performed for 30 min at 30° C., and then the phosphorylated substrate was separated by SDS-PAGE, visualized by autoradiography, and quantitated by Cerenkov counting.

C-Jun Reporter Assays

Detection of JNK2 inhibition is also described in United States Patent Application Publication US 2004/0248886 A1, hereby incorporated by reference. The phosphorylation of c-jun by JNK2 is followed by monitoring the incorporation of $^{33}$P into c-jun following the protocol below. The inhibitory activity of the JNK2 inhibitors, towards c-jun phosphorylation through JNK2, is determined by calculating phosphorylation activity in the presence or absence of JNK2 inhibitor.

JNK2 assays can be performed in 96 well MTT plates: incubation of 0.5 μm of recombinant, pre-activated GST-JNK2 with 1 μg of recombinant, biotinylated GST-c-Jun and 2 μM $^{33}$γ-ATP (2 nCi/μL), in the presence or absence of JNK2 inhibitor and in a reaction volume of 50 μL, containing 50 mM Tris-HCl, pH 8.0; 10 mM $MgCl_2$; 1 mM Dithiothreitol, and 100 μm $Na_3VO_4$. The incubation is performed for 120 min. at R. T and stopped upon addition of 200 μL of a solution containing 250 µg of Streptavidine-coated SPA beads (Amershain, Inc.), 5 mM EDTA, 0.1% TritonX-100 and 50 µm ATP, in phosphate saline buffer.

After incubation for 60 minutes at RT, beads are sedimented by centrifugation, resuspended in 200 µL of PBS containing 5 mM EDTA, 0.1% Triton X-100 and 50 µM ATP and the radioactivity measured in a scintillation beta counter, following sedimentation of the beads as described above. By replacing biotinylated GST-c Jun with biotinylated GST-$_1$ATF$_2$ or biotinylated myelin basic protein, this assay can be used to measure inhibition of preactivated p38 and ERK MAP Kinases, respectively. The JNK2 inhibitors display an inhibition (IC$_{50}$) with regard to JNK2 of less than 10 µM, preferably less than 1 µM and more preferred less than 0.25 µM.

The phosphorylation of the transcriptional factor, c-jun, by JNK2 in the MAP kinase signal transduction pathway can be followed via a trans-reporting system such as the commercially available PathDetect as provided in Xu, L. et al., Assess the in-vivo activation of signal transduction pathways with Pathdetect reporting systems, Strategies 2001, 14 (1): 17-19.

A trans-reporting system allows one to follow, via Luciferase activity, the activation status of a fusion trans-activator protein. The trans-activator protein consists of the activation domain of the transcriptional factor of interest (c-jun) fused with a yeast transcriptional activator, GAL4 DNA binding domain (dbd). The GAL4 dbd has the advantage that no known mammalian transcriptional factors bind to it and therefore the background noise of the assay is very low.

In the present case, Hela luciferase reporter-c-Jun (HLR-c-Jun) cell lines that constitutively express GAL4-cJun may be used. Recombinant JNK2 and substrates (c-Jun-(1-135), Elk-(307-428), or ATF2-(19-96)) may be produced in *Escherichia coli* as GST fusion proteins. For JNK2, the GST portion of the fusion protein may be removed by overnight cleavage with thrombin (3 units) in Thrombin Cleavage buffer (50 mM Tris, pH 8.0, 150 mM NaCl, 5 mM MgCl$_2$, 2.5 mM CaCl$_2$, and 1 mM dithiothreitol)

Once, JNK is activated it can induce the phosphorylation of the c-jun domain of the fusion trans-activator protein (GAL4 dbd-cjun) which forms a dimer. The dimer is then is able to bind to a GAL4 upstream activating sequence (GAL4 UAS) of the reporter that activates Luciferase expression. Luciferase expression is detected by luminescence using a simple assay such as Dual-Luciferase Reporter Assay System in which *Renilla* is used as a "control reporter". Inhibition of JNK is observed as a decrease in Luciferase expression and detected by a decrease in luminescence. U.S. Patent Number U.S. Pat. No. 5,744,320, hereby incorporated by reference, describes a Dual-Luciferase Reporter Assay System.

LPS Induced Endotoxin Shock in Mice

Endotoxins are the lipopolysaccharides (LPS) constituents of the outer membrane of Gram-negative bacteria. Response to LPS has been shown to involve the activation of different cell populations and to lead to the expression of various inflammatory cytokines that include tumor necrosis factor-alpha (TNF-α) and interferon γ (IFN-γ). As LPS is known to stimulate the activation of various MAP kinase pathways, including MK, the ability of JNK inhibitors can be tested after the JNK signaling pathway has been switched on by a LPS challenge.

The activity as JNK inhibitors of compounds of formula may be assessed after a LPS challenge using the following protocol: LPS(*S. abortus*-Galanos Lab-) is injected (200 µg/kg, i.v.) to Male C57BL/6 mice to induce endotoxin shock. Compounds (0.1, 1, 10 mg/kg) or NaCl (200 µM) are injected intravenously (10 mL/kg) 15 min before the LPS challenge. Heparinized blood was obtained from the orbital sinus at different time points after the LPS challenge, and the blood was centrifuged at 9'000 rpm for 10 mM at 4° C. to collect supernatant. Measurement of cytokines production such as TNF-α and IFN-γ by mouse is performed with an ELISA kit such as Duoset DY410 for TNF-α and DY 485 for IFN-γ. Other ELISA assays can be used.

Surface Plasmon Resonance

Real time kinetic studies of the interactions between recombinant JNK proteins (JNK2, JNK3, and kinase-inactive JNK3) and peptide may be performed on a BIAcore 2000 biosensor. The running and sample dilution buffer is 10 mM HEPES, pH 7.4, 150 mM NaCl, 3.4 mM EDTA, 0.005% (v/v) Tween 20. The biotinylated peptide may immobilized onto 3 flow cells of each 4-flow cell SA-biosensor chip to achieve ~20, 40, and 80 resonance units (RU). The remaining blank flow cell on each chip measured background interactions.

The binding of proteins to the immobilized peptides is recorded as RU in real time to provide a sensorgram. Binding profiles are created by injecting 10 µM JNK2, JNK3, and kinase-inactive JNK3 (JNK3 (kin⁻)) at a flow rate of 20 µl/min. GST-c-Jun-(1-135), GST-Elk-(307-428), and GST-ATF2-(19-96) are injected at 5 µm concentration to approximate concentrations present during standard in vitro kinase assays.

Pharmaceutical Compositions

The compositions comprising a JNK2 inhibitor include bulk-drug compositions useful in the manufacture of pharmaceutical compositions (e.g., impure or non-sterile compositions) and pharmaceutical compositions (i.e., compositions that are suitable for administration to a patient) that can be used in the preparation of unit dosage forms. Such compositions optionally comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of JNK2 inhibitor and another therapeutic or prophylactic agent, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a JNK2 inhibitor is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a patient, the pharmaceutically acceptable vehicles are preferably sterile. Water can be the vehicle when the JNK2 inhibitor is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155).

In a preferred embodiment, the JNK2 inhibitor and optionally a therapeutic or prophylactic agent are formulated in accordance with routine procedures as pharmaceutical compositions adapted for intravenous administration to human beings. Typically, JNK2 inhibitors for intravenous administration are solutions in sterile isotonic aqueous buffer. Where necessary, the compositions can also include a solubilizing agent. Compositions for intravenous administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the JNK2 inhibitor is to be administered by infusion, it can be dispensed, for example, with an infusion bottle containing sterile pharmaceutical grade water or saline. Where the JNK2 inhibitor is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an orally administered JNK2 inhibitor. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the JNK2 inhibitor can be delayed or prolonged by proper formulation. For example, a slowly soluble pellet of the JNK2 inhibitor can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound in oily or emulsified vehicles which allow it to disperse only slowly in the serum.

Formulations

Pharmaceutical compositions for use in accordance with the present invention can be formulated in conventional manner using one or more physiologically acceptable carriers or excipients.

Thus, the JNK2 inhibitor and optionally the therapeutic or prophylactic agent and their physiologically acceptable salts and solvates can be formulated into pharmaceutical compositions for administration by inhalation or insufflation (either through the mouth or the nose) or oral, parenteral or mucosol (such as buccal, vaginal, rectal, sublingual) administration. In one embodiment, local or systemic parenteral administration is used.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the pharmaceutical compositions can take the form of tablets or lozenges formulated in conventional manner.

For administration by inhalation, the pharmaceutical compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The pharmaceutical compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The pharmaceutical compositions can also be formulated in rectal compositions such as suppositories or retention enemas, e.g., containing conventional suppository bases such as cocoa butter or other glycerides.

In addition to the formulations described previously, the pharmaceutical compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The invention also provides that a pharmaceutical composition is packaged in a hermetically sealed container such as an ampoule or sachette indicating the quantity. In one embodiment, the pharmaceutical composition is supplied as a dry sterilized lyophilized powder or water free concentrate in a hermetically sealed container and can be reconstituted, e.g., with water or saline to the appropriate concentration for administration to a patient.

In other embodiments of the invention, radiation therapy agents such as radioactive isotopes can be given orally as liquids in capsules or as a drink. Radioactive isotopes can also be formulated for intravenous injection. The skilled oncologist can determine the preferred formulation and route of administration.

The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($56^{th}$ ed. 2002, herein incorporated by reference in its entirety).

Routes of Administration

Methods of administering a JNK2 inhibitor and optionally a therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the JNK2 inhibitor and optionally the prophylactic or therapeutic agents are administered intramuscularly, intravenously, or subcutaneously. The JNK2 inhibitor and optionally the prophylactic or therapeutic agent can also be administered by infusion or bolus injection and can be administered together with other biologically active agents. Administration can be local or systemic. The JNK2 inhibitor and optionally the prophylactic or therapeutic agent and their physiologically acceptable salts and solvates can also be administered by inhalation or insufflation (either through the mouth or the nose). In a preferred embodiment, local or systemic parenteral administration is used.

In specific embodiments, it can be desirable to administer the JNK2 inhibitor locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the JNK2 inhibitor can be formulated as a suppository, with traditional binders and vehicles such as triglycerides.

In another embodiment, the JNK2 inhibitor can be delivered in a vesicle, in particular a liposome.

In yet another embodiment, the JNK2 inhibitor can be delivered in a controlled release system. In one embodiment, a pump can be used. In another embodiment, polymeric materials can be used.

Dosages

The amount of the JNK2 inhibitor that is effective in the treatment or prevention of type I diabetes can be determined by standard research techniques. For example, the dosage of the JNK2 inhibitor which will be effective in the treatment or prevention of type I diabetes can be determined by administering the JNK2 inhibitor to an animal in a model such as, e.g., the animal models known to those skilled in the art. In addition, in vitro assays can optionally be employed to help identify optimal dosage ranges.

Selection of a particular effective dose can be determined (e.g., via clinical trials) by a skilled artisan based upon the consideration of several factors which will be known to one skilled in the art. Such factors include the disease to be treated or prevented, the symptoms involved, the patient's body mass, the patient's immune status and other factors known by the skilled artisan.

The precise dose to be employed in the formulation will also depend on the route of administration, and the seriousness of the disease-related wasting, and should be decided according to the judgment of the practitioner and each patient's circumstances. Effective doses can be extrapolated from dose-response curves derived from in vitro or animal model test systems.

The dose of a JNK2 inhibitor to be administered to a patient, such as a human, is rather widely variable and can be subject to independent judgment. It is often practical to administer the daily dose of a JNK2 inhibitor at various hours of the day. However, in any given case, the amount of a JNK2 inhibitor administered will depend on such factors as the solubility of the active component, the formulation used, patient condition (such as weight), and/or the route of administration.

The general range of effective amounts of the JNK2 inhibitor alone or in combination with the prophylactic or therapeutic agent(s) are from about 0.001 mg/day to about 1000 mg/day, more preferably from about 0.001 mg/day to 750 mg/day, more preferably from about 0.001 mg/day to 500 mg/day, more preferably from about 0.001 mg/day to 250 mg/day, more preferably from about 0.001 mg/day to 100 mg/day, more preferably from about 0.001 mg/day to 75 mg/day, more preferably from about 0.001 mg/day to 50 mg/day, more preferably from about 0.001 mg/day to 25 mg/day, more preferably from about 0.001 mg/day to 10 mg/day, more preferably from about 0.001 mg/day to 1 mg/day. Of course, it is often practical to administer the daily dose of compound in portions, at various hours of the day. However, in any given case, the amount of compound administered will depend on such factors as the solubility of the active component, the formulation used, subject condition (such as weight), and/or the route of administration.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human and humanized antibodies have a longer half-life within the human body than antibodies from other species due to the immune response to the foreign polypeptides. Thus, lower dosages of human antibodies and less frequent administration is often possible.

The invention provides for any method of administrating lower doses of known agents (e.g., insulin) than previously thought to be useful for the prevention or treatment of type I diabetes.

Kits

The invention provides a pharmaceutical pack or kit comprising one or more containers containing a JNK2 inhibitor and optionally one or more other prophylactic or therapeutic agents useful for the treatment of type I diabetes (e. g insulin). The invention also provides a pharmaceutical pack or kit comprising one or more containers containing one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration; or instructions for the composition's use.

The present invention provides kits that can be used in the above methods. In one embodiment, a kit comprises a INK Inhibitor, in one or more containers, and optionally one or more other prophylactic or therapeutic agents useful for the treatment of type I diabetes, in one or more containers.

Example 1

Spontaneous diabetes is decreased in JNK2-deficient mice. We used the non-obese diabetic (NOD) mouse model of autoimmune diabetes as disclosed in Delovitch & Singh, The non-obese diabetic mouse as a model of autoimmune diabetes: immune dysregulation gets the NOD. Immunity 7, 727-38 (1997). NOD and NOD/Scid mice were obtained from The Jackson Laboratory (Bar Harbor, Me.). Mapk9−/− mice (Yang, D. D. et al. Differentiation of CD4+ T cells to Th1 cells requires MAP kinase JNK2. *Immunity* 9, 575-85 (1998)) were back-crossed with NOD mice for 6 generations and Jnk2−/+ mice that are homozygous for the 15 Idd NOD alleles were identified by PCR genotyping, as described previously (Mora et al., Role of L-selectin in the development of autoimmune diabetes in non-obese diabetic mice. Int Immunol 16, 257-64 (2004)). These NOD/Mapk9−/+mice were back-crossed for an additional four generations onto the NOD background. NOD/Mapk9−/− mice were obtained by crossing NOD/Mapk9−/+ mice. The Mapk9 genotype was examined by PCR analysis. Blood glucose levels were monitored weekly with a Dex-Glucometer (Bayer). Animals with a blood glucose level higher than 200 mg/dl for 2 consecutive weeks were considered diabetic.

The presence of hyperglycemia (blood glucose >200 mg/dl) was examined in a cohort of 32 NOD mice and 28 female NOD/Mapk9−/− mice. The data in FIG. 1 is presented as the % of mice with hyperglycemia. Comparison of the spontaneous incidence of disease in female NOD and NOD/Mapk9−/− mice indicated that JNK2-deficiency decreases the cumulative incidence of diabetes.

Example 2

Figure 2A:
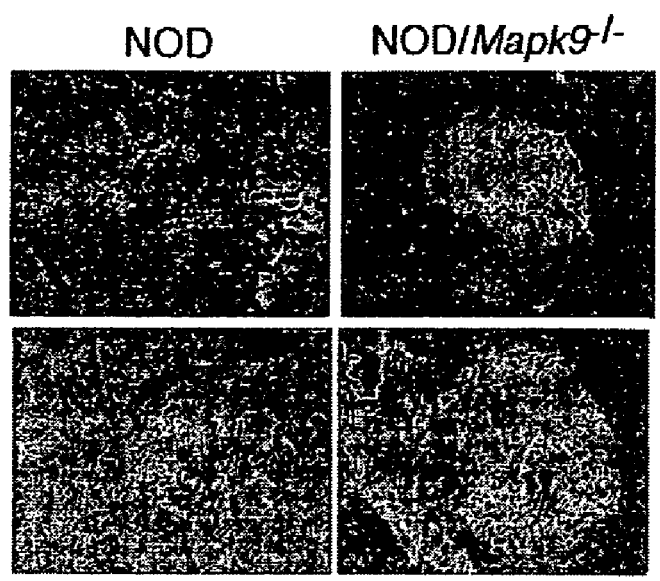
FIG. 2A. JNK2-defiency causes reduced insulitis in NOD mice. Representative islets from 13-week-old mice stained with hematoxylin and eosin are shown.

JNK2-defiency causes reduced insulitis in NOD mice. We performed histological analysis of the pancreas. At 13 weeks of age, control NOD mice exhibited severe islet infiltration with less than 20% normal islets and greater than 50% of the islets showing invasive and destructive insulitis. In contrast, more than 70% of the islets in JNK2-deficient mice were not infiltrated and the residual 30% showed mostly peri-insulitis (FIG. 2a,b). At 30 weeks of age, all the islets of NOD mice showed severe destructive insulitis, but normal un-infiltrated islets were detected in JNK2-deficient NOD mice. Control studies demonstrated that the extent of islet infiltration in JNK1-deficient (Mapk8−/−) NOD mice was similar to wild type NOD mice, indicating a selective role for JNK2 in the regulation of islet infiltration in NOD mice.

Example 3

Figure 3A:
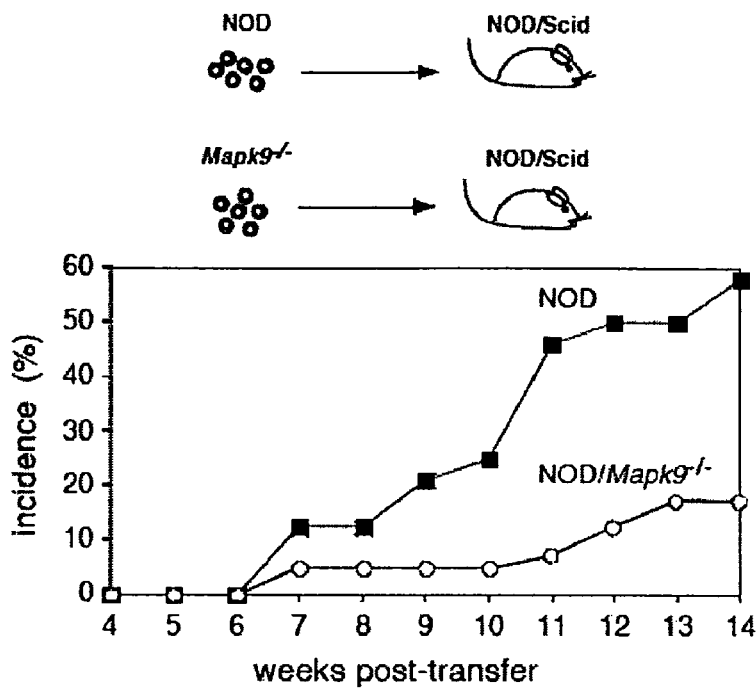
FIG. 3A. JNK2-deficiency causes reduced diabetes in adoptive transfer studies. Splenocytes isolated from pre-diabetic 13 week old NOD or NOD/Mapk9−/− mice were adoptively transferred to immune-deficient NOD/Scid mice. The incidence of diabetes was monitored post-transplantation.

JNK2-deficiency causes reduced diabetes in adoptive transfer studies. Autoimmune diabetes can be adoptively transferred to euglycemic recipients by injection of splenic T cells. In order to examine the diabetogenic potential of T cells from JNK2-deficient mice, T cells from young (13 week old) non-diabetic NOD and NOD/Mapk9−/− mice were transferred into NOD/Scid recipients. NOD/Scid mice were injected intravenously with $2 \times 10^7$ total splenocytes and were monitored (14 weeks) for diabetes. NOD mice (7 weeks old males) were irradiated (725 rad) one day prior to adoptive transfer of $2 \times 10^7$ total splenocytes from recently diagnosed diabetic donors by intravenous injection; the mice were monitored (8 weeks) for diabetes. The incidence of diabetes was significantly reduced if recipient mice received splenic T cells from JNK2-deficient donors compared to control NOD donors (FIG. 3a). This observation indicates that the generation of beta-cell specific diabetogenic T cells may be impaired in JNK2-deficient mice.

Example 4

Analysis of the distribution of T cell populations and their activation markers in lymph nodes and spleen showed no difference between non-diabetic NOD and NOD/Mapk9−/− mice. The presence of T cells in infiltrated islets was examined by immunohistochemistry on frozen pancreatic sections. Pancreata were fixed in 10% formalin, embedded in paraffin, sectioned and stained with hematoxylin-eosin. Immunohistochemistry was performed using tissue embedded in Tissue-Tek OCT and frozen in 2-methylbutane. 5 µm sections were stained with FITC-conjugated antibodies to CD4 and CD8 (PharMingen) and mounted in Vectashield with DAPI (Vector Laboratories).

Figure 2B:
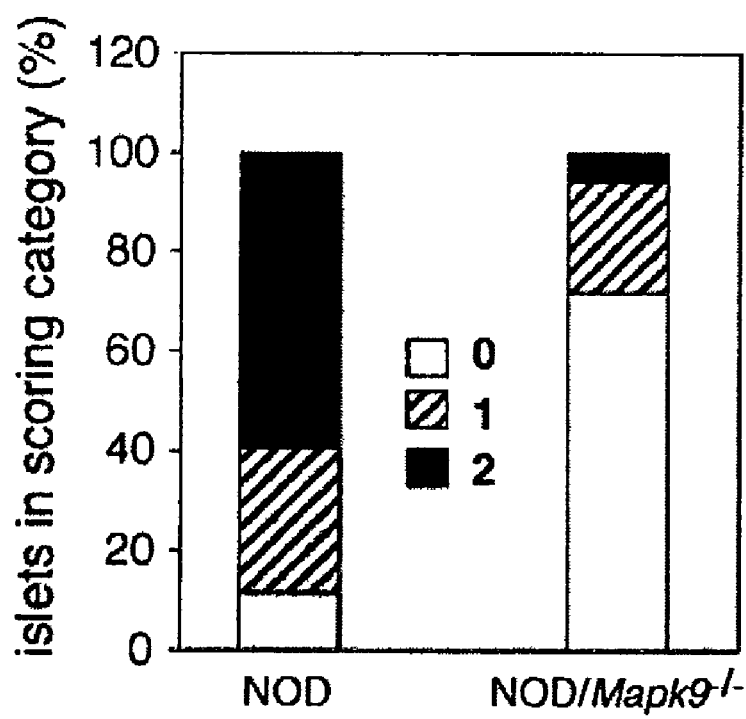
FIG. 2B. The extent of insulitis was quantitated (6 mice per genotype; 10 to 20 islets per mouse). The percentage of islets with normal morphology and with inflammatory infiltration that was restricted to the periphery of the islet (peri-insulitis) or throughout the islet (insulitis) is shown. 0=normal islet, 1=peri-insulitis, 2=insulitis.
Figure 4A:
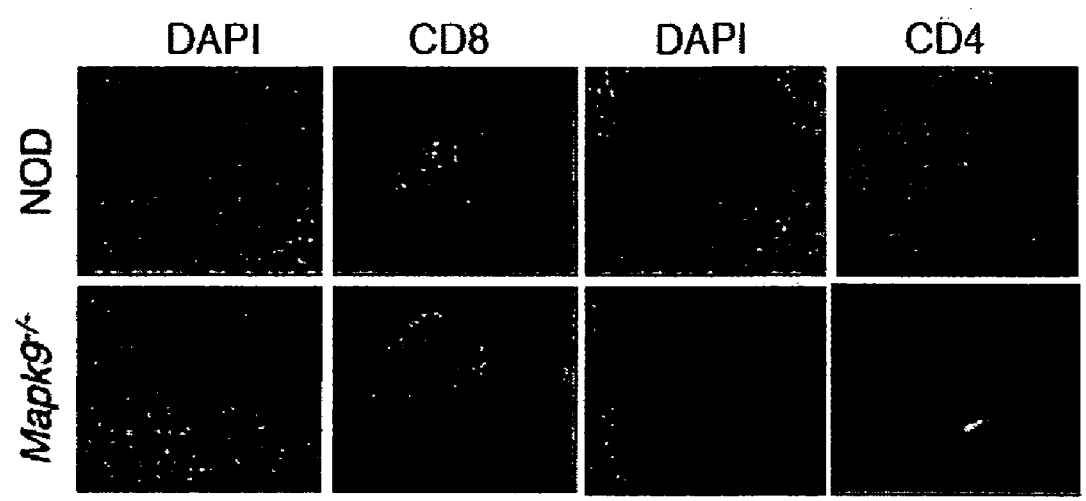
FIG. 4A. T cell defects in JNK2-deficient NOD mice. Pancreatic sections of NOD and NOD/Mapk9−/− mice were stained with either anti-CD4 or anti-CD8 antibodies (green) and counterstained with DAPI (blue). Stained sections of representative infiltrated islets are illustrated.
Figure 4B:
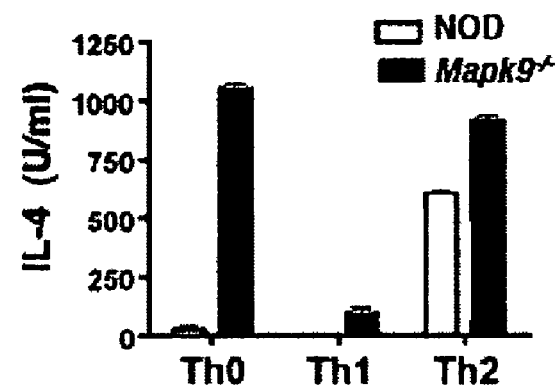
FIG. 4B. CD4+ T cells isolated from 8-week-old female mice were differentiated in the absence (Th0) or the presence of exogenously added polarizing cytokine to Th1 (IL-12) or Th2 (IL-4) effector cells for 4 days. The cells were washed prior to re-stimulation with an immobilized antibody to CD3 for 24 h. Cytokine secretion into the culture supernatant was measured by ELISA. The data presented are the mean±SD of triplicate determinations.
Figure 4B:
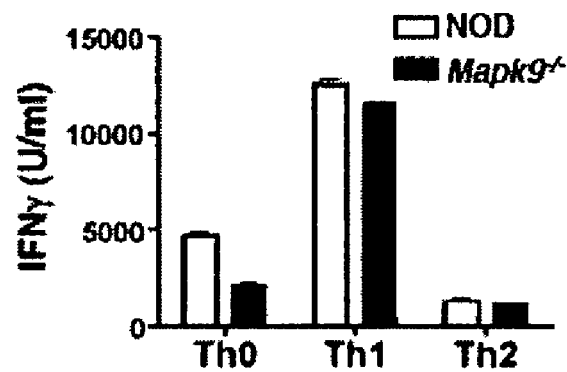
Figure 4B:
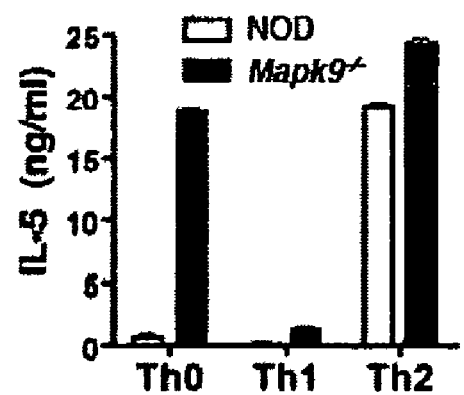

Although the number of infiltrated islets in NOD mice was greater than the number of infiltrated islets in NOD/Mapk9−/− mice (FIG. 2), the percentage of CD4+ and CD8+ T cells within the infiltrated islets was similar in NOD and NOD/Mapk9−/− mice (FIG. 4a). A Th1 (IFN-gamma) environment accelerates the recruitment of islet-specific CD4+ T cells and also accelerates the onset of diabetes, while a Th2 environment protects against autoimmune diabetes. We therefore examined whether JNK2-deficiency in NOD CD4+ T cells could promote the differentiation of these cells into Th2 effector cells. CD4+ T cells were isolated from non-diabetic 8-week-old NOD and JNK2-deficient NOD mice and activated with immobilized anti-CD3 monoclonal antibody (mAb) and soluble anti-CD28 mAb in the presence of IL-4 (to promote Th2 differentiation) or IL-12 (to promoteTh1 differentiation). After 4 days of differentiation, the cells were washed and re-restimulated with immobilized anti-CD3 mAb. Culture supernatants were then harvested 24 h later for analysis of cytokine production. Although WN-gamma secretion by Th1 cells was not significantly affected in JNK2-deficient mice (FIG. 4a), the production of IL-4 by Th2 cells and Th1 cells was substantially increased in these mice compared with wild-type mice (FIG. 4a). Similarly, the secretion of IL-5, another Th2 cytokine, was also augmented in Th2 and Th1 cells from JNK2-deficient mice (FIG. 4b).

Example 5

Figure 4C:
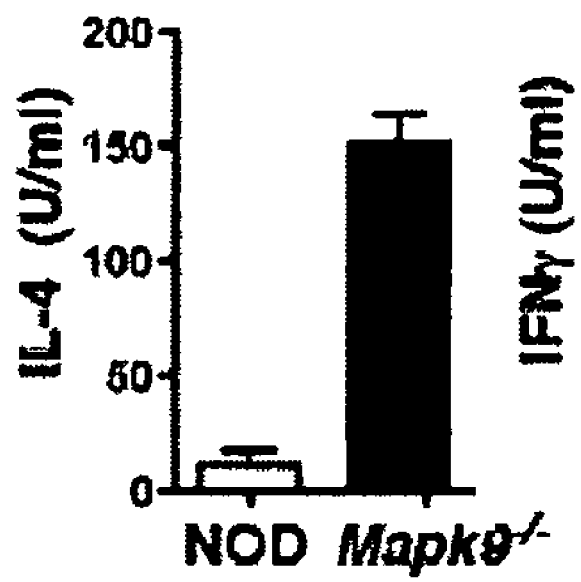
FIG. 4C. Cytokine amounts in the medium of Th0 cultures after differentiation for 4 days and prior to washing and re-stimulation. The data presented are the mean±SD of triplicate determinations.
Figure 4C:
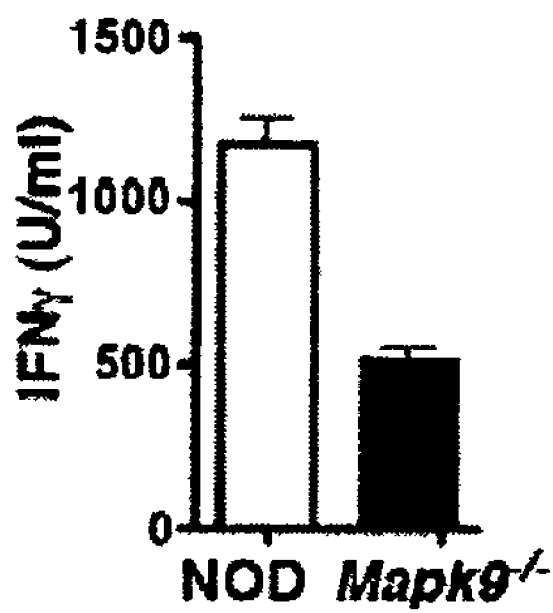

To demonstrate that JNK2-deficiency promoted the production of Th2 cytokines, we examined the cytokine profile of non-polarized effector (Th0) cells differentiated with anti-CD3 and anti-CD28 mAbs in the absence of exogenous cytokines. Although IL-4 secretion by wild-type NOD Th0 cells was not detected, high levels of IL-4 were produced by JNK2-deficient NOD Th0 cells (FIG. 4A). Furthermore, the amount of IL-5 secreted by JNK2-deficient NOD Th0 cells was similar to the high level produced by Th2 cells, but no IL-5 production by NOD Th0 cells was detected. In addition, the expression of IFN-gamma by Th0 cells from JNK2-deficient mice was greatly reduced (FIG. 4b). To test whether this phenotype was due to an impaired differentiation or to an impaired activation of effector cells, we examined cytokine production during the differentiation (days 3 and 4) of CD4+ T cells in the absence of exogenous cytokines. IL-4 was detected in cultures of differentiating JNK2-deficient CD4+ T cells (FIG. 4b). In contrast, the JNK2-deficient CD4+ T cells produced lower levels of IFN-gamma compared with NOD CD4+ T cells (FIG. 4c). Together, these data indicate that JNK2-deficiency caused an intrinsic polarization of NOD CD4+ T cells towards Th2 effectors independently of the cytokine environment. Control studies demonstrated that the Th1/2 polarization of CD4+ T cells from JNK1-deficient (Mapk8-/-) NOD mice was similar to wild-type NOD mice, indicating a selective role for JNK2 in the regulation of CD4+ T differentiation in NOD mice.

Total CD4+ cells were isolated from spleen and lymph nodes by negative selection using anti-NK1.1 (Pharmigen), anti-CD8 (TB105), anti-Mac1 (Pharmingen), and anti-MHC class II (m5/115) mAbs followed by depletion with magnetic beads. CD4+ T cells were activated (106 cells/ml) with immobilized anti-CD3 mAb (2C11) (5 µg/ml) and anti-CD28 mAb (Pharmingen) (1 µg/ml) in the presence of medium (for Th0 cells), IL-4 (for Th2 cells) (R&D) (103 U/ml) or IL-12 (for Th1 cells) (Genetics Institute) (3.5 ng/ml) for four days. Cells were then extensively washed, counted and equal number of cells were restimulated with immobilized anti-CD3 mAb for 24 h when supernatant was harvested. Cytokine production was determine by ELISAs using anti-IL4 or anti-IFN-γ mAb (2 µg/ml), biotinylated anti-IL4 or anti-IFN-γ mAb (1 µg/ml) (Pharmingen), horseradish peroxidase conjugated avidin D (Sigma), peroxidase substrate and reaction stop solutions Example 6

Figure 3B:
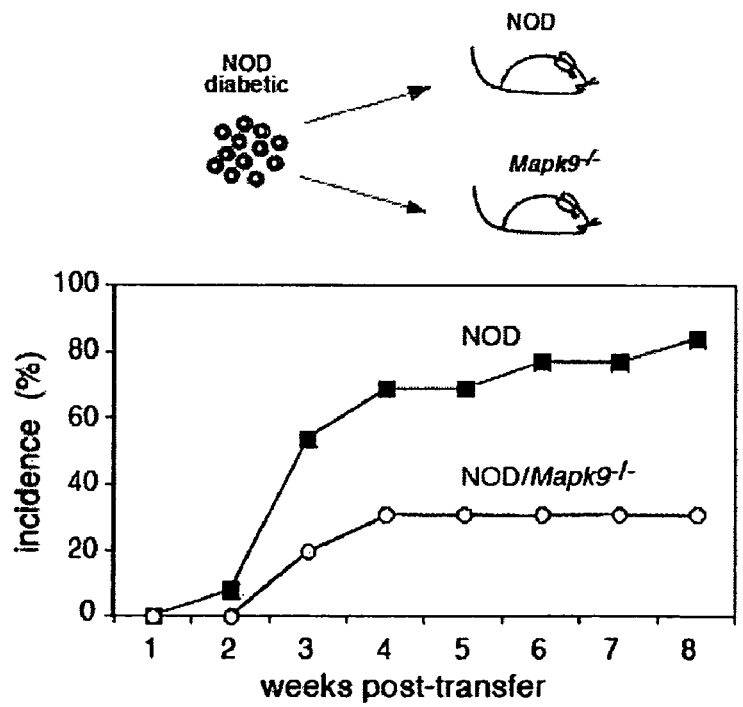
FIG. 3B. Splenocytes isolated from diabetic NOD mice were adoptively transferred irradiated NOD or NOD/Mapk9−/− male mice. The incidence of diabetes was monitored post-transplantation.

We also tested whether the resistance of JNK2-deficient NOD mice to insulitis was exclusively due to the Th2 phenotype of CD4+ T cells or whether JNK2 could also contribute to islet β cell death. Adoptive transfer of T cells isolated from diabetic NOD donor mice causes rapid development of diabetes in sub-lethally irradiated NOD host mice within 2 to 4 weeks. We therefore transferred splenocytes from recently diagnosed diabetic female NOD mice into irradiated male NOD and NOD/Mapk9-/- mice. The frequency of diabetes caused by the T cells isolated from diabetic NOD mice was significantly reduced when these cells were introduced into JNK2-deficient NOD mice compared to control NOD mice (FIG. 3b). The JNK2-deficient NOD group of recipient mice exhibited reduced diabetes compared with the control group of NOD mice after 8 weeks. These data suggest that JNK2-deficiency may also increase resistance of β cells to apoptosis. Although NOD/Mapk9-/- beta cells and NOD beta cells were found to be equally sensitive to apoptosis induced by IL-1beta, TNF-alpha, and IFN-gamma in vitro, it is possible that JNK2-deficiency might enhance resistance to death induced by other T cell mediators, including perforin, granzyme, or Fas ligand.

Example 7

Islets are taken from a donor pancreas and transferred into another person. Once implanted, the β-cells in these islets begin to make and release insulin. A 5-amino-anthra(9,1-cd) isothiazol-6-one is administer to a subject before, during, or after islet transplant surgery.

We claim:

1. A method for treating type I diabetes in a subject, comprising administering a selective JNK2 inhibitor peptide that inhibits activity of JNK2 in the subject wherein said inhibitor peptide is selected from the group consisting of SEQ ID NO: 3, SEQ ID NO: 4, SEQ ID NO: 5, and SEQ ID NO: 6, wherein said SEQ ID NO: 3 is 23 amino acids long, said SEQ ID NO: 4 is 21 amino acids long, SEQ ID NO: 5 is 11 amino acids long, and said SEQ ID NO: 6 is 21 amino acids long.

2. The method of claim 1, wherein the compound inhibits enzymatic activity of JNK2, and has minimal effect on inhibiting enzymatic activity of JNK1.

3. The method of claim 1 in which the activity of JNK1 is not inhibited.

4. The method in claim 1, wherein the activity of the compound does not result in an adverse drug reaction to the subject.

* * * * *